US007537767B2

(12) United States Patent
Bachmann et al.

(10) Patent No.: US 7,537,767 B2
(45) Date of Patent: *May 26, 2009

(54) MELAN-A- CARRIER CONJUGATES

(75) Inventors: Martin F. Bachmann, Seuzach (CH); Vania Manolova, Zurich (CH); Edwin Meijerink, Zurich (CH); Karl G. Proba, Zurich (CH); Katrin Schwartz, Schlieren (CH)

(73) Assignee: Cytis Biotechnology AG (CH)

( * ) Notice: Subject to any disclaimer, the term of this patent is extended or adjusted under 35 U.S.C. 154(b) by 265 days.

This patent is subject to a terminal disclaimer.

(21) Appl. No.: 10/551,054

(22) PCT Filed: Mar. 25, 2004

(86) PCT No.: PCT/EP2004/003164

§ 371 (c)(1),
(2), (4) Date: Sep. 23, 2005

(87) PCT Pub. No.: WO2004/085635

PCT Pub. Date: Oct. 7, 2004

(65) Prior Publication Data

US 2006/0204475 A1 Sep. 14, 2006

Related U.S. Application Data

(60) Provisional application No. 60/457,348, filed on Mar. 26, 2003.

(51) Int. Cl.
*A61K 39/00* (2006.01)
*A61K 39/12* (2006.01)
*A61K 39/385* (2006.01)

(52) U.S. Cl. .............................. 424/185.1; 424/196.11; 424/277.1

(58) Field of Classification Search ....................... None
See application file for complete search history.

(56) References Cited

U.S. PATENT DOCUMENTS

| | | | |
|---|---|---|---|
| 4,722,840 | A | 2/1988 | Valenzuela et al. |
| 4,959,314 | A | 9/1990 | Mark et al. |
| 5,143,726 | A | 9/1992 | Thornton et al. |
| 5,565,548 | A | 10/1996 | Neurath et al. |
| 5,698,424 | A | 12/1997 | Mastico et al. |
| 5,844,075 | A | 12/1998 | Kawakami et al. |
| 5,874,560 | A | 2/1999 | Kawakami et al. |
| 5,935,821 | A | 8/1999 | Chatterjee et al. |
| 5,939,598 | A | 8/1999 | Kucherlapati et al. |
| 5,962,636 | A | 10/1999 | Bachmaier et al. |
| 5,994,523 | A | 11/1999 | Kawakami et al. |
| 6,025,470 | A | 2/2000 | Valmori et al. |
| 6,159,728 | A | 12/2000 | Stockley et al. |
| 6,231,864 | B1 | 5/2001 | Birkett |
| 6,270,778 | B1 | 8/2001 | Kawakami et al. |
| 6,277,956 | B1 | 8/2001 | Valmori et al. |
| 6,326,200 | B1 | 12/2001 | Valmori et al. |
| 6,368,857 | B1 | 4/2002 | Valmori et al. |
| 6,380,364 | B1 | 4/2002 | Mueller et al. |
| 6,384,190 | B1 | 5/2002 | Valmori et al. |
| 6,537,560 | B1 | 3/2003 | Kawakami et al. |
| 6,627,202 | B2 | 9/2003 | Murray |
| 6,719,978 | B2 | 4/2004 | Schiller et al. |
| 6,949,520 | B1 | 9/2005 | Hartmann et al. |
| 6,965,017 | B2 | 11/2005 | Kawakami et al. |
| 2001/0044416 | A1 | 11/2001 | McCluskie et al. |
| 2003/0026782 | A1 | 2/2003 | Krieg et al. |
| 2003/0050268 | A1 | 3/2003 | Krieg |
| 2003/0060440 | A1 | 3/2003 | Klinman et al. |
| 2003/0082804 | A1 | 5/2003 | Valmori et al. |
| 2003/0087848 | A1 | 5/2003 | Bratzler et al. |
| 2003/0099668 | A1* | 5/2003 | Bachmann et al. ....... 424/204.1 |
| 2005/0169888 | A1 | 8/2005 | Hartmann et al. |
| 2006/0286070 | A1 | 12/2006 | Hartmann et al. |

FOREIGN PATENT DOCUMENTS

| | | | |
|---|---|---|---|
| EP | 0 038 154 | B1 | 10/1981 |
| EP | 0 201 416 | B1 | 4/1991 |
| EP | 0 421 635 | A1 | 4/1991 |
| EP | 0 468 520 | A2 | 1/1992 |
| EP | 0 578 293 | A1 | 1/1994 |

(Continued)

OTHER PUBLICATIONS

Blanchet et al (Journal of Immunology 167:5858-5861, 2001.*
Miconnet et al, "CpG are efficient adjuvants for specific CTL induction against tumor antigen-derived peptide," Journal of Immunology (2002), 168(3), 1212-1218.*
Romero et al, "Antigenicity and immunogenicity of Melan-A/MART-1 derived peptides as targets for tumor reactive CTL in human melanoma," Immunological reviews, Oct. 2002, 188, 81-96.*

(Continued)

*Primary Examiner*—Mary E Mosher
(74) *Attorney, Agent, or Firm*—Sterne, Kessler, Goldstein & Fox P.L.L.C.

(57) ABSTRACT

The present invention is related to the fields of molecular biology, virology, immunology and medicine. The invention provides a modified virus-like particle (VLP) comprising a VLP which can be loaded with immunostimulatory substances, in particular with DNA oligonucleotides containing non-methylated C and G (CpGs), and particular peptides derived from MelanA linked thereto. Such CpGVLPs are dramatically more immunogenic than their CpG-free counterparts and induce enhanced B and T cell responses. The immune response against MelanA peptide analogues optionally coupled, fused or attached otherwise to the VLPs is similarly enhanced as the immune response against the VLP itself. In addition, the T cell responses against the MelanA peptide analogues are especially directed to the Thl type. Antigens attached to CpG-loaded VLPs may therefore be ideal vaccines for prophylactic or therapeutic vaccination against allergies, tumors and other self-molecules and chronic viral diseases.

58 Claims, 4 Drawing Sheets

FOREIGN PATENT DOCUMENTS

Figure 1:
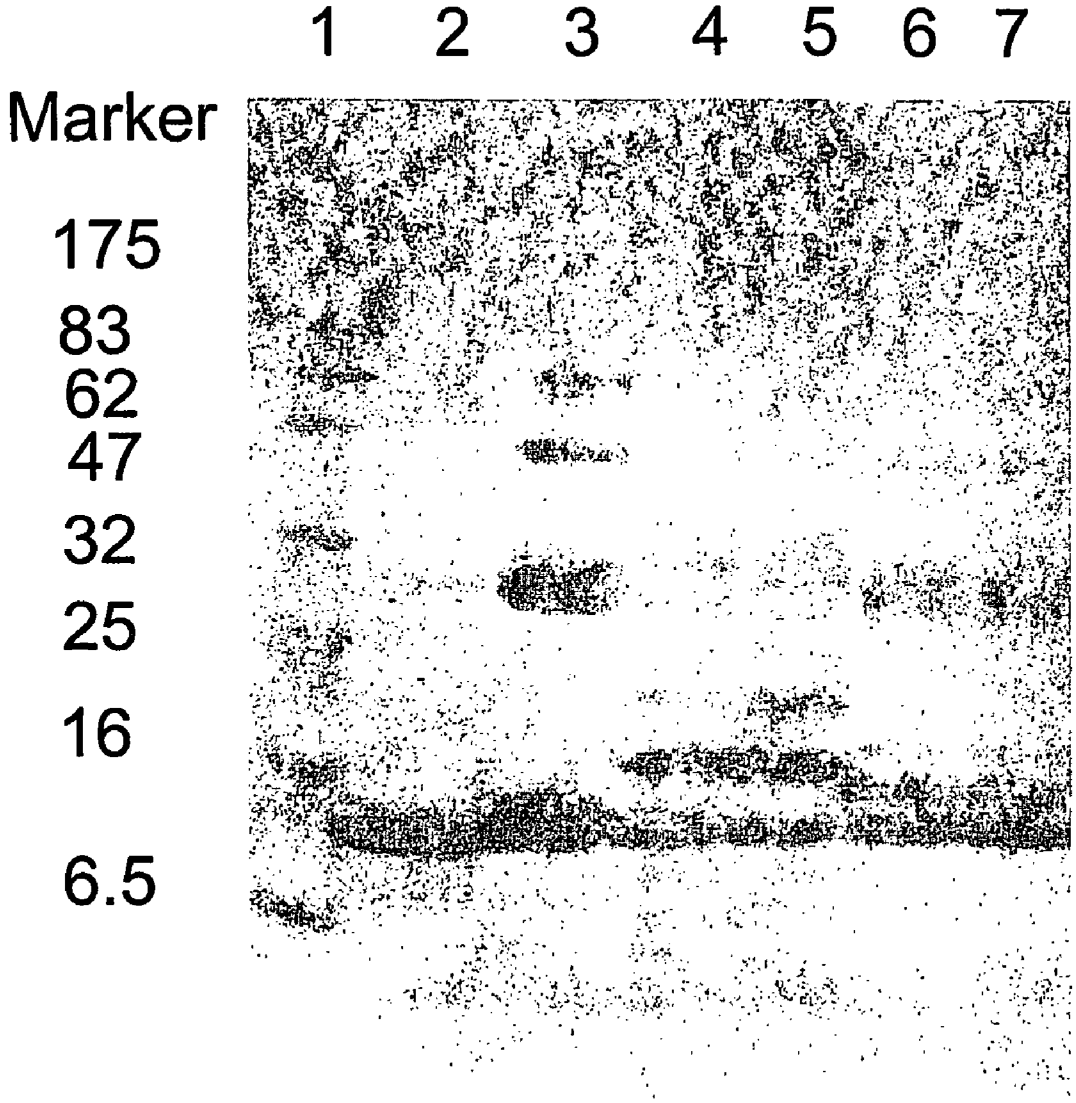

| | | | |
|---|---|---|---|
| EP | 0 385 610 B1 | | 3/1994 |
| EP | 0 772 619 B1 | | 5/1997 |
| EP | 0 855 184 A1 | | 7/1998 |
| WO | WO 92/11291 A1 | | 7/1992 |
| WO | WO 92/13081 | | 8/1992 |
| WO | WO 94/02499 A1 | | 2/1994 |
| WO | WO 94/14969 A1 | | 7/1994 |
| WO | WO 95/26204 A1 | | 10/1995 |
| WO | WO 95/29193 A2 | | 11/1995 |
| WO | WO 96/02555 A1 | | 2/1996 |
| WO | WO 96/30523 A2 | | 10/1996 |
| WO | WO 97/28259 A1 | | 8/1997 |
| WO | WO 98/18810 A1 | | 5/1998 |
| WO | WO 98/33517 A1 | | 8/1998 |
| WO | WO98/40100 A1 | | 9/1998 |
| WO | WO 98/49195 A1 | | 11/1998 |
| WO | WO 98/50071 A1 | | 11/1998 |
| WO | WO 98/52581 A1 | | 11/1998 |
| WO | WO 98/55495 A2 | | 12/1998 |
| WO | WO 98/58751 A1 | | 12/1998 |
| WO | WO 98/58951 A1 | | 12/1998 |
| WO | WO 99/11275 A2 | | 3/1999 |
| WO | WO 99/28478 A1 | | 6/1999 |
| WO | WO 99/29723 A1 | | 6/1999 |
| WO | WO 99/40934 A1 | | 8/1999 |
| WO | WO 99/51259 A2 | | 10/1999 |
| WO | WO 99/57289 A2 | | 11/1999 |
| WO | WO 00/06588 A1 | | 2/2000 |
| WO | WO 00/14217 A2 | | 3/2000 |
| WO | WO 00/23955 A1 | | 4/2000 |
| WO | WO 00/32227 A2 | | 6/2000 |
| WO | WO 00/37610 A2 | | 6/2000 |
| WO | WO 00/39304 A2 | | 7/2000 |
| WO | WO 00/50461 A1 | | 8/2000 |
| WO | WO 00/62800 A2 | | 10/2000 |
| WO | WO 01/16320 | * | 3/2001 |
| WO | WO 01/16320 A1 | | 3/2001 |
| WO | WO 01/22972 A2 | | 4/2001 |
| WO | WO 01/22990 A2 | | 4/2001 |
| WO | WO 01/56603 A1 | | 8/2001 |
| WO | WO 01/58478 A1 | | 8/2001 |
| WO | WO 01/77158 A1 | | 10/2001 |
| WO | WO 01/85208 A2 | | 11/2001 |
| WO | WO 01/98333 A2 | | 12/2001 |
| WO | WO 02/10416 A1 | | 2/2002 |
| WO | WO 02/14478 A2 | | 2/2002 |
| WO | WO 02/053141 A2 | | 7/2002 |
| WO | WO 02/056905 A2 | | 7/2002 |
| WO | WO 02/056907 A2 | | 7/2002 |
| WO | WO 03/024480 A2 | | 3/2003 |
| WO | WO 03/024481 A2 | | 3/2003 |
| WO | WO 03/030656 A2 | | 4/2003 |
| WO | WO 03/031466 A2 | | 4/2003 |
| WO | WO 03/039225 A2 | | 5/2003 |
| WO | WO 03/040308 A2 | | 5/2003 |
| WO | WO 03/040164 A2 | | 6/2003 |
| WO | WO 03/045431 A2 | | 6/2003 |
| WO | WO 03/059386 A2 | | 7/2003 |
| WO | WO 2004/000351 A1 | | 12/2003 |
| WO | WO 2004/007538 A2 | | 1/2004 |
| WO | WO2005/014110 A1 | | 2/2005 |

OTHER PUBLICATIONS

Le Gal et al, "Lipopeptide-based melanoma cancer vaccine induced a strong MART-27-35-cytotoxic T lymphocyte response in a preclincal study," International journal of cancer, Mar. 10, 2002, 98(2), 221-227.*

Storni et al, "Critical role for activation of antigen-presenting cells in priming of cytotoxic T cell responses after vaccination with virus-like particles," Journal of immunology, Mar. 15, 2002, 168(6), 2880-2886 (in IDS).*

Clark et al, "Immunity against both polyoma virus VP1 and a transgene product induced following intranasal delivery of VP1 pseudocapsid-DNA complexes," J. Gen.Virol. (82, Pt. 11, 2791-97) 2001 (in IDS).*

Shi et al, "Papillomavirus pseudovirus: a novel vaccine to induce mucosal and systemic cytotoxic T-lymphocyte responses," Journal of virology, Nov. 2001, 75(21), 10139-10148.*

Ballas, Z.K., et al., "Induction of NK Activity in Murine and Human Cells by CpG Motifs in Oligodeoxynucleotides and Bacterial DNA," *J Immunol* 157(5):1840-5, The American Association of Immunologists, Inc. (1996).

Bartholomé, E. J., et al., "IFN-β Interferes with the Differentiation of Dendritic Cells from Periphral Blood Mononuclear Cells: Selective Inhibiiton of CD40-dependent Interleukin-12 Secretion," *J Interferon Cytokine Res* 19(5):471-8, Mary Ann Liebert, Inc. (1999).

Blackwell, S.E., and Krieg, A.M., "CpG-A-Induced Monocyte IFN-γ-Inducible Protein-10 Production is Regulated by Plasmacytoid Dendritic Cell-derived IFN-α," *J Immunol.*170(8):4061-8, The American Association of Immunologists Inc. (Apr. 2003).

Branda, R.F., et al., "Amplification of antibody production by phosphorothioate oligodeoxynucleotides," *J Lab Clin Med* 128(3):329-38, Mosby-Year Book Inc. (1996).

Cella, M., et al., "Maturation, activation, and protection of dendritic cells induced by double-stranded RNA," *J Exp Med* 189(5):821-9, The Rockefeller University Press (1999).

Cella, M., et al., "Plasmacytoid monocytes migrate to inflamed lymph nodes and produce large amounts of type I interferon," *Nat Med* 5(8):919-23, Nature America Inc. (1999).

Clark, B., et al., "Immunity against both polyomavirus VP1 and a transgene product induced following intranasal delivery of VP1 pseudocapsid-DNA complexes," *J. Gen. Virol.* 82:2791-2797, Society for General Microbiology (2001).

Dalpke, A.H., et al., "Phosphodiester CpG oligonucleotides as adjuvants: polyguanosine runs enhance cellular uptake and improve immunostimulative activity of phosphodiester CpG oligonucleotides in vitro and in vivo," *Immulology* 106(1):102-12, Blackwell Science Ltd. (May 2002).

Goeckeritz, B.E., et al., "Multivalent cross-linking of membrane lg sensitizes murine B cells to a broader spectrum of CpG-containing oligodeoxynucleotide motifs, including their methylated couterparts, for stimulation of proliferation and Ig secretion," *Int Immunol* 11(10):1693-700, Oxford University Press (1999).

Halperin, S.A., et al., "A phase I study of the safety and immunogenicity of recombinant hepatitis B surface antigen co-administered with an immunostimulatory phosphorothioate oligonucleotide adjuvant," *Vaccine* 21(19-20):2461-7, Elsevier Science Ltd. (Jun. 2003).

Halpern, M.D., et al., "Bacterial DNA Induces Murine Interferon-γ Production by Stimulation of Interleukin-12 and Tumor Necrosis Factor-α," *Cell Immunol* 167(1):72-8, Academic Press Inc. (1996).

Hartmann, G., et al., "CpG DNA: A potent signal for growth, activation, and maturation of human dendritic cells," *Proc Natl Acad Sci U S A* 96(16):9305-10, National Academy of Sciences (1999).

Heath, A.W., "Cytokines and the Rational Choice of Immunological Adjuvants," *Cancer Biother* 9(1):1-6, Mary Ann Liebert, Inc., Publishers (1994).

Iho, S., et al., "Oligodeoxynucleotides Containing Palindrome Sequences with Internal 5'-CpG-3' Act Directly on Human NK and Activated T Cells to Induce IFN-γ Production In Vitro," *J Immunol* 163(7):3642-52, The American Association of Immunologists (1999).

Ioannou, X.P., et al., "CpG-containing oligodeoxynucleotides, in combination with conventional adjuvants, enhance the magnitude and change the bias of the immune responses to a herpesvirus glycoprotein," *Vaccine* 21(1-2):127-37, Elsevier Science (Nov. 2002).

Kerkmann, M., et al., "Activation with CpG-A and CpG-B Oligonucleotides Reveals Two Distinct Regulatory Pathways of Type I IFN Synthesis in Human Plasmacytoid Dendritic Cells," *J Immunol.* 170(9):4465-74, The American Association of Immunologists Inc (May 2003).
Kline, J.N., et al., "Modulation of Airway Inflammation by CpG Oligodeoxynucleotides in a Murine Model of Asthma," *J Immunol* 160(6):2555-9, The American Association of Immunologists (1998).
Kline, J.N., et al., "Treatment of established asthma in a murine model using CpG oligodeoxynucleotides," *Am J Physiol Lung Cell Mol Physiol* 283(1):L170-9, American Physiological Society (Jul. 2002).
Klinman, D.M., "Immunotherapeutic Uses of CpG Oligodeoxynucleotides," *Nat Rev Immunol* 4(4):249-58, Nature Publishing Group (Apr. 2004).
Klinman, D.M., et al., "CpG motifs present in bacterial DNA rapidly induce lymphocytes to secrete interleukin 6, interleukin 12, and interferon γ," *Proc Natl Acad Sci U S A* 93(7):2879-83, National Academy of Sciences (1996).
Klinman, D.M., et al., "CpG oligonucleotides improve the protective immune response induced by the anthrax vaccination of rhesus macaques," *Vaccine* 22(21-22):2881-6, Elsevier Ltd. (Jul. 2004).
Krieg, A.M., "CpG Motifs in Bacterial DNA and Their Immune Effects," *Annu Rev Immunol* 20:709-60, Annual Reviews (Apr. 2002).
Krieg, A.M., "Mechanisms and applications of immune stimulatory CpG oligodeoxynucleotides," *Biochim Biophys Acta* 1489(1):107-16, Elsevier Science (1999).
Krieg, A.M. and Davis, H.L., "Enhancing vaccines with immune stimulatory CpG DNA," *Curr Opin Mol Ther* 3(1):15-24, Thomson Scientific (2001).
Krieg, A.M., et al., "CpG motifs in bacterial DNA trigger direct B-cell activation," *Nature* 374(6522):546-9, Nature Publishing Group (1995).
Krieg, A.M., et al., "Oligodeoxynucleotide Modifications Determine the Magnitude of B Cell Stimulation by CpG Motifs," *Antisens & Nucleic Acid Drug Dev* 6(2):133-9, Mary Ann Liebert, Inc. (1996).
Krug, A., et al., "CpG-A Oligonucleotides Induce a Monocyte-Derived Dendritic Cell-Like Phenotype that Preferentially Activates CD8 T Cells," *J Immunol.* 170(7):3468-77, The American Association of Immunologists, Inc. (Apr. 2003).
Lee, S.W., et al., "Effects of a Hexameric Deoxyriboguanosine Run Conjugation into CpG Oligodeoxynucleotides on Their Immunostimulatory Potentials," *J Immunol* 165(7):3631-9, The American Association of Immunologists (2000).
Leibl, H.M., et al., "Adjuvant/carrier activity of inactivated tick-borne encephalitis virus," *Vaccine* 16(4):340-5, Elsevier Science Ltd. (1998).
Liu, H.M., et al., "Immunostimulatory CpG Oligodeoxynucleotides Enhance the Immune Response to Vaccine Strategies Involving Granulocyte-Macrophage Colony-Stimulating Factor," *Blood* 92(10):3730-6, The American Society of Hematology (1998).
Mahon, B.P., et al., "The Rational Design of Vaccine Adjuvants for Mucosal and Neonatal Immunization," *Curr Med Chem* 8(9):1057-75, Bentham Science Publishers (2001).
Pisetsky, D.S. and Reich, C.F., "Stimulation of Murine Lymphocyte Proliferation by a Phosphorothioate Oligonucleotide with Antisense Activity for Herpes Simplex Virus," *Life Sci* 54(2):101-7, Pergamon Press (1994).
Putney, S.D., et al. "Enhanced Anti-Tumor Effects with Microencapsulated *c-myc* Antisense Oligonucleotide," *Antisense Nucleic Acid Drug Dev.* 9:451-8, Mary Ann Liebert Inc. (1999).
Raz, E., "Introduction: gene vaccination, current concepts and future directions," *Springer Semin Immunopathol* 19(2):131-7, Springer-Verlag (1997).
Raz, E., et al., "Preferential induction of a $Th_1$ immune response and inhibition of specific lgE antibody formation by plasmid DNA immunization," *Proc Natl Acad Sci USA* 93(10):5141-5, National Academy of Sciences (1996).
Sato, Y., et al., "Immunostimulatory DNA Sequences Necessary for Effective Intradermal Gene Immunization," *Science* 273(5273):352-4, American Association for the Advancement of Science (1996).
Schwarz, K., et al., "Role of Toll-Like receptors in costimulating cytotoxic T cell responses," *Eur. J. Immunol.* 33:1465-70, Wiley-VCH Verlag (Jun. 2003).
Semple, S.C., et al., "Lipid-Based Formulations of Antisense Oligonucleotides for Systemic Delivery Applications," *Methods Enzymol.* 313:322-41, Academic Press (2000).
Siegal, F.P., et al., "The Nature of the Principal Type 1 Interferon-Producing Cells in Human Blood," *Science* 284(5421):1835-7, American Association for the Advancement of Science (1999).
Takauji, R., et al., "CpG-DNA-induced IFN-α production involves p38 MAPK-dependent STAT1 phosphorylation in human plasmacytoid dendritic cell precursors," *J. Leukoc. Biol. 72*:1011-1019, Wiley-Liss (Nov. 2002).
Uhlmann, E. and Vollmer, J., "Recent advances in the development of immunostimulatory oligonucleotides," *Curr Opin Drug Discov Devel* 6(2):204-17, Thomson Scientific (Mar. 2003).
Van Ojik, H., et al., " Phase I/II study with CpG 7909 as adjuvant to vaccination with MAGE-3 protein in patients with MAGE-3 positive tumors," *Ann. Oncol. 13*:157-158, Abstract No. 579O, Oxford University Press (Oct. 2002).
Verthelyi, D., et al., "CpG oligodeoxynucleotides improve the response to hepatitis B immunization in healthy and SIV-infected rhesus macaques," *AIDS* 18(7):1003-8, Lippincott Williams & Wilkins (Apr. 2004).
Verthelyi, D., et al., "Human Peripheral Blood Cells Differentially Recognize and Respond to Two Distinct CPG Motifs," *J Immunol* 166(4):2372-7, The American Association of Immunologists (2001).
Vollmer, J., et al., "Characterization of three CpG oligodeoxynucleotide classes with distinct immunostimulatory activities," *Eur. J. Immunol.* 34:251-262, WILEY-VCH Verlag (Jan. 2004).
Vrtala, S., et al., "Immunization with Purified Natural and Recombinant Allergens Induces Mouse lgG1 Antibodies That Recognize Similar Epitopes as Human lgE and Inhibit the Human lgE-Allergen Interaction and Allergen-Induced Basophil Degranulation," *J. Immunol. 160*:6137-6144, The American Association of Immunologists, Inc. (1998).
Weiner, G., "Declaration of Dr. George Weiner Under 37 CFR § 1.32," submitted in support of U.S. Appl. No. 09/286,098, 9 pages (2000).
Weiner, G.J., et al., "Immunostimulatory oligodeoxynucleotides containing the CpG motif are effective as immune adjuvants in tumor antigen immunization," *Proc Natl Acad Sci USA* 94(20):10833-7, National Academy of Sciences (1997).
Yamamoto, T., et al., "Ability of Oligonucleotides with Certain Palindromes to lnduce Interferon Production and Augment Natural Killer Cell Activity is Associated with Their Base Length," *Antisense Res Dev* 4(2):119-22, Mary Ann Liebert Inc. (1994).
Yamamoto, T., et al., "Synthetic oligonucleotides with certain palindromes stimulate interferon production of human peripheral blood lymphocytes in vitro," *Jpn J Cancer Res* 85(8):775-9, Japanese Cancer Association (1994).
Yu, D., et al., "Potent CpG oligonucleotides containing phosphodiester linkages: in vitro and in vivo immunostimulatory properties," *Biochem Biophys Res Commun* 297(1):83-90, Academic Press (Sep. 2002).
Adams, S.E., et al., "The expression of hybrid HIV:Ty virus-like particles in yeast," *Nature* 329:68-70, Nature Publishing Group (1987).
Addo, M.M., et al., "Comprehensive Epitope Analysis of Human Immunodeficiency Virus Type 1 (HIV-1)-Specific T-Cell Responses Directed against the Entire Expressed HIV-1 Genome Demonstrate Broadly Directed Responses, but No Correlation to Viral Load," *J. Virol. 77*:2081-2092, American Society for Microbiology (Feb. 2003).
Bachmann, M.F., and Zinkernagel, R., "The influence of virus structure on antibody responses and virus serotype formation," *Immunol. Today 17*:553-558, Elsevier Science (1996).
Bachmann, M.F., and Zinkernagel, R.M., "Neutralizing Antiviral B Cell Responses," *Ann. Rev. Immunol. 15*:235-270, Annual Reviews, Inc. (1997).
Brown, W.L., et al., "RNA Bacteriophage Capsid-Mediated Drug Delivery and Epitope Presentation," *Intervirol. 45*:371-380, S. Karger AG (Jul.-Dec. 2002).
Buonaguro, L., et al., "High efficient production of $Pr55^{gag}$ virus-like particles expressing multiple HIV-1 epitopes, including a gp120 protein derived from an Ugandan HIV-1 isolate of subtype A," *Antiviral Res* 49:35-47, Elsevier Science B.V. (2001).
Chackerian, B., et al ., "Induction of autoantibodies to mouse CCR5 with recombinant papillomavirus particles," *Proc. Natl. Acad. Sci. USA 96*:2373-2378, The National Academy of Sciences (1999).
Chen, J.L., et al., "Identification of NY-ESO-1 Peptide Analogues Capable of Improved Stimulation of Tumor-Reactive CTL," *J. Immunol. 165*:948-55, The American Association of Immunologists (2000).
Cohen, P.A., et al., "$CD4^+$ T-Cells from Mice Immunized to Syngeneic Sarcomas Recognize Distinct, Non-Shared Tumor Antigens," *Cancer Research 54*:1055-8, American Association for Cancer Research (1994).
De Clercq, E., "Interferon Induction by Polynucleotides, Modified Polynucleotides, and Polycarboxylates," *Methods Enzymol. 78*:227-36, Academic Press, Inc. (1981).
Dudley, M.E., et al., "Cancer Regression and Autoimmunity in Patients After Clonal Repopulation with Antitumor Lymphocytes," *Science 298*:850-854, American Association for the Advancement of Science (Oct. 2002).
Engleman, E.G., "Dendritic cells: Potential role in cancer therapy," *Cytotechnol. 25*:1-8, Kluwer Academic Publishers (1997).
Fehr, T., et al., "Role of Repetitive Antigen Patterns for Induction of Antibodies Against Antibodies," *J. Exp. Med. 185*:1785-92, The Rockefeller University Press (1997).
Fehr, T., et al., "T cell-independent type I antibody response against B cell epitopes expressed repetitively on recombinant virus particles," *Proc. Natl. Acad. Sci. USA 95*:9477-9481, The National Academy of Sciences (1998).
Firat, H., et al., "H-2 class I knockout, HLA-A2.1-transgenic mice: a versatile animal model for preclinical evaluation of antitumor immunotherapeutic strategies," *Eur. J. Immunol. 29*:3112-3121, WILEY-VCH Verlag GmbH (1999).
FItchen, J., et al., "Plant virus expressing hybrid coat protein with added murine epitope elicits autoantibody response," *Vaccine 13*:1051-1057, Elsevier Science (1995).
Gerber, S., et al., "Human Papillomavirus Virus-Like Particles Are Efficient Oral Immunogens when Coadministered with *Escherichia coli* Heat-Labile Enterotoxin Mutant R192G or CpG DNA," *J. Virol. 75*:4752-60, American Society for Microbiology (2001).
Geysen, H.M., et al., "Use of peptide synthesis to probe viral antigens for epitopes to a resolution of a single amino acid," *Proc. Natl. Acad. Sci. USA 81*:3998-4002, The National Academy of Sciences (1984).
Gilbert, S.C., et al., "A protein particle vaccine containing multiple malaria epitopes," *Nat. Biotechnol. 15*:1280-1284, Nature America Publishing (1997).
Gluckman, J.C., et al., "In vitro generation of human dendritic cells and cell therapy," *Cytokines Cell. Mol. Ther. 3*:187-96, Martin Dunitz Ltd. (1997).
Golmohammadi, R., et al., "The crystal structure of bacteriophage Qβ at 3.5 Å resolution," *Structure 4*:543-554, Current Biology Ltd. (1996).
Graff-Dubois, S., et. al., "Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy," *J. Immunol.* 169:575-580, The American Association of Immunologists, Inc. (Jul. 2002).
Harada, M., et. al., "Use of an in Vitro Immunoselected Tumor Line to Identify Shared Melanoma Antigens Recognized by HLA-A*0201-restricted T Cells," *Cancer Res. 61*:1089-1094, American Association for Cancer Research (2001).
Huston, J.S., et al., "Protein Engineering of Single-Chain Fv Analogs and Fusion Proteins," *Methods Enzymol. 203*:46-88, Academic Press, Inc. (1991).
Jegerlehner, A., et al., "A molecular assembly system that renders antigens of choice highly repetitive for induction of protective B cell responses," *Vaccince 20*:3104-3012, Elsevier Science Ltd. (Aug. 2002).
Kaisho, T. and Akira, S., "Toll-like receptors as adjuvant receptors," *Biochim. Biophys. Acta 1589*:1-13, Elsevier Science (Feb. 2002).
Kang, C.Y., et al., "Development of HIV/AIDS Vaccine Using Chimeric gag-env Virus-Like Particles," *Biol. Chem. 380*:353-64, Walter De Gruyter (1999).
Klinman, D.M., et al., "Immunotherapeutic Applications of CpG-Containing Oligodeoxynucleotides," *Drug News Perspect. 13*:289-296, Prous Science (2000).
Klovins,J., et al., "Nucleotide sequence of a ssRNA phage from *Acinetobacter*: kinship to coliphages," *J. Gen. Virol. 83*:1523-1533, SGM (Jun. 2002).
Kobayashi H., et. al., "Tyrosinase epitope recognized by an HLA-DR-restricted T-cell line from a Vogt-Koyanagi-Harada disease patient," *Immunogenet. 47*:398-403, Springer-Verlag (1998).
Kobayashi, H., et. al., "Tumor-reactive T Helper Lymphocytes Recognize a Promiscuous MAGE-A3 Epitope Presented by Various Major Histocompatibility Complex Class II Alleles," *Cancer Res. 61*:4773-4778, American Association for Cancer Research (2001).
Kozlovska, T. M., et al., "RNA Phage Qβ Coat Protein as as Carrier for Foreign Epitopes," *Intervirol. 39*:9-15, S. Karger AG Basel (1996).
Kozlovska, T. M., et al., "Recombinant RNA phage Qβ capsid particles synthesized and self-assembled in *Escherichia coli," Gene 137*:133-137, Elsevier Science Publishers B.V. (1993).
Kratz, P.A., et al., "Native display of complete foreign protein domains on the surface of hepatitis B virus capsids," *Proc. Natl. Acad. USA 96*:1915-1920, The National Academy of Sciences (1999).
Krug, A., et al., "Identification of CpG oligonucleotide sequences with high induction of IFN-α/β in plasmacytoid dendritic cells," *Eur. J. Immunol. 31*:2154-63, WILEY Verlag GmbH (2001).
Kuramoto, E., et al., "Oligonucleotide Sequences Required for Natural Killer Cell Activation," *Jpn. J. Cancer Res.* 83:1128-1131, Japanese Cancer Association (1992).
Lechner, F., et al., "Virus-like Particles as a Modular System for Novel Vaccines," *Intervirol.* 45:212-217, S. Karger AG (Jul.-Dec. 2002).
Levy, H.B., "Induction of Interferon in Vivo and in Vitro by Polynucleotides and Derivatives, and Preparation of Derivatives," *Methods Enzymol. 78*:242-51, Academic Press, Inc. (1981).
Li, Y., et al., "Vaccination Against Angiogenesis-Associated Antigens: A Novel Cancer Immunotherapy Strategy," *Curr. Mol. Med.* 3:773-779, Bentham Science Publishers Ltd. (Dec. 2003).
Linette, G.P., et. al., "In Vitro Priming with Adenovirus/gp100 Antigen-Transduced Dendritic Cells Reveals the Epitope Specificity of HLA-A*0201-Restricted $CD8^+$ T cells in Patients with Melanoma," *J. Immunol.*164:3402-3412, The American Association of Immunologists (2000).
Luo, L., et al., "Induction of V3-Specific Cytotoxic T Lymphocyte Responses by HIV *gag* Particles Carrying Multiple Immunodominant V3 Epitopes of gp 120," *Virol.* 240:316-325, Academic Press (1998).
Malling, H.-J., and Taudorf, E., "Allergenicity of alum-precipitated grass pollen extracts with different RAST activity," *Clin. Allergy* 17:399-404, Blackwell Scientific Publications (1987).
Martin, S.J., et al., "Immunization of hhuman HIV-seronegative volunteers with recombinant p17/p24:Ty virus-like particles elicits HIV-1 p24-specific cellular and humoral immune responses," *AIDS 7*:1315-23, Current Science Ltd. (1993).
Moss, R.B., et al., "In vitro immune function after vaccination with an inactivated, gp120-depleted HIV-1 antigen with immunostimulatory oligodeoxynucleotides," *Vaccine 18*:1081-7, Elsevier Science Ltd. (2000).
Neirynck, S., et al., "A universal influenza A vaccine based on the extracellular domain of the M2 protein," *Nature Med. 5*:1157-63, Nature Publishing Company (1999).
Nieland, J.D., et al., "Chimeric Papillomavirus Virus-like Particles Induce a Murine Self-Antigen-Specific Protective and Therapeutic Antitumor Immune Response," *J. Cell. Biochem. 73*:145-152. Wiley-Liss, Inc. (1999).
Nielsen, M.B., et. al., "Status of Activation of Circulating Vaccine-Elicited $CD8^+$ T Cells," *J. Immunol. 165*:2287-96, The American Association of Immunologists (2000).
Notka, F., et al., "Accelerated clearance of SHIV in rhesus monkeys by virus-like particle vaccines is dependent on induction of neutralizing antibodies," *Vaccine 18*:291-301, Elsevier Science Ltd. (2000).
Nussbaum, A.K., et al., "PAProC: a prediction algorithm for proteasomal cleavages available on the WWW," *Immunogenet. 53*:87-94, Springer-Verlag (2001).

Oxenius, A., et al., "CpG-Containing Oligonucleotides Are Efficient Adjuvants for Induction of Protective Antiviral Immune Responses with T-Cell Peptide Vaccines," *J. Virol. 73*:4120-4126, American Society for Microbiology (1999).

Panelli, M.C., et. al., "Expansion of Tumor-T Cell Pairs from Fine Needle Aspirates of Melanoma Metastases," *J. Immunol. 164*:495-504, The American Association of Immunologists (2000).

Parkhurst, M.R., et. al., "Identification of a Shared HLA-A*0201-restricted T-Cell Epitope from the Melanoma Antigen Tyrosinase-related Protein 2 (TRP2)," *Cancer Res. 58*:4895-4901, American Association for Cancer Research (1998).

Pasek, M., et al., "Hepatitis B virus genes and their expression in *E. coli," Nature* 282:575-579, Macmillan Journals Ltd. (1979).

Pass, H.A., et al., "Immunization of Patients with Melanoma Peptide Vaccines: Immunologic Assessment Using the ELISPOT Assay," *Cancer J. Sci. Am.* 4:316-323, Scientific American, Inc. (1998).

Pumpens, P. and Grens, E., "HBV Core Particles as a Carrier for B Cell/T Cell Epitopes," *Intervirol*. 44:98-114, S. Karger AG (2001).

Pushko, P., et al., "Analysis of RNA phage *fr* coat protein assembly by insertion, deletion and substitution mutagenesis," *Protein Eng.* 6:883-891, Oxford University Press (1993).

Rammensee, H., et al., "SYFPEITHI: database for MHC ligands and peptide motifs," *Immunogenet*. 50:213-219, Springer-Verlag (1999).

Roth, J.F., "The yeast Ty virus-like particles," *Yeast 16*:785-795, John Wiley & Sons, Ltd. (2000).

Rueda, P., et al., "Minor Displacements in the Insertion Site Provoke Major Differences in the Induction of Antibody Responses by Chimeric Parvovirus-like Particles," *Virol. 263*:89-99, Academic Press (1999).

Sallusto, F. and Lanzavecchia, A., "Efficient Presentation of Soluable Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.* 179:1109-1118, The Rockefeller University Press (1994).

Salunke, D.M., et al., "Self-Assembly of Purified Polyomavirus Capsid Protein $VP_1$," *Cell 46*:895-904, Cell Press (1986).

Sasnauskas, K., et al., "Yeast Cells Allow High-Level Expression and Formation of Polyomavirus-Like Particles," *Biol. Chem. 380*:381-6, Walter de Gruyter (1999).

Skipper, J.C.A., et al., "Mass-Spectrometric Evaluation of HLA-A*0201-Associated Peptides Identifies Dominant Naturally Processed Forms of CTL Epitopes from MART-1 and gp100," *Int. J. Cancer 82*:669-677, Wiley-Liss Inc. (1999).

Slepushkin, V.A., et al., "Protection of mice against influenza A virus challenge by vaccination with baculovirus-expressed M2 protein," *Vaccine 13*:1399-1402, Elsevier Science (1995).

Smiley, B.K. and Minion, F.C., "Enhanced readthrough of opal (UGA) stop codons and production of *Mycoplasma pneumoniae* P1 epitopes in *Escherichia coli," Gene 134*:33-40, Elsevier Science Publishers B.V. (1993).

Sparwasser, T., et al., "Immunostimulatory CpG-Oligodeoxynucleotides Cause Extramedullary Murine Hemopoiesis," *J. Immunol. 162*:2368-2374. The American Association of Immunologists (1999).

Speiser, D.E., et al., "In vivo activation of melanoma-specific $CD8^+$ T cells by endogenous tumor antigen and peptide vaccines. A comparison to virus-specific T cells," *Eur. J. Immunol. 32*:731-741, WILEY-VCH Verlag GmbH (Mar. 2002).

Steinman, R.M., "Dendritic cells and immune-based therapies," *Exp. Hematol. 24*:859-862, Elsevier Science Inc. (1996).

Storni, T., et al., "Critical Role for Activation of Antigen-Presenting Cells in Priming of Cytotoxic T Cell Responses After Vaccination with Virus-Like Particles," *J. Immunol. 168*:2880-2886, The American Association of Immunologists (Mar. 2002).

Sun, Y., et. al., "Identification of a New HLA-A*0201-Restricted T-Cell Epitope from the Tyrosinase-Related Protein 2 (TRP2) Melanoma Antigen," *Int. J. Cancer 87*:399-404, Wiley-Liss Inc. (2000).

Taylor, K.M., et al., "Position-Dependent Processing of Peptides Presented on the Surface of Cowpea Mosaic Virus," *Biol. Chem. 380*:387-392, Walter de Gruyter (1999).

Toes, R.E., et al., "Discrete Cleavage Motifs of Constitutive and Immunoproteasomes Revealed by Quantitative Analysis of Cleavage Products," *J. Exp. Med. 194*:1-12, The Rockefeller University Press (2001).

Torrence, P.F., "Preparation of a Synthetic Polynucleotide Interferon Inducer," *Meth. Enzymol. 78*:326-331, Academic Press, Inc. (1981).

Touzé, A., et al., "Gene transfer using human polyomavirus BK virus-like particles expressed in insect cells," *J. Gen. Virol. 82*:3005-3009, Society for General Microbiology (2001).

Valmori, D., et al., "Enhanced Generation of Specific Tumor-Reactive CTL In Vitro by Selected Melan-A/MART-1 Immunodominant Peptide Analogues," *J. Immunol. 160*:1750-1758,The American Association of Immunologists (1998).

Valmori, D., et al., "Diversity of the Fine Specificity Displayed by HLA-A*0201-Restricted CTL Specific for the Immunodominant Melan-A/MART-1 Antigenic Peptide," *J. Immunol. 161*:6956-6962, The American Association of Immunologists (1998).

van Schooten, W.C.A., et al., "Biological properties of dendritic cells: implications to their use in the treatment of cancer ," *Mol. Med. Today 255*:254-260, Elsevier Science (1997).

Vasiljeva, I., et al., "Mosaic Qβ coats as a new presentation model," *FEBS Lett 431*:7-11, Elsevier Science B.V. (1998).

Witte, L., et al., "Monoclonal antibodies targeting the VEGF receptor-2 (Flk1/KDR) as an anti-angiogenic therapeutic strategy," *Cancer Metastasis Rev. 17*:155-161, Kluwer Academic Publishers (1998).

Yuan, T.T., et al., "Subtype-Independent Immature Secretion and Subtype-Dependent Replication Deficiency of a Highly Frequent, Naturally Occurring Mutation of Human Hepatitis B Virus Core Antigen." *J. Virol.* 73:10122-10128, American Society for Microbiology (1999).

Zarour, H.M., et.al., "NY-ESO-1 119-143 Is a Promiscuous Major Histocompatibility Complex Class II T-Helper Epitope Recognized by Th1- and Th2-Type Tumor-reactive $CD4^+$ T Cells," *Cancer Res. 62*:213-218, American Association for Cancer Research (Jan. 2002).

Zhou, S. and Standring, D.N., "Cys Residues of the Hepatitis B Virus Capsid Protein Are Not Essential for the Assembly of Viral Core Particles but Can Influence Their Stability," *J. Virol*. 66:5393-5398, American Society for Microbiology (1992).

Dialog File 351, Accession No. 4796523, Derwent WPI English language abstract for EP 0 201 416 A1, cited as document AO1 on Form PTO-1449.

Allison (1994) Int J Technol Assess Health Care 10(1):107-20—Adjuvants and immune enhancement.

Azuma (1992) Vaccine 10(14):1000-6—Synthetic immunoadjuvants: application to non-specific host stimulation and potential of vaccine immunogenicity.

Bird (1987) Trends Genet. 3(12):342-347—CpG islands as gene markers in the vertebrate nucleus.

Branda (1993) Biochem Pharmacol 45(10):2037-43—Immune stimulation by an antisense oligomer complementary to the $_{rev}$ gene of HIV-1.

Cooper (Aug. 2004) Vaccine 22(23-24):3136-43—Safety and immunogenicity of CPG 7909 injection as an adjuvant to Fluarix influenza vaccine.

Francois (1988) Clin Immunol Immunopathol 48(3):297-306—Examination of the inhibitory and stimulatory effects of IFN-α, -β, and -γ on human B-cell proliferation induced by various B-cell mitogens.

Gavett (1995) J Exp Med 182(5):1527-36—Interleukin 12 inhibits antigen-induced airway hyperresponsiveness, inflammation, and Th2 cytokine expression in mice.

Gilkeson (1989) J Immunol 142(5):1482-6—Induction of anti-double stranded DNA antibodies in normal mice by immunization with bacterial DNA.

Gursel (2001) J Immunol 167(6):3324-8—Sterically stabilized cationic liposomes improve the uptake and immunostimulatory activity of CpG oligonucleotides.

Halperin (Jun. 2003) Vaccine 21(19-20):2461-7—A phase I study of the safety and immunogenicity of recombinant hepatitis B surface antigen co-administered with an immunostimulatory phosphorothioate oligonucleotide adjuvant.

Holt (1994) Lancet 344(8920):456-8—A potential vaccine strategy for asthma and allied atopic diseases during early childhood.

Hsu (1996) Nat Med 2(5):540-4—Immunoprophylaxis of allergen-induced immunoglobulin E synthesis and airway hyperresponsiveness in vivo by genetic immunization.

Joseph (Sep. 2002) Vaccine 20(27-28):3342-54—Liposomal immunostimulatory DNA sequence (ISS-ODN): an efficient parenteral and mucosal adjuvant for influenza and hepatitis B vaccines.

Kataoka (1992) Jpn J Cancer Res 83(3):244-7—Antitumor activity of synthetic oligonucleotides with sequences from cDNA encoding proteins of *Mycobacterium bovis* BCG.

Kline (1996) J. Invest Med 44(7):380A—CpG motif oligonucleotides are effective in prevention of eosinophilic inflammation in a murine model of asthma.

Kuramoto (1992) Cancer Immunol Immunother 34(5):283-8—Induction of T-cell-mediated immunity against MethA fibrosarcoma by intratumoral injections of a bacillus Calmette-Guérin nucleic acid fraction.

Lotz (1987) J Rheumatol 14(1):42-5—Effects of recombinant human interferons on rheumatoid arthritis B lymphocytes activated by Epstein-Barr virus.

McIntyre (1993) Antisense Res Dev 3(4):309-22—A sense phosphorothioate oligonucleotide directed to the initiation codon of transcription factor NF-κ B p65 causes sequence-specific immune stimulation.

Merritt (1965) J Immunol 94():416-22—Studies on the Adjuvant Action of Bacterial Endotoxins on Antibody Formation. VI. Enhancement of Antibody Formation by Nucleic Acids.

Messina (1991) J Immunol 147(6):1759-64—Stimulation of in vitro murine lymphocyte proliferation by bacterial DNA.

Messina (1993) Cell Immunol 147(1):148-57—The influence of DNA structure on the in vitro stimulation of murine lymphocytes by natural and synthetic polynucleotide antigens.

Mojcik (1993) Clin Immunol Immunopathol 67(2):130-6—Administration of a phosphorothioate oligonucleotide antisense to murine endogenous retroviral MCF *env* causes immune effects in vivo in a sequence-specific manner.

Nohria (1994) Biotherapy 7(3-4):261-9—Cytokines as potential vaccine adjuvants.

Pisetsky (1993) Mol Biol Rep 18(3):217-21—Stimulation of in vitro proliferation of murine lymphocytes by synthetic oligodeoxynucleotides.

Pisetsky (1994) Life Sci 54(2):101-7—Stimulation of murine lymphocyte proliferation by a phosphorothioate oligonucleotide with antisense activity for herpes simplex virus.

Raz (1996) Proc Natl Acad Sci U S A 93(10):5141-5—Preferential induction of a $Th_1$ immune response and inhibition of specific lgE antibody formation by plasmid DNA immunization.

Saiki (1988) Vaccine 6(3):238-44—Induction of tumoricidal macrophages and production of cytokines by synthetic muramyl dipeptide analogues.

Sato (1996) Science 273(5273):352-4—Immunostimulatory DNA sequences necessary for effective intradermal gene immunization.

Uhlmann (Mar. 2003) Curr Opin Drug Discov Devel 6(2):204-17—Recent advances in the development of immunostimulatory oligonucleotides.

Verthelyi (2001) J Immunol 166(4):2372-7—Human peripheral blood cells differentially recognize and respond to two distinct CPG motifs.

Verthelyi (Apr. 2004) AIDS 18(7):1003-8—CpG oligodeoxynucleotides improve the response to hepatitis B immunization in healthy and SIV-infected rhesus macaques.

Weiner (2000) Declaration of Dr. George Weiner Under 37 CFR § 1.32, submitted in U.S. Appl. No. 09/286,098, inventors Kreig et al., 9 pages.

Weiner (1997) Proc Natl Acad Sci U S A 94(20):10833-7—Immunostimulatory oligodeoxynucleotides containing the CpG motif are effective as immune adjuvants in tumor antigen immunization.

Yamamoto (1994) Antisense Res Dev 4(2):119-22—Ability of oligonucleotides with certain palindromes to induce interferon production and augment natural killer cell activity is associated with their base length.

Yamamoto (1994) Microbiol Immunol 38(10):831-6—Lipofection of synthetic oligodeoxyribonucleotide having a palindromic sequence of AACGTT to murine splenocytes enhances interferon production and natural killer activity.

* cited by examiner

SEQUENCE LISTING

```
<160> NUMBER OF SEQ ID NOS: 94

<210> SEQ ID NO 1
<211> LENGTH: 10
<212> TYPE: DNA
<213> ORGANISM: Artificial sequence
<220> FEATURE:
<223> OTHER INFORMATION: oligonucleotide ISS

<400> SEQUENCE: 1

gacgatcgtc                                                            10


<210> SEQ ID NO 2
<211> LENGTH: 19
<212> TYPE: DNA
<213> ORGANISM: Artificial Sequence
<220> FEATURE:
<223> OTHER INFORMATION: oligonucleotide G3-6
```

-continued

<400> SEQUENCE: 2
ggggacgatc gtcgggggg 19

<210> SEQ ID NO 3
<211> LENGTH: 20
<212> TYPE: DNA
<213> ORGANISM: Artificial Sequence
<220> FEATURE:
<223> OTHER INFORMATION: oligonucleotide G4-6

<400> SEQUENCE: 3
gggggacgat cgtcgggggg 20

<210> SEQ ID NO 4
<211> LENGTH: 21
<212> TYPE: DNA
<213> ORGANISM: Artificial sequence
<220> FEATURE:
<223> OTHER INFORMATION: oligonucleotide G5-6

<400> SEQUENCE: 4
ggggggacga tcgtcggggg g 21

<210> SEQ ID NO 5
<211> LENGTH: 22
<212> TYPE: DNA
<213> ORGANISM: Artificial sequence
<220> FEATURE:
<223> OTHER INFORMATION: oligonucleotide G6-6

<400> SEQUENCE: 5
gggggggacg atcgtcgggg gg 22

<210> SEQ ID NO 6
<211> LENGTH: 24
<212> TYPE: DNA
<213> ORGANISM: Artificial sequence
<220> FEATURE:
<223> OTHER INFORMATION: oligonucleotide G7-7

<400> SEQUENCE: 6
ggggggggac gatcgtcggg gggg 24

<210> SEQ ID NO 7
<211> LENGTH: 26
<212> TYPE: DNA
<213> ORGANISM: Artificial sequence
<220> FEATURE:
<223> OTHER INFORMATION: oligonucleotide G8-8

<400> SEQUENCE: 7
ggggggggga cgatcgtcgg gggggg 26

<210> SEQ ID NO 8
<211> LENGTH: 28
<212> TYPE: DNA
<213> ORGANISM: Artificial Sequence
<220> FEATURE:
<223> OTHER INFORMATION: oligonucleotide G9-9

<400> SEQUENCE: 8
gggggggggg acgatcgtcg gggggggg 28

-continued

<210> SEQ ID NO 9
<211> LENGTH: 30
<212> TYPE: DNA
<213> ORGANISM: Artificial sequence
<220> FEATURE:
<223> OTHER INFORMATION: oligonucleotide G6

<400> SEQUENCE: 9 gggggcgac gacgatcgtc gtcggggggg 30

<210> SEQ ID NO 10
<211> LENGTH: 132
<212> TYPE: PRT
<213> ORGANISM: Bacteriophage Q-beta

<400> SEQUENCE: 10

```
Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

<210> SEQ ID NO 11
<211> LENGTH: 328
<212> TYPE: PRT
<213> ORGANISM: Bacteriophage Q-beta

<400> SEQUENCE: 11

```
Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125
```

-continued

```
Leu Asn Pro Ala Tyr Trp Leu Leu Ile Ala Gly Gly Gly Ser Gly Ser
    130                 135                 140

Lys Pro Asp Pro Val Ile Pro Asp Pro Pro Ile Asp Pro Pro Pro Gly
145                 150                 155                 160

Thr Gly Lys Tyr Thr Cys Pro Phe Ala Ile Trp Ser Leu Glu Glu Val
                165                 170                 175

Tyr Glu Pro Pro Thr Lys Asn Arg Pro Trp Pro Ile Tyr Asn Ala Val
            180                 185                 190

Glu Leu Gln Pro Arg Glu Phe Asp Val Ala Leu Lys Asp Leu Leu Gly
        195                 200                 205

Asn Thr Lys Trp Arg Asp Trp Asp Ser Arg Leu Ser Tyr Thr Thr Phe
    210                 215                 220

Arg Gly Cys Arg Gly Asn Gly Tyr Ile Asp Leu Asp Ala Thr Tyr Leu
225                 230                 235                 240

Ala Thr Asp Gln Ala Met Arg Asp Gln Lys Tyr Asp Ile Arg Glu Gly
                245                 250                 255

Lys Lys Pro Gly Ala Phe Gly Asn Ile Glu Arg Phe Ile Tyr Leu Lys
            260                 265                 270

Ser Ile Asn Ala Tyr Cys Ser Leu Ser Asp Ile Ala Ala Tyr His Ala
        275                 280                 285

Asp Gly Val Ile Val Gly Phe Trp Arg Asp Pro Ser Ser Gly Gly Ala
    290                 295                 300

Ile Pro Phe Asp Phe Thr Lys Phe Asp Lys Thr Lys Cys Pro Ile Gln
305                 310                 315                 320

Ala Val Ile Val Val Pro Arg Ala
                325


<210> SEQ ID NO 12
<211> LENGTH: 362
<212> TYPE: PRT
<213> ORGANISM: BK virus

<400> SEQUENCE: 12

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Asp Asn Leu Arg
    50                  55                  60

Gly Tyr Ser Gln His Leu Ser Ala Glu Asn Ala Phe Glu Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
        115                 120                 125

Leu His Ala Gly Ser Gln Lys Val His Glu Asn Gly Gly Gly Lys Pro
    130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175
```

-continued

```
Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
        275                 280                 285

Ile Arg Leu Arg Lys Arg Ser Val Lys Asn Pro Tyr Pro Ile Ser Phe
    290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
            340                 345                 350

Arg Gln Gly Gln Leu Gln Thr Lys Met Val
        355                 360
```

<210> SEQ ID NO 13
<211> LENGTH: 130
<212> TYPE: PRT
<213> ORGANISM: Bacteriophage fr

<400> SEQUENCE: 13

```
Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130
```

<210> SEQ ID NO 14
<211> LENGTH: 130
<212> TYPE: PRT
<213> ORGANISM: Bacteriophage GA -continued

<400> SEQUENCE: 14

```
Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130
```

<210> SEQ ID NO 15
<211> LENGTH: 594
<212> TYPE: DNA
<213> ORGANISM: Artificial Sequence
<220> FEATURE:
<223> OTHER INFORMATION: HBcAg containing p33 from LCMV
<220> FEATURE:
<221> NAME/KEY: CDS
<222> LOCATION: (1)..(594)

<400> SEQUENCE: 15

```
atg gac att gac cct tat aaa gaa ttt gga gct act gtg gag tta ctc       48
Met Asp Ile Asp Pro Tyr Lys Glu Phe Gly Ala Thr Val Glu Leu Leu
1               5                   10                  15

tcg ttt ttg cct tct gac ttc ttt cct tcc gtc aga gat ctc cta gac       96
Ser Phe Leu Pro Ser Asp Phe Phe Pro Ser Val Arg Asp Leu Leu Asp
            20                  25                  30

acc gcc tca gct ctg tat cga gaa gcc tta gag tct cct gag cat tgc      144
Thr Ala Ser Ala Leu Tyr Arg Glu Ala Leu Glu Ser Pro Glu His Cys
        35                  40                  45

tca cct cac cat act gca ctc agg caa gcc att ctc tgc tgg ggg gaa      192
Ser Pro His His Thr Ala Leu Arg Gln Ala Ile Leu Cys Trp Gly Glu
    50                  55                  60

ttg atg act cta gct acc tgg gtg ggt aat aat ttg gaa gat cca gca      240
Leu Met Thr Leu Ala Thr Trp Val Gly Asn Asn Leu Glu Asp Pro Ala
65                  70                  75                  80

tcc agg gat cta gta gtc aat tat gtt aat act aac atg ggt tta aag      288
Ser Arg Asp Leu Val Val Asn Tyr Val Asn Thr Asn Met Gly Leu Lys
                85                  90                  95

atc agg caa cta ttg tgg ttt cat ata tct tgc ctt act ttt gga aga      336
Ile Arg Gln Leu Leu Trp Phe His Ile Ser Cys Leu Thr Phe Gly Arg
            100                 105                 110

gag act gta ctt gaa tat ttg gtc tct ttc gga gtg tgg att cgc act      384
Glu Thr Val Leu Glu Tyr Leu Val Ser Phe Gly Val Trp Ile Arg Thr
        115                 120                 125

cct cca gcc tat aga cca cca aat gcc cct atc tta tca aca ctt ccg      432
Pro Pro Ala Tyr Arg Pro Pro Asn Ala Pro Ile Leu Ser Thr Leu Pro
    130                 135                 140
```

-continued

```
gaa act act gtt gtt aga cga cgg gac cga ggc agg tcc cct aga aga      480
Glu Thr Thr Val Val Arg Arg Arg Asp Arg Gly Arg Ser Pro Arg Arg
145                 150                 155                 160

aga act ccc tcg cct cgc aga cgc aga tct caa tcg ccg cgt cgc aga      528
Arg Thr Pro Ser Pro Arg Arg Arg Arg Ser Gln Ser Pro Arg Arg Arg
                165                 170                 175

aga tct caa tct cgg gaa tct caa tgt ctt ctc ctt aaa gct gtt tac      576
Arg Ser Gln Ser Arg Glu Ser Gln Cys Leu Leu Leu Lys Ala Val Tyr
            180                 185                 190

aac ttc gct acc atg taa                                              594
Asn Phe Ala Thr Met
        195


<210> SEQ ID NO 16
<211> LENGTH: 197
<212> TYPE: PRT
<213> ORGANISM: Artificial Sequence
<220> FEATURE:
<223> OTHER INFORMATION: HBcAg containing p33 from LCMV

<400> SEQUENCE: 16

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys Leu Leu Leu Lys Ala Val Tyr
            180                 185                 190

Asn Phe Ala Thr Met
        195


<210> SEQ ID NO 17
<211> LENGTH: 246
<212> TYPE: DNA
<213> ORGANISM: Artificial Sequence
<220> FEATURE:
<223> OTHER INFORMATION: dsDNA fragment for packaging and stabilization
      of BKV

<400> SEQUENCE: 17

ggcggtggtg tcagatctac aatgatcgtc atcaccttgg tgatgctgaa gaagaaacag     60

tacacatcca ttcatcatgg tgtggtggag gttgacgccg ctgtcacccc agaggagcgc    120
```

-continued

```
cacctgtcca agatgcagca gaacggctac gaaaatccaa cctacaagtt ctttgagcag    180

atgcagaacg ctagctatcc atacgatgtc cctgattacg cctaacgcga attcgccagc    240

acagtg                                                               246


<210> SEQ ID NO 18
<211> LENGTH: 5
<212> TYPE: PRT
<213> ORGANISM: Artificial Sequence
<220> FEATURE:
<223> OTHER INFORMATION: GGKGG Linker

<400> SEQUENCE: 18

Gly Gly Lys Gly Gly
1               5


<210> SEQ ID NO 19
<211> LENGTH: 128
<212> TYPE: PRT
<213> ORGANISM: Bacteriophage PP7

<400> SEQUENCE: 19

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125


<210> SEQ ID NO 20
<211> LENGTH: 132
<212> TYPE: PRT
<213> ORGANISM: Bacteriophage Q-beta

<400> SEQUENCE: 20

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110
```

-continued

```
Ala Ala Leu Leu Ala Ser Pro Leu Leu Ile Asp Ala Ile Asp Gln Leu
        115                 120                 125

Asn Pro Ala Tyr
    130


<210> SEQ ID NO 21
<211> LENGTH: 132
<212> TYPE: PRT
<213> ORGANISM: Bacteriophage Q-beta

<400> SEQUENCE: 21

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 22
<211> LENGTH: 132
<212> TYPE: PRT
<213> ORGANISM: Bacteriophage Q-beta

<400> SEQUENCE: 22

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

-continued

```
<210> SEQ ID NO 23
<211> LENGTH: 132
<212> TYPE: PRT
<213> ORGANISM: Bacteriophage Q-beta

<400> SEQUENCE: 23

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 24
<211> LENGTH: 132
<212> TYPE: PRT
<213> ORGANISM: Bacteriophage Q-beta

<400> SEQUENCE: 24

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130


<210> SEQ ID NO 25
<211> LENGTH: 184
<212> TYPE: PRT
<213> ORGANISM: Hepatitis B virus
```

-continued

<400> SEQUENCE: 25

```
Met Asp Ile Asp Pro Tyr Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Arg Ser Gln Ser Pro Arg Arg Arg Arg
                165                 170                 175

Ser Gln Ser Arg Glu Ser Gln Cys
            180
```

<210> SEQ ID NO 26
<211> LENGTH: 213
<212> TYPE: PRT
<213> ORGANISM: Hepatitis B virus

<400> SEQUENCE: 26

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Asn
                85                  90                  95

Leu Ala Thr Trp Val Gly Gly Asn Leu Glu Asp Pro Val Ser Arg Asp
            100                 105                 110

Leu Val Val Gly Tyr Val Asn Thr Thr Val Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

-continued

```
Val Val Arg Arg Arg Gly Arg Ser Pro Arg Arg Arg Thr Pro Ser Pro
            180                 185                 190

Pro Arg Arg Arg Arg Ser Gln Ser Pro Arg Arg Arg Arg Ser Gln Ser
        195                 200                 205

Arg Glu Ser Gln Cys
    210


<210> SEQ ID NO 27
<211> LENGTH: 188
<212> TYPE: PRT
<213> ORGANISM: Hepatitis B virus

<400> SEQUENCE: 27

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Pro Ser Thr Asn Cys
            180                 185


<210> SEQ ID NO 28
<211> LENGTH: 185
<212> TYPE: PRT
<213> ORGANISM: Hepatitis B virus

<400> SEQUENCE: 28

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95
```

-continued

```
Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185


<210> SEQ ID NO 29
<211> LENGTH: 152
<212> TYPE: PRT
<213> ORGANISM: Hepatitis B virus

<400> SEQUENCE: 29

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val
145                 150


<210> SEQ ID NO 30
<211> LENGTH: 3635
<212> TYPE: DNA
<213> ORGANISM: Artificial Sequence
<220> FEATURE:
<223> OTHER INFORMATION: plasmid pAP283-58

<400> SEQUENCE: 30

cgagctcgcc cctggcttat cgaaattaat acgactcact atagggagac cggaattcga      60

gctcgcccgg ggatcctcta gaattttctg cgcacccatc ccgggtggcg cccaaagtga     120

ggaaaatcac atggcaaata agccaatgca accgatcaca tctacagcaa ataaaattgt     180

gtggtcggat ccaactcgtt tatcaactac attttcagca agtctgttac gccaacgtgt     240

taaagttggt atagccgaac tgaataatgt ttcaggtcaa tatgtatctg tttataagcg     300

tcctgcacct aaaccggaag gttgtgcaga tgcctgtgtc attatgccga atgaaaacca     360

atccattcgc acagtgattt cagggtcagc cgaaaacttg gctaccttaa aagcagaatg     420
```

-continued

```
ggaaactcac aaacgtaacg ttgacacact cttcgcgagc ggcaacgccg gtttgggttt    480
ccttgaccct actgcggcta tcgtatcgtc tgatactact gcttaagctt gtattctata    540
gtgtcaccta aatcgtatgt gtatgataca taaggttatg tattaattgt agccgcgttc    600
taacgacaat atgtacaagc ctaattgtgt agcatctggc ttactgaagc agaccctatc    660
atctctctcg taaactgccg tcagagtcgg tttggttgga cgaaccttct gagtttctgg    720
taacgccgtt ccgcaccccg gaaatggtca ccgaaccaat cagcagggtc atcgctagcc    780
agatcctcta cgccggacgc atcgtggccg gcatcaccgg cgcacacagt gcggttgctg    840
gcgcctatat cgccgacatc accgatgggg aagatcgggc tcgccacttc gggctcatga    900
gcgcttgttt cggcgtgggt atggtggcag gccccgtggc cgggggactg ttgggcgcca    960
tctccttgca tgcaccattc cttgcggcgg cggtgcttca acggcctcaa cctactactg   1020
ggctgcttcc taatgcagga gtcgcataag ggagagcgtc gatatggtgc actctcagta   1080
caatctgctc tgatgccgca tagttaagcc aactccgcta tcgctacgtg actgggtcat   1140
ggctgcgccc cgacacccgc caacacccgc tgacgcgccc tgacgggctt gtctgctccc   1200
ggcatccgct tacagacaag ctgtgaccgt ctccgggagc tgcatgtgtc agaggttttc   1260
accgtcatca ccgaaacgcg cgaggcagct tgaagacgaa agggcctcgt gatacgccta   1320
tttttatagg ttaatgtcat gataataatg gtttcttaga cgtcaggtgg cacttttcgg   1380
ggaaatgtgc gcggaacccc tatttgttta tttttctaaa tacattcaaa tatgtatccg   1440
ctcatgagac aataaccctg ataaatgctt caataatatt gaaaaaggaa gagtatgagt   1500
attcaacatt tccgtgtcgc ccttattccc ttttttgcgg cattttgcct tcctgttttt   1560
gctcacccag aaacgctggt gaaagtaaaa gatgctgaag atcagttggg tgcacgagtg   1620
ggttacatcg aactggatct caacagcggt aagatccttg agagttttcg ccccgaagaa   1680
cgttttccaa tgatgagcac ttttaaagtt ctgctatgtg gcgcggtatt atcccgtatt   1740
gacgccgggc aagagcaact cggtcgccgc atacactatt ctcagaatga cttggttgag   1800
tactcaccag tcacagaaaa gcatcttacg gatggcatga cagtaagaga attatgcagt   1860
gctgccataa ccatgagtga taacactgcg gccaacttac ttctgacaac gatcggagga   1920
ccgaaggagc taaccgcttt tttgcacaac atgggggatc atgtaactcg ccttgatcgt   1980
tgggaaccgg agctgaatga agccatacca aacgacgagc gtgacaccac gatgcctgta   2040
gcaatggcaa caacgttgcg caaactatta actggcgaac tacttactct agcttcccgg   2100
caacaattaa tagactggat ggaggcggat aaagttgcag gaccacttct gcgctcggcc   2160
cttccggctg gctggtttat tgctgataaa tctggagccg gtgagcgtgg gtctcgcggt   2220
atcattgcag cactggggcc agatggtaag ccctcccgta tcgtagttat ctacacgacg   2280
gggagtcagg caactatgga tgaacgaaat agacagatcg ctgagatagg tgcctcactg   2340
attaagcatt ggtaactgtc agaccaagtt tactcatata tactttagat tgatttaaaa   2400
cttcattttt aatttaaaag gatctaggtg aagatccttt ttgataatct catgaccaaa   2460
atcccttaac gtgagttttc gttccactga gcgtcagacc ccgtagaaaa gatcaaagga   2520
tcttcttgag atcctttttt tctgcgcgta atctgctgct tgcaaacaaa aaaaccaccg   2580
ctaccagcgg tggtttgttt gccggatcaa gagctaccaa ctctttttcc gaaggtaact   2640
ggcttcagca gagcgcagat accaaatact gtccttctag tgtagccgta gttaggccac   2700
cacttcaaga actctgtagc accgcctaca tacctcgctc tgctaatcct gttaccagtg   2760
gctgctgcca gtggcgataa gtcgtgtctt accgggttgg actcaagacg atagttaccg   2820
```

-continued

```
gataaggcgc agcggtcggg ctgaacgggg ggttcgtgca cacagcccag cttggagcga   2880

acgacctaca ccgaactgag atacctacag cgcgagcatt gagaaagcgc cacgcttccc   2940

gaagggagaa aggcggacag gtatccggta agcggcaggg tcggaacagg agagcgcacg   3000

agggagcttc caggggg aaa cgcctggtat ctttatagtc ctgtcgggtt tcgccacctc   3060

tgacttgagc gtcgattttt gtgatgctcg tcaggggggc ggagcctatg gaaaaacgcc   3120

agcaacgcgg cctttttacg gttcctggcc ttttgctggc cttttgctca catgttcttt   3180

cctgcgttat cccctgattc tgtggataac cgtattaccg cctttgagtg agctgatacc   3240

gctcgccgca gccgaacgac gagcgcagcg agtcagtgag cgaggaagcg gaagagcgcc   3300

caatacgcaa accgcctctc cccgcgcgtt ggccgattca ttaatgcagc tgtggtgtca   3360

tggtcggtga tcgccagggt gccgacgcgc atctcgactg catggtgcac caatgcttct   3420

ggcgtcaggc agccatcgga agctgtggta tggccgtgca ggtcgtaaat cactgcataa   3480

ttcgtgtcgc tcaaggcgca ctcccgttct ggataatgtt ttttgcgccg acatcataac   3540

ggttctggca aatattctga aatgagctgt tgacaattaa tcatcgaact agttaactag   3600

tacgcaagtt cacgtaaaaa gggtatcgcg gaatt                              3635
```

<210> SEQ ID NO 31
<211> LENGTH: 131
<212> TYPE: PRT
<213> ORGANISM: Artificial Sequence
<220> FEATURE:
<223> OTHER INFORMATION: AP205 coat protein

<400> SEQUENCE: 31

```
Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130
```

<210> SEQ ID NO 32
<211> LENGTH: 131
<212> TYPE: PRT
<213> ORGANISM: Artificial Sequence
<220> FEATURE:
<223> OTHER INFORMATION: AP205 coat protein -continued

<400> SEQUENCE: 32

```
Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130
```

<210> SEQ ID NO 33
<211> LENGTH: 3607
<212> TYPE: DNA
<213> ORGANISM: Artificial Sequence
<220> FEATURE:
<223> OTHER INFORMATION: plasmid pAP281-32

<400> SEQUENCE: 33

```
cgagctcgcc cctggcttat cgaaattaat acgactcact atagggagac cggaattcga     60

gctcgcccgg ggatcctcta gattaaccca acgcgtagga gtcaggccat ggcaaataag    120

acaatgcaac cgatcacatc tacagcaaat aaaattgtgt ggtcggatcc aactcgttta    180

tcaactacat tttcagcaag tctgttacgc caacgtgtta aagttggtat agccgaactg    240

aataatgttt caggtcaata tgtatctgtt tataagcgtc ctgcacctaa accgaaggtc    300

agatgcctgt gtcattatgc cgaatgaaaa ccaatccatt cgcacagtga tttcagggtc    360

agccgaaaac ttggctacct taaaagcaga atgggaaact cacaaacgta acgttgacac    420

actcttcgcg agcggcaacg ccggtttggg tttccttgac cctactgcgg ctatcgtatc    480

gtctgatact actgcttaag cttgtattct atagtgtcac ctaaatcgta tgtgtatgat    540

acataaggtt atgtattaat ggtagccgcg ttctaacgac aatatgtaca agcctaattg    600

tgtagcatct ggcttactga agcagaccct atcatctctc tcgtaaactg ccgtcagagt    660

cggttgggtt ggacagacct ctgagtttct ggtaacgccg ttccgcaccc cggaaatggt    720

caccgaacca ttcagcaggg tcatcgctag ccagatcctc tacgccggac gcatcgtggc    780

ccgcatcacc ggcgccacag gtgcggtgct ggcgcctata tcgccgacat caccgatggg    840

gaagatcggg ctcgccactt cgggctcatg atcgctggtt tccgcctggg tatggtggca    900

ggccccgtgg cccgggggac tgttgggcgc catctccttg catgcaccat tccttgcggc    960

ggcggtgctc aacggcctca acctactact gggctgcttc ctaatgcagg agtcgcataa   1020

gggagagcgt cgatatggtg cactctcagt acaatctgct ctgatgccgc atagttaagc   1080

caactccgct atcgctacgt gactgggtca tggctgcgcc ccgacacccg ccaacacccg   1140

ctgacgcgcc ctgacgggct tgtctgcttc cggcatccgc ttacagacaa gctgtgaccg   1200
```

-continued

```
tctccgggag ctgcatgtgt cagaggtttt caccgtcatc accgaaacgc gcgaggcagc   1260
ttgaagacga aagggcctcg tgatacgcct atttttatag gttaatgtca tgataataat   1320
ggtttcttag acgtcaggtg gcacttttcg gggaaatgtg cgcggacccc ctattggttt   1380
atttttctaa atacattcaa atatgtatcc gctcatgaga caataaccct gataaatgct   1440
tcaataatat tgaaaaagga agagtatgag tattcaacat ttccgtgtcg cccttattcc   1500
cttttttgcg gcattttgcc ttcctgtttt tgctcaccca gaaacgctgg tgaaagtaaa   1560
agatgctgaa gatcagttgg gtgcacgagt gggttacatc gaactggatc tcaacagcgg   1620
taagatcctt gagagttttc gccccgaaga acgttttcca atgatgagca cttttaaagt   1680
tctgctatgt gtcgcggtat tatcccgtat tgacgccggg caagagcaac tcggtcgccg   1740
catacactat tctcagaatg acttggtggt acctaccagt cacagaaaag catcttacgg   1800
atggcatgac agtaagagaa ttatgcagtg ctgccataac catgagtgat aacactgcgg   1860
ccaacttact tctgacaacg atcggaggac cgaaggagct aaccgctttt ttgcacaaca   1920
tgggggatca tgtaactcgc cttgatcgtt gggaaccgga gctgaatgaa gccataccaa   1980
acgacgagcg tgacaccacg atgcctgtac gaacggcaac aacgttgcgc aaactattaa   2040
ctggcgaact acttactcta gcttcccggc aacaattaat agactggatg gaggcggata   2100
aagttgcagg accacttctg cgctcggccc ttccggctgg ctggtttatt gctgataaat   2160
ctggagccgg tgagcgtggg tctcgcggta tcattgcagc actggggcca gatggtaagc   2220
cctcccgtat cgtagttatc tacacgacgg ggagtcaggc aactatggat gaacgaaata   2280
gacagatcgc tgagataggt gcctcactga ttaagcattg gtaactgtca gaccaagttt   2340
actcatatat actttagatt gatttaaaac ttcattttta atttaaaagg atctaggtga   2400
agatcctttt tgataatctc atgaccaaaa tcccttaacg tgagttttcg ttccactgag   2460
cggtcagacc ccgtagaaag atcaaaggat cttcttgaga tccttttttt ctgcgcgtaa   2520
tctgctgctt gcaaacaaaa aaaccaccgc taccagcggt ggtttgtttg ccggatcaag   2580
agctaccaac tctttttccg aaggtaactg gcttcagcag agcgcagata ccaaatactg   2640
tccttctagt gtagccgtag ttaggccacc acttcaagaa ctctgtagca ccgcctacat   2700
acctcgctct gctaatcctg ttaccagtgg ctgctgccag tggcgataag tcgtgtctta   2760
ccgggttgga ctcaagacga taggtaccgg ataaggcgca gcggtcgggc tgaacggggg   2820
gttcgtgcac acagcccagc ttggagcgaa cgacctacac cgaactgaga tacctacagc   2880
gcgagcattg agaaagcgcc acgcttcccg aagggagaaa ggcggacagg tatccggtaa   2940
gcggcagggt cggaacaaga gagcgcacga gggagcttcc agggggaaac gcctggtatc   3000
tttatagtcc tgtcgggttt cgccacctct gacttgagcg tcgatttttg tgatgctcgt   3060
caggggggcg gagcctatgg aaaaacgcca gcaacgcggc ctttttacgg ttcctggcct   3120
ttggctggcc ttttgctcac atgttctttc ctgcgttatc ccctgattct gtggataacc   3180
gtattaccgc ctttgagtga gctgataccg ctcgccgcag ccgaacgacc gacggcgcag   3240
cgagtcagtg agcgaggaag cggaagagcg cccaatacgc aaaccgcctc tccccgcgcg   3300
ttggccgatt cattaatgca gctgtggtgt catggtcggt gatcgccagg gtgccgacgc   3360
gcatctcgac tgcatggtgc accaatgctt ctggcgtcag gcagccatcg gaagctgtgg   3420
tatggccgtg caggtcgtaa atcactgcat aattcgtgtc gctcaaggcg cactcccgtt   3480
ctggataatg tttttgcgg cgacatcata acggttctgg caaatattct gaaatgagct   3540
```

-continued

```
ggtgacaatt aatcatcgaa ctagttaact agtacgcaag ttcacgtaaa aagggtatcg   3600

cggaatt                                                             3607


<210> SEQ ID NO 34
<211> LENGTH: 21
<212> TYPE: DNA
<213> ORGANISM: Artificial sequence
<220> FEATURE:
<223> OTHER INFORMATION: CyCpGpt

<400> SEQUENCE: 34

tccatgacgt tcctgaataa t                                               21


<210> SEQ ID NO 35
<211> LENGTH: 21
<212> TYPE: DNA
<213> ORGANISM: Artificial sequence
<220> FEATURE:
<223> OTHER INFORMATION: CyCpG

<400> SEQUENCE: 35

tccatgacgt tcctgaataa t                                               21


<210> SEQ ID NO 36
<211> LENGTH: 20
<212> TYPE: DNA
<213> ORGANISM: Artificial sequence
<220> FEATURE:
<223> OTHER INFORMATION: B-CpGpt

<400> SEQUENCE: 36

tccatgacgt tcctgacgtt                                                 20


<210> SEQ ID NO 37
<211> LENGTH: 20
<212> TYPE: DNA
<213> ORGANISM: Artificial sequence
<220> FEATURE:
<223> OTHER INFORMATION: B-CpG

<400> SEQUENCE: 37

tccatgacgt tcctgacgtt                                                 20


<210> SEQ ID NO 38
<211> LENGTH: 19
<212> TYPE: DNA
<213> ORGANISM: Artificial sequence
<220> FEATURE:
<223> OTHER INFORMATION: NKCpGpt

<400> SEQUENCE: 38

ggggtcaacg ttgaggggg                                                  19


<210> SEQ ID NO 39
<211> LENGTH: 19
<212> TYPE: DNA
<213> ORGANISM: Artificial sequence
<220> FEATURE:
<223> OTHER INFORMATION: NKCpG

<400> SEQUENCE: 39

ggggtcaacg ttgaggggg                                                  19
```

-continued

<210> SEQ ID NO 40
<211> LENGTH: 21
<212> TYPE: DNA
<213> ORGANISM: Artificial sequence
<220> FEATURE:
<223> OTHER INFORMATION: CyCpG-rev-pt

<400> SEQUENCE: 40
attattcagg aacgtcatgg a 21

<210> SEQ ID NO 41
<211> LENGTH: 30
<212> TYPE: DNA
<213> ORGANISM: Artificial sequence
<220> FEATURE:
<223> OTHER INFORMATION: g10gacga-PO (G10-PO)

<400> SEQUENCE: 41
gggggggggg gacgatcgtc gggggggggg 30

<210> SEQ ID NO 42
<211> LENGTH: 30
<212> TYPE: DNA
<213> ORGANISM: Artificial sequence
<220> FEATURE:
<223> OTHER INFORMATION: g10gacga-PS

<400> SEQUENCE: 42
gggggggggg gacgatcgtc gggggggggg 30

<210> SEQ ID NO 43
<211> LENGTH: 62
<212> TYPE: DNA
<213> ORGANISM: Artificial sequence
<220> FEATURE:
<223> OTHER INFORMATION: (CPG) 20OpA

<400> SEQUENCE: 43
cgcgcgcgcg cgcgcgcgcg cgcgcgcgcg cgcgcgcgcg aaatgcatgt caaagacagc 60
at 62

<210> SEQ ID NO 44
<211> LENGTH: 61
<212> TYPE: DNA
<213> ORGANISM: Artificial sequence
<220> FEATURE:
<223> OTHER INFORMATION: Cy (CpG) 20

<400> SEQUENCE: 44
tccatgacgt tcctgaataa tcgcgcgcgc gcgcgcgcgc gcgcgcgcgc gcgcgcgcgc 60
g 61

<210> SEQ ID NO 45
<211> LENGTH: 83
<212> TYPE: DNA
<213> ORGANISM: Artificial sequence
<220> FEATURE:
<223> OTHER INFORMATION: Cy (CpG) 20-OpA

<400> SEQUENCE: 45
tccatgacgt tcctgaataa tcgcgcgcgc gcgcgcgcgc gcgcgcgcgc gcgcgcgcgc 60
gaaatgcatg tcaaagacag cat 83

-continued

<210> SEQ ID NO 46
<211> LENGTH: 43
<212> TYPE: DNA
<213> ORGANISM: Artificial sequence
<220> FEATURE:
<223> OTHER INFORMATION: CyOpA

<400> SEQUENCE: 46
tccatgacgt tcctgaataa taaatgcatg tcaaagacag cat 43

<210> SEQ ID NO 47
<211> LENGTH: 63
<212> TYPE: DNA
<213> ORGANISM: Artificial sequence
<220> FEATURE:
<223> OTHER INFORMATION: CyCyCy

<400> SEQUENCE: 47
tccatgacgt tcctgaataa ttccatgacg ttcctgaata attccatgac gttcctgaat 60
aat 63

<210> SEQ ID NO 48
<211> LENGTH: 150
<212> TYPE: DNA
<213> ORGANISM: Artificial sequence
<220> FEATURE:
<223> OTHER INFORMATION: Cy150-1

<400> SEQUENCE: 48
tccatgacgt tcctgaataa ttccatgacg ttcctgaata attccatgac gttcctgaat 60
aattggatga cgttggtgaa taattccatg acgttcctga ataattccat gacgttcctg 120
aataattcca tgacgttcct gaataattcc 150

<210> SEQ ID NO 49
<211> LENGTH: 253
<212> TYPE: DNA
<213> ORGANISM: Artificial sequence
<220> FEATURE:
<223> OTHER INFORMATION: dsCyCpG-253

<400> SEQUENCE: 49
ctagaactag tggatccccc gggctgcagg aattcgattc atgacttcct gaataattcc 60
atgacgttgg tgaataattc catgacgttc ctgaataatt ccatgacgtt cctgaataat 120
tccatgacgt tcctgaataa ttccatgacg ttcctgaata attccatgac gttcctgaat 180
aattccatga cgttcctgaa taattccatg acgttcctga aaattccaat caagcttatc 240
gataccgtcg acc 253

<210> SEQ ID NO 50
<211> LENGTH: 10
<212> TYPE: PRT
<213> ORGANISM: Artificial sequence
<220> FEATURE:
<223> OTHER INFORMATION: Melan A 26-35 A/L

<400> SEQUENCE: 50

Glu Leu Ala Gly Ile Gly Ile Leu Thr Val
1 5 10

<210> SEQ ID NO 51
<211> LENGTH: 20
<212> TYPE: PRT
<213> ORGANISM: Artificial sequence -continued
<220> FEATURE:
<223> OTHER INFORMATION: Melan A 16-35 A/L

<400> SEQUENCE: 51

Gly His Gly His Ser Tyr Thr Thr Ala Glu Glu Leu Ala Gly Ile Gly
1 5 10 15

Ile Leu Thr Val
20

<210> SEQ ID NO 52
<211> LENGTH: 21
<212> TYPE: PRT
<213> ORGANISM: Artificial sequence
<220> FEATURE:
<223> OTHER INFORMATION: MelanA 20-40 A/L

<400> SEQUENCE: 52

Ser Tyr Thr Thr Ala Glu Glu Leu Ala Gly Ile Gly Ile Leu Thr Val
1 5 10 15

Ile Leu Gly Val Leu
20

<210> SEQ ID NO 53
<211> LENGTH: 14
<212> TYPE: PRT
<213> ORGANISM: Artificial Sequence
<220> FEATURE:
<223> OTHER INFORMATION: MelanA 26-40 A/L

<400> SEQUENCE: 53

Glu Leu Ala Gly Ile Gly Ile Leu Thr Val Ile Leu Gly Val
1 5 10

<210> SEQ ID NO 54
<211> LENGTH: 21
<212> TYPE: PRT
<213> ORGANISM: Artificial Sequence
<220> FEATURE:
<223> OTHER INFORMATION: MelanA 16-35

<400> SEQUENCE: 54

Cys Gly His Gly His Ser Tyr Thr Thr Ala Glu Glu Ala Ala Gly Ile
1 5 10 15

Gly Ile Leu Thr Val
20

<210> SEQ ID NO 55
<211> LENGTH: 21
<212> TYPE: PRT
<213> ORGANISM: Artificial sequence
<220> FEATURE:
<223> OTHER INFORMATION: MelanA 16-35 A/L

<400> SEQUENCE: 55

Cys Gly His Gly His Ser Tyr Thr Thr Ala Glu Glu Leu Ala Gly Ile
1 5 10 15

Gly Ile Leu Thr Val
20

<210> SEQ ID NO 56
<211> LENGTH: 13
<212> TYPE: PRT
<213> ORGANISM: Artificial Sequence
<220> FEATURE:
<223> OTHER INFORMATION: MelanA 26-35

-continued

<400> SEQUENCE: 56

Cys Gly Gly Glu Ala Ala Gly Ile Gly Ile Leu Thr Val
1 5 10

<210> SEQ ID NO 57
<211> LENGTH: 13
<212> TYPE: PRT
<213> ORGANISM: Artificial Sequence
<220> FEATURE:
<223> OTHER INFORMATION: MelanA 26-35 A/L

<400> SEQUENCE: 57

Cys Gly Gly Glu Leu Ala Gly Ile Gly Ile Leu Thr Val
1 5 10

<210> SEQ ID NO 58
<211> LENGTH: 22
<212> TYPE: PRT
<213> ORGANISM: Artificial sequence
<220> FEATURE:
<223> OTHER INFORMATION: MelanA 20-40 A/L

<400> SEQUENCE: 58

Cys Ser Tyr Thr Thr Ala Glu Glu Leu Ala Gly Ile Gly Ile Leu Thr
1 5 10 15

Val Ile Leu Gly Val Leu
20

<210> SEQ ID NO 59
<211> LENGTH: 18
<212> TYPE: PRT
<213> ORGANISM: Artificial sequence
<220> FEATURE:
<223> OTHER INFORMATION: MelanA 26-40 A/L

<400> SEQUENCE: 59

Cys Gly Gly Glu Leu Ala Gly Ile Gly Ile Leu Thr Val Ile Leu Gly
1 5 10 15

Val Leu

<210> SEQ ID NO 60
<211> LENGTH: 13
<212> TYPE: PRT
<213> ORGANISM: Artificial sequence
<220> FEATURE:
<223> OTHER INFORMATION: MelanA 26-35-C

<400> SEQUENCE: 60

Glu Leu Ala Gly Ile Gly Ile Leu Thr Val Gly Gly Cys
1 5 10

<210> SEQ ID NO 61
<211> LENGTH: 35
<212> TYPE: DNA
<213> ORGANISM: Artificial Sequence
<220> FEATURE:
<223> OTHER INFORMATION: sequence of vector pAb185

<400> SEQUENCE: 61
tctagattaa cccaacgcgt aggagtcagg ccatg 35

<210> SEQ ID NO 62
<211> LENGTH: 9
<212> TYPE: PRT
<213> ORGANISM: Artificial Sequence -continued
<220> FEATURE:
<223> OTHER INFORMATION: N terminal glycine serine linkers
<220> FEATURE:
<221> NAME/KEY: REPEAT
<222> LOCATION: (1)..(1)
<223> OTHER INFORMATION: Glycine can be repeated from zero to five times
<220> FEATURE:
<221> NAME/KEY: REPEAT
<222> LOCATION: (3)..(3)
<223> OTHER INFORMATION: Glycine can be repeated from zero to ten times
<220> FEATURE:
<221> NAME/KEY: REPEAT
<222> LOCATION: (4)..(4)
<223> OTHER INFORMATION: Serine can be repeated from zero to two times
<220> FEATURE:
<221> NAME/KEY: REPEAT
<222> LOCATION: (5)..(9)
<223> OTHER INFORMATION: These residues can be repeated from zero to three times as a group

<400> SEQUENCE: 62

Gly Cys Gly Ser Gly Gly Gly Gly Ser
1               5

<210> SEQ ID NO 63
<211> LENGTH: 10
<212> TYPE: PRT
<213> ORGANISM: Artificial Sequence
<220> FEATURE:
<223> OTHER INFORMATION: C terminal glycine serine linkers
<220> FEATURE:
<221> NAME/KEY: REPEAT
<222> LOCATION: (1)..(1)
<223> OTHER INFORMATION: Glycine can be repeated from zero to ten times
<220> FEATURE:
<221> NAME/KEY: REPEAT
<222> LOCATION: (2)..(2)
<223> OTHER INFORMATION: Serine can be repeated from zero to two times
<220> FEATURE:
<221> NAME/KEY: REPEAT
<222> LOCATION: (3)..(7)
<223> OTHER INFORMATION: These residues can be repeated from zero to three times as a group
<220> FEATURE:
<221> NAME/KEY: REPEAT
<222> LOCATION: (8)..(8)
<223> OTHER INFORMATION: Glycine can be repeated from zero to eight times
<220> FEATURE:
<221> NAME/KEY: REPEAT
<222> LOCATION: (10)..(10)
<223> OTHER INFORMATION: Glycine can be repeated from zero to five times

<400> SEQUENCE: 63

Gly Ser Gly Gly Gly Gly Ser Gly Cys Gly
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Glycine serine linker

<400> SEQUENCE: 64

Gly Gly Gly Gly Ser
1               5

<210> SEQ ID NO 65
<211> LENGTH: 10
<212> TYPE: PRT
<213> ORGANISM: Artificial Sequence -continued
<220> FEATURE:
<223> OTHER INFORMATION: N-terminal gamma1

<400> SEQUENCE: 65

Cys Gly Asp Lys Thr His Thr Ser Pro Pro
1 5 10

<210> SEQ ID NO 66
<211> LENGTH: 10
<212> TYPE: PRT
<213> ORGANISM: Artificial Sequence
<220> FEATURE:
<223> OTHER INFORMATION: C-terminal gamma 1

<400> SEQUENCE: 66

Asp Lys Thr His Thr Ser Pro Pro Cys Gly
1 5 10

<210> SEQ ID NO 67
<211> LENGTH: 17
<212> TYPE: PRT
<213> ORGANISM: Artificial Sequence
<220> FEATURE:
<223> OTHER INFORMATION: N-terminal gamma 3

<400> SEQUENCE: 67

Cys Gly Gly Pro Lys Pro Ser Thr Pro Pro Gly Ser Ser Gly Gly Ala
1 5 10 15

Pro

<210> SEQ ID NO 68
<211> LENGTH: 18
<212> TYPE: PRT
<213> ORGANISM: Artificial Sequence
<220> FEATURE:
<223> OTHER INFORMATION: C-terminal gamma 3

<400> SEQUENCE: 68

Pro Lys Pro Ser Thr Pro Pro Gly Ser Ser Gly Gly Ala Pro Gly Gly
1 5 10 15

Cys Gly

<210> SEQ ID NO 69
<211> LENGTH: 6
<212> TYPE: PRT
<213> ORGANISM: Artificial Sequence
<220> FEATURE:
<223> OTHER INFORMATION: N-terminal glycine linker

<400> SEQUENCE: 69

Gly Cys Gly Gly Gly Gly
1 5

<210> SEQ ID NO 70
<211> LENGTH: 6
<212> TYPE: PRT
<213> ORGANISM: Artificial Sequence
<220> FEATURE:
<223> OTHER INFORMATION: C-terminal glycine linker

<400> SEQUENCE: 70

Gly Gly Gly Gly Cys Gly
1 5

-continued

<210> SEQ ID NO 71
<211> LENGTH: 6
<212> TYPE: PRT
<213> ORGANISM: Artificial Sequence
<220> FEATURE:
<223> OTHER INFORMATION: C-terminal glycine-lysine linker

<400> SEQUENCE: 71

Gly Gly Lys Lys Gly Cys
1               5

<210> SEQ ID NO 72
<211> LENGTH: 6
<212> TYPE: PRT
<213> ORGANISM: Artificial Sequence
<220> FEATURE:
<223> OTHER INFORMATION: N-terminal glycine-lysine linker

<400> SEQUENCE: 72

Cys Gly Lys Lys Gly Gly
1               5

<210> SEQ ID NO 73
<211> LENGTH: 6
<212> TYPE: PRT
<213> ORGANISM: Artificial Sequence
<220> FEATURE:
<223> OTHER INFORMATION: N-terminal linker 1

<400> SEQUENCE: 73

Cys Gly Lys Lys Gly Gly
1               5

<210> SEQ ID NO 74
<211> LENGTH: 6
<212> TYPE: PRT
<213> ORGANISM: Artificial Sequence
<220> FEATURE:
<223> OTHER INFORMATION: N-terminal linker 2

<400> SEQUENCE: 74

Cys Gly Asp Glu Gly Gly
1               5

<210> SEQ ID NO 75
<211> LENGTH: 6
<212> TYPE: PRT
<213> ORGANISM: Artificial Sequence
<220> FEATURE:
<223> OTHER INFORMATION: C-terminal liker

<400> SEQUENCE: 75

Gly Gly Lys Lys Gly Cys
1               5

<210> SEQ ID NO 76
<211> LENGTH: 6
<212> TYPE: PRT
<213> ORGANISM: Artificial Sequence
<220> FEATURE:
<223> OTHER INFORMATION: C-terminal linker 2

<400> SEQUENCE: 76

Gly Gly Glu Asp Gly Cys
1               5

-continued

```
<210> SEQ ID NO 77
<211> LENGTH: 4
<212> TYPE: PRT
<213> ORGANISM: Artificial Sequence
<220> FEATURE:
<223> OTHER INFORMATION: C-terminal linker 3

<400> SEQUENCE: 77

Gly Gly Cys Gly
1


<210> SEQ ID NO 78
<211> LENGTH: 10
<212> TYPE: PRT
<213> ORGANISM: Homo sapiens

<400> SEQUENCE: 78

Glu Ala Ala Gly Ile Gly Ile Leu Thr Val
1               5                   10


<210> SEQ ID NO 79
<211> LENGTH: 9
<212> TYPE: PRT
<213> ORGANISM: Homo sapiens

<400> SEQUENCE: 79

Ala Ala Gly Ile Gly Ile Leu Thr Val
1               5


<210> SEQ ID NO 80
<211> LENGTH: 9
<212> TYPE: PRT
<213> ORGANISM: Homo sapiens

<400> SEQUENCE: 80

Lys Ala Val Tyr Asn Phe Ala Thr Met
1               5


<210> SEQ ID NO 81
<211> LENGTH: 12
<212> TYPE: PRT
<213> ORGANISM: Homo sapiens

<400> SEQUENCE: 81

Cys Gly Gly Lys Ala Val Tyr Asn Phe Ala Thr Met
1               5                   10


<210> SEQ ID NO 82
<211> LENGTH: 12
<212> TYPE: PRT
<213> ORGANISM: Homo sapiens

<400> SEQUENCE: 82

Lys Ala Val Tyr Asn Phe Ala Thr Met Gly Gly Cys
1               5                   10


<210> SEQ ID NO 83
<211> LENGTH: 18
<212> TYPE: PRT
<213> ORGANISM: Homo sapiens

<400> SEQUENCE: 83

Cys Gly Gly Gly Ser Glu Glu Ile Arg Ser Leu Tyr Asn Thr Val Ala
1               5                   10                  15

Thr Leu
```

-continued

<210> SEQ ID NO 84
<211> LENGTH: 9
<212> TYPE: PRT
<213> ORGANISM: Homo sapiens

<400> SEQUENCE: 84

Leu Ala Gly Ile Gly Ile Leu Thr Val
1               5

<210> SEQ ID NO 85
<211> LENGTH: 9
<212> TYPE: PRT
<213> ORGANISM: Homo sapiens

<400> SEQUENCE: 85

Met Ala Gly Ile Gly Ile Leu Thr Val
1               5

<210> SEQ ID NO 86
<211> LENGTH: 10
<212> TYPE: PRT
<213> ORGANISM: Homo sapiens

<400> SEQUENCE: 86

Glu Ala Met Gly Ile Gly Ile Leu Thr Val
1               5                   10

<210> SEQ ID NO 87
<211> LENGTH: 10
<212> TYPE: PRT
<213> ORGANISM: Homo sapiens

<400> SEQUENCE: 87

Glu Met Ala Gly Ile Gly Ile Leu Thr Val
1               5                   10

<210> SEQ ID NO 88
<211> LENGTH: 10
<212> TYPE: PRT
<213> ORGANISM: Homo sapiens

<400> SEQUENCE: 88

Tyr Ala Ala Gly Ile Gly Ile Leu Thr Val
1               5                   10

<210> SEQ ID NO 89
<211> LENGTH: 10
<212> TYPE: PRT
<213> ORGANISM: Homo sapiens

<400> SEQUENCE: 89

Phe Ala Ala Gly Ile Gly Ile Leu Thr Val
1               5                   10

<210> SEQ ID NO 90
<211> LENGTH: 9
<212> TYPE: PRT
<213> ORGANISM: Homo sapiens

<400> SEQUENCE: 90

Leu Pro Tyr Leu Gly Trp Leu Val Phe
1               5

-continued

<210> SEQ ID NO 91
<211> LENGTH: 118
<212> TYPE: PRT
<213> ORGANISM: homo sapiens

<400> SEQUENCE: 91

```
Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115
```

<210> SEQ ID NO 92
<211> LENGTH: 16
<212> TYPE: PRT
<213> ORGANISM: Artificial Sequence
<220> FEATURE:
<223> OTHER INFORMATION: CSPKSL-MelanA 26-35 A/L

<400> SEQUENCE: 92

```
Cys Ser Pro Lys Ser Leu Glu Leu Ala Gly Ile Gly Ile Leu Thr Val
1               5                   10                  15
```

<210> SEQ ID NO 93
<211> LENGTH: 18
<212> TYPE: PRT
<213> ORGANISM: Artificial Sequence
<220> FEATURE:
<223> OTHER INFORMATION: MelanA 26-40-C A/L

<400> SEQUENCE: 93

```
Glu Leu Ala Gly Ile Gly Ile Leu Thr Val Ile Leu Gly Val Leu Gly
1               5                   10                  15

Gly Cys
```

<210> SEQ ID NO 94
<211> LENGTH: 118
<212> TYPE: PRT
<213> ORGANISM: Artificial Sequence
<220> FEATURE:
<223> OTHER INFORMATION: MelanA 1-118 A/L

<400> SEQUENCE: 94

```
Met Pro Arg Glu Asp Ala His Phe Ile Tyr Gly Tyr Pro Lys Lys Gly
1               5                   10                  15

His Gly His Ser Tyr Thr Thr Ala Glu Glu Leu Ala Gly Ile Gly Ile
            20                  25                  30

Leu Thr Val Ile Leu Gly Val Leu Leu Leu Ile Gly Cys Trp Tyr Cys
        35                  40                  45
```

-continued

```
Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115
```

MELAN-A- CARRIER CONJUGATES

CROSS-REFERENCE TO RELATED APPLICATIONS

This application is the U.S. National Phase of International Application PCT/EP2004/003164, international filing date of Mar. 25, 2004, and claims the benefit of U.S. Provisional Application No. 60/457,348, filed Mar. 26, 2003, which is hereby incorporated by reference in its entirety.

BACKGROUND OF THE INVENTION

1. Field of the Invention

The present invention is related to the fields of vaccinology, immunology and medicine. The invention provides compositions and methods for enhancing immunological responses against MelanA peptide analogues which are coupled, fused or attached otherwise to virus-like particles (VLPs) by binding, preferably by packaging immunostimulatory substances, in particular immunostimulatory nucleic acids, and even more particular oligonucleotides containing at least one non-methylated CpG sequence, into the VLPs. The invention can be used to induce strong and sustained T cell responses particularly useful for the treatment of tumors.

2. Related Art

The essence of the immune system is built on two separate foundation pillars: one is specific or adaptive immunity which is characterized by relatively slow response-kinetics and the ability to remember; the other is non-specific or innate immunity exhibiting rapid response-kinetics but lacking memory.

It is well established that the administration of purified proteins alone is usually not sufficient to elicit a strong immune response; isolated antigen generally must be given together with helper substances called adjuvants. Within these adjuvants, the administered antigen is protected against rapid degradation, and the adjuvant provides an extended release of a low level of antigen.

Unlike isolated proteins, viruses induce prompt and efficient immune responses in the absence of any adjuvants both with and without T-cell help (Bachmann & Zinkernagel, Ann. Rev. Immunol. 15:235-270 (1997)). Many viruses exhibit a quasi-crystalline surface that displays a regular array of epitopes which efficiently crosslinks epitope-specific immunoglobulins on B cells (Bachmann & Zinkernagel, Immunol. Today 17:553-558 (1996)). Viral structure is even linked to the generation of anti-antibodies in autoimmune disease and as a part of the natural response to pathogens (see Fehr, T., et al., J. Exp. Med. 185:1785-1792 (1997)). Thus, antigens on viral particles that are organized in an ordered and repetitive array are highly immunogenic since they can directly activate B cells and induce the generation of a cytotoxic T cell response, another crucial arm of the immune system.

Viral particles as antigens exhibit two advantages over their isolated components: (1) due to their highly repetitive surface structure, they are able to directly activate B cells, leading to high antibody titers and long-lasting B cell memory; and (2) viral particles, but not soluble proteins, have the potential to induce a cytotoxic T cell response, even if the viruses are non-infectious and adjuvants are absent.

In addition, DNA rich in non-methylated CG motifs (CpG), as present in bacteria and most non-vertebrates, exhibits a potent stimulatory activity on B cells, dendritic cells and other APC's in vitro as well as in vivo. Although bacterial DNA is immunostimulatory across many vertebrate species, the individual CpG motifs may differ. In fact, CpG motifs that stimulate mouse immune cells may not necessarily stimulate human immune cells and vice versa. In addition, immunostimulatory CpG-oligodeoxynucleotides induce strong side effects by causing extramedullary hemopoiesis accompanied by splenomegaly and lymphadenopathy in mice (Sparwasser et al., J. Immunol. (1999), 162:2368-74 and Example 18).

There have been remarkable advances made in vaccination strategies recently, yet there remains a need for improvement on existing strategies. In particular, there remains a need in the art for the development of new and improved vaccines that promote a strong CTL immune response and anti-pathogenic protection as efficiently as natural pathogens in the absence of generalized activation of APCs and other cells.

Melanomas are aggressive, frequently metastatic tumors derived from either melanocytes or melanocyte related nevus cells. Melanomas make up approximately three percent of all skin cancers and the worldwide increase in melanoma is unsurpassed by any other neoplasm with the exception of lung cancer in women. Even when melanoma is apparently localized to the skin, up to 30% of the patients will develop systemic metastasis and the majority will die. In the past decade immunotherapy and gene therapy have emerged as new and promising methods for treating melanoma, for example, treatment of Melanoma patients with the Melan A/MART-1 peptide with or without adjuvants. These Strategies are usually of limited success. Moreover, most of the studies did not measure directly the ex vivo CTL response with MHC class I multimers but rather used CTL cultures and stimulated them for several weeks before they could eventually measure a MelanA specific CTL response. In general, peptides are not immunogenic by itself and have a very short half life.

Another way of immunotherapy is the loading of dendritic cells with either the MelanA/MART-1 Peptide, or transfection of dendritic cells with MelanA/MART-1-RNA and re-injection onto patients. Drawback of this procedure is the purification and incubation of autologous dendritic cells from each individual patient for several days with cytokines in vitro. This is very delicate because the dendritic cells have to be in the right state of maturation for being immunogenic and not tolerogenic that could lead to T cells no responding to the tumor anymore.

Another approach from Dudley, M. E. (Science. 2002 Oct 25;298(5594):850-4) the is isolation of MelanA-specific T cells from autologous tumor-material of patients, in vitro cultivation and expansion and reinjection into the donor. As the aforementioned approach, a specific vaccine needs to produced separately for each individual patient and is therefore not the most efficient therapy.

Characterization of potent melanoma vaccines is, therefore, important for the development of new strategies for cancer immunotherapy, in particular for melanoma.

SUMMARY OF THE INVENTION

This invention is based on the finding that particular human MelanA peptide analogues when bound to a core particle having a structure with an inherent repetitive organization, and hereby in particular to virus-like-particles (VLPs) and subunits of VLPs, respectively, which VLPs are packaged with immunostimulatory substances (ISSs) such as DNA oligonucleotides, represent potent immunogens for the induction of specific antibodies. The invention is further based on the finding that immunostimulatory substances such as DNA oligonucleotides can be packaged into VLPs which renders them more immunogenic. Unexpectedly, the nucleic acids and oligonucleotides, respectively, present in VLPs can be replaced specifically by the immunostimulatory substances and DNA-oligonucleotides containing CpG motifs, respectively. Surprisingly, these packaged immunostimulatory substances, in particular immunostimulatory nucleic acids such as unmethylated CpG-containing oligonucleotides retained their immunostimulatory capacity without widespread activation of the innate immune system. The compositions comprising VLP's and the immunostimulatory substances in accordance with the present invention, and in particular the CpG-VLPs are dramatically more immunogenic than their CpG-free counterparts and induce enhanced B and T cell responses. In addition, the T cell responses against both the VLPs and MelanA peptide analogues are especially directed to the Th1 type. Human MelanA peptide analogues attached to CpG-loaded VLPs may therefore be ideal vaccines for prophylactic or therapeutic vaccination against tumors.

In a first embodiment, the invention provides a composition, typically and preferably for enhancing an immune response in an animal, comprising a virus-like particle, an immunostimulatory substance, preferably an immunostimulatory nucleic acid, and even more preferably an unmethylated CpG-containing oligonucleotide, and at least one antigen or antigenic determinant, where the immunostimulatory substance, nucleic acid or oligonucleotide is coupled, fused, or otherwise attached to or enclosed by, i.e., bound, to the virus-like particle and wherein said antigen or antigenic determinant is bound to said virus-like particle and wherein said antigen comprises, alternatively consists essentially of, or alternatively consists, of a human melanoma MelanA peptide analogue.

In a preferred embodiment of the invention, the immunostimulatory nucleic acids, in particular the unmethylated CpG-containing oligonucleotides are stabilized by phosphorothioate modifications of the phosphate backbone. In another preferred embodiment, the immunostimulatory nucleic acids, in particular the unmethylated CpG-containing oligonucleotides are packaged into the VLPs by digestion of RNA within the VLPs and simultaneous addition of the DNA oligonucleotides containing CpGs of choice. In an equally preferred embodiment, the VLPs can be disassembled before they are reassembled in the presence of CpGs.

In a further preferred embodiment, the immunostimulatory nucleic acids do not contain CpG motifs but nevertheless exhibit immunostimulatory activities. Such nucleic acids are described in WO 01/22972. All sequences described therein are hereby incorporated by way of reference.

In a further preferred embodiment, the virus-like particle is a recombinant virus-like particle. Also preferred, the virus-like particle is free of a lipoprotein envelope. Preferably, the recombinant virus-like particle comprises, or alternatively consists of, recombinant proteins of Hepatitis B virus, BK virus or other human Polyoma virus, measles virus, Sindbis virus, Rotavirus, Foot-and-Mouth-Disease virus, Retrovirus, Norwalk virus or human Papilloma virus, RNA-phages, Qβ-phage, GA-phage, fr-phage and Ty. In a specific embodiment, the virus-like particle comprises, or alternatively consists of, one or more different Hepatitis B virus core (capsid) proteins (HBcAgs). In a further preferred embodiment, the virus-like particle comprises recombinant proteins, or fragments thereof, of a RNA-phage. Preferred RNA-phages are Qβ-phage, AP 205-phage, GA-phage, fr-phage.

In a particular embodiment, the antigen comprises, or alternatively consists of, a cytotoxic T cell epitope. In a related embodiment, the virus-like particle comprises the Hepatitis B virus core protein and the cytotoxic T cell epitope is fused to the C-terminus of said Hepatitis B virus core protein. In one embodiment, they are fused by a leucine linking sequence. In a particularly preferred embodiment, the antigen is a polypeptide suited to induce an immune response against cancer cells.

In another aspect of the invention, there is provided a method of enhancing an immune response in a human or other animal species comprising introducing into the animal a composition comprising a virus-like particle, an immunostimulatory substance, preferably an immunostimulatory nucleic acid, and even more preferably an unmethylated CpG-containing oligonucleotide, and at least one antigen or antigenic determinant, where the immunostimulatory substance, preferably the nucleic acid, and even more preferably the oligonucleotide is bound (i.e. coupled, attached or enclosed) to the virus-like particle, and wherein said antigen comprises, alternatively consists essentially of, or alternatively consists of a human melanoma MelanA peptide analogue, and wherein said human melanoma MelanA peptide analogue is bound to said virus-like particle.

In yet another embodiment of the invention, the composition is introduced into an animal subcutaneously, intramuscularly, intranasally, intradermally, intravenously or directly into a lymph node. In an equally preferred embodiment, the immune enhancing composition is applied locally, near a tumor or local viral reservoir against which one would like to vaccinate.

In a preferred aspect of the invention, the immune response is a T cell response, and the T cell response against the antigen is enhanced. In a specific embodiment, the T cell response is a cytotoxic T cell response, and the cytotoxic T cell response against the MelanA peptide is enhanced.

The present invention also relates to a vaccine comprising an immunologically effective amount of the immune enhancing composition of the present invention together with a pharmaceutically acceptable diluent, carrier or excipient. In a preferred embodiment, the vaccine further comprises at least one adjuvant. The invention also provides a method of immunizing and/or treating an animal comprising administering to the animal an immunologically effective amount of the disclosed vaccine.

In a preferred embodiment of the invention, the immunostimulatory substance-containing VLPs, preferably the immunostimulatory nucleic acid-containing VLP's, an even more preferably the unmethylated CpG-containing oligonucleotide VLPs are used for vaccination of animals, typically and preferably humans, against melanoma, or MelanA peptides, respectively. The modified VLPs can typically and preferably be used to vaccinate against tumors. The vaccination can be for prophylactic or therapeutic purposes, or both.

The route of injection is preferably subcutaneous or intramuscular, but it would also be possible to apply the CpG-containing VLPs intradermally, intranasally, intravenously or directly into the lymph node. In an equally preferred embodiment, the CpG-containing MelanA peptide analogue-coupled or free VLPs are applied locally, near a tumor or local viral reservoir against which one would like to vaccinate.

It is to be understood that both the foregoing general description and the following detailed description are exemplary and explanatory only and are intended to provide further explanation of the invention as claimed.

BRIEF DESCRIPTION OF THE DRAWINGS/FIGURES

FIG. 1 shows the SDS-PAGE analysis of Qb-MelanA VLPs. MelanA-peptides were coupled to Qb VLPs, as described in Example 20. The final products were mixed with sample buffer and separated under reduced conditions on 16 % Novex® Tris-Glycine gels for 1.5 hours at 125 V. The separated proteins were stained by soaking the gel in Coomassie blue solution. Background staining was removed by washing the gel in 50% methanol, 8% acetic acid. The Molecular weight marker (P 77085, New England BioLabs, Beverly, USA) was used as reference for Qb-MelanA migration velocity (lane 1). 14 μg of either Qb alone (lane 2) or Qb derivatized with SMPH (lane 3) were loaded for comparison with 8 μg of each final product: Qb-MelanA 16-35 (lane 4), Qb-MelanA 16-35 A/L (lane 5), Qb- MelanA 26-35 (lane 6) and Qb- MelanA 26-35 A/L (lane 7).

Figure 2:
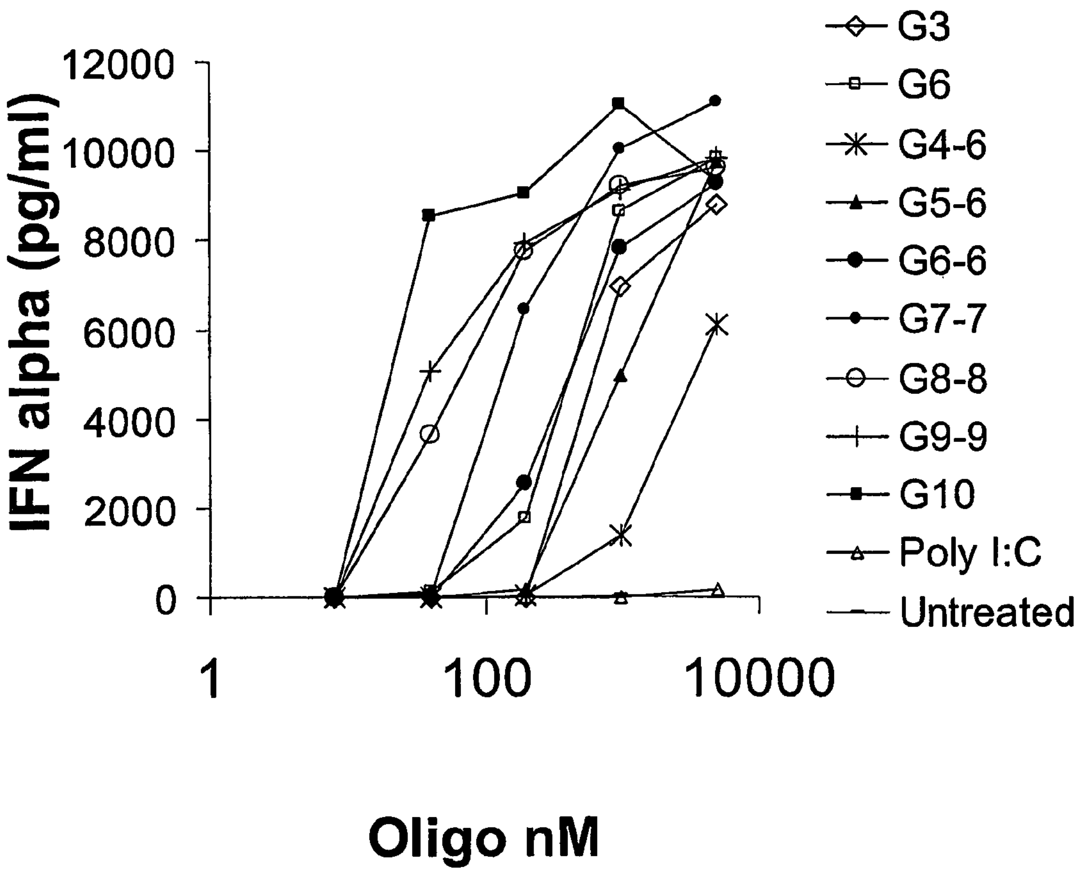

FIG. 2A shows IFN alpha released in the supernatants of ISS-treated human PBMC. PBMC were obtained from buffy coat and incubated with fivefold dilution of the indicated ISS for 18 h. The term G10 is used for the the oligonucleotide G10-PO, and the term G3 is used for the oligonucleotide G3-6). Supernatants were collected and IFN alpha was measured by ELISA, using a set of antibodies provided by PBL Biomedical Laboratories.

Figure 2B:
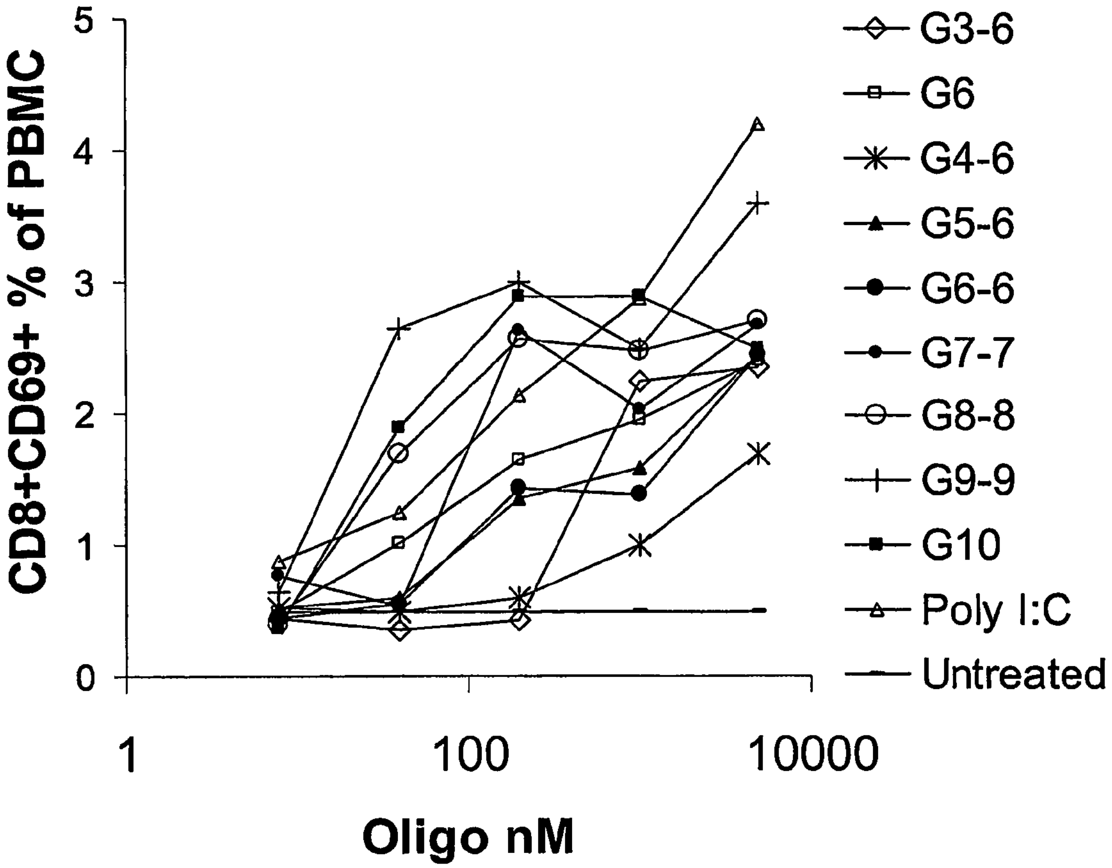

FIG. 2B shows the upregulation of CD69 on human CD8+ PBMC treated with ISS. PBMC were obtained from buffy coat and incubated with fivefold dilution of the indicated ISS for 18 h. Cells were washed and incubated with anti-CD8-FITC, anti-CD19-PE and anti-CD69-APC (all from BD PharMingen) for 20 min on ice. After washing, cells were analysed on a FACS Calibur using CellQuest software.

Figure 3:
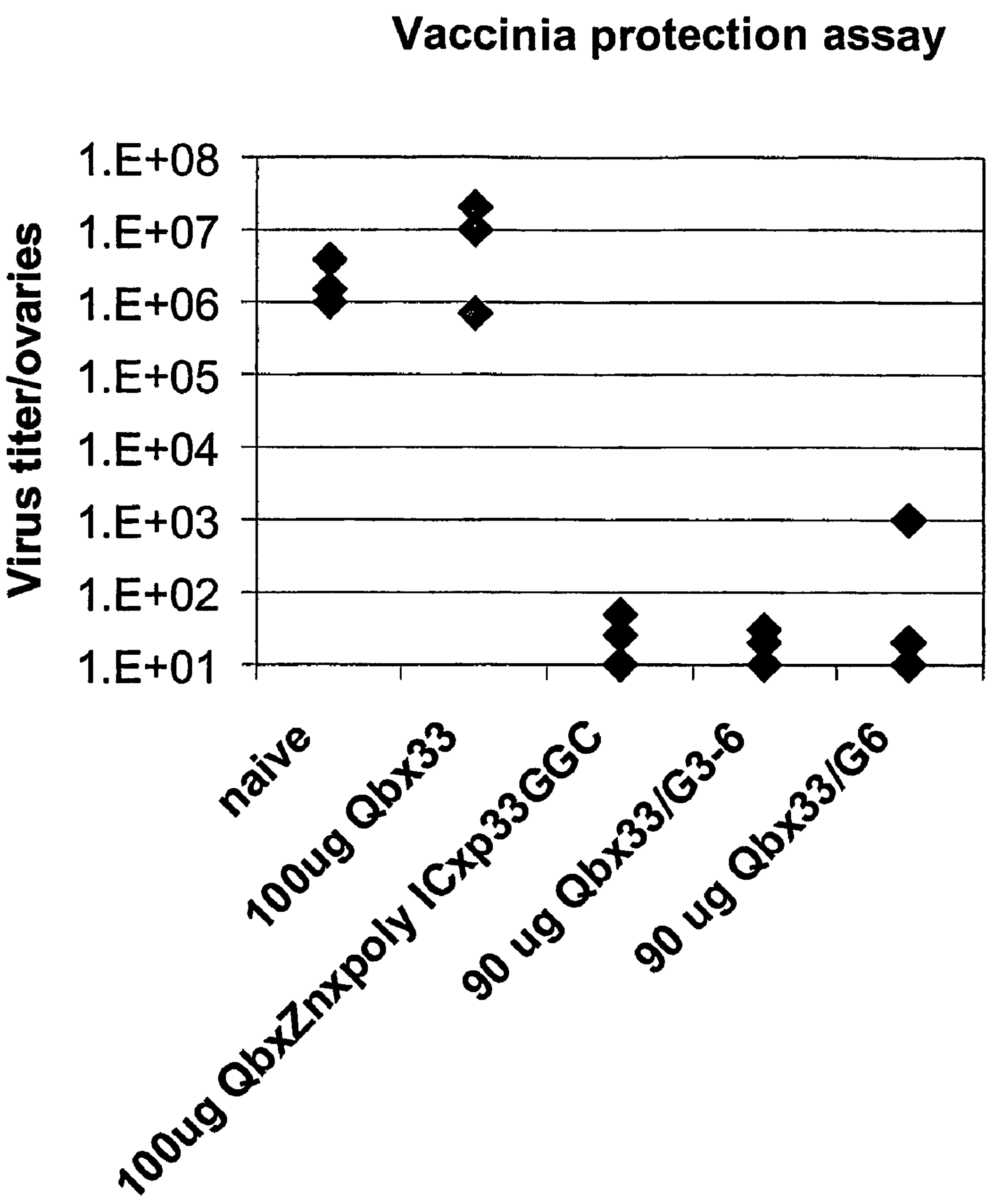

FIG. 3 shows the virus titers after immunizing mice with Qbx33 packaged with poly (I:C), G3-6, or G6. C57B16 mice were immunized by injecting either 100 μg Qbx33, 100 μg Qb VLPs packaged with poly (I:C) and coupled to p33 (Qb-pIC-33, also termed QbxZnxpolyICxp33GGC), 90 μg Qbx33 packaged with G3-6 (Qbx33/G3-6), or 90 μg Qbx33 packaged with G6 (Qbx33/G6). After eight days, mice were challenged with 1.5×106 plaque forming units Vaccinia virus, carrying the LCMV-p33 epitope. Five days later, mice were sacrificed and the ovaries were collected. A single cell suspension from the ovaries was prepared and added to BCS40 cells in serial dilutions. One day later, the cell layer was stained with a solution containing 50% Ethanol, 2% formaldehyde, 0.8% NaCl and 0.5% Crystal violet) and the viral plaques were counted.

DETAILED DESCRIPTION OF THE INVETION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are hereinafter described.

1. Definitions

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5, C6), aryl or heteroaryl moiety. However, in addition to an amino acid linker, a linker comprising preferably a C1-C6 alkyl-, cycloalkyl- (C5, C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, horses, cattle, pigs, dogs, cats, rats, mice, mammals, birds, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a T helper cell epitope (Th cell epitope) and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

A "tumor antigen" as used herein is a compound, such as a peptide, associated with a tumor or cancer and which is capable of provoking an immune response. In particular, the compound is capable of provoking an immune response when presented in the context of an MHC molecule. Tumor antigens can be prepared from cancer cells either by preparing crude extracts of cancer cells, for example, as described in Cohen, et al., Cancer Research, 54:1055 (1994), by partially purifying the antigens, by recombinant technology or by de novo synthesis of known antigens. Tumor antigens include antigens that are antigenic portions of or are a whole tumor or cancer polypeptide. Such antigens can be isolated or prepared recombinantly or by any other means known in the art. Cancers or tumors include, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Antigenic determinant: As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors.

Antigen presenting cell: As used herein, the term "antigen presenting cell" is meant to refer to a heterogenous population of leucocytes or bone marrow derived cells which possess an immunostimulatory capacity. For example, these cells are capable of generating peptides bound to MHC molecules that can be recognized by T cells. The term is synonymous with the term "accessory cell" and includes, for example, Langerhans' cells, interdigitating cells, B cells, macrophages and dendritic cells. Under some conditions, epithelial cells, endothelial cells and other, non-bone marrow derived cells may also serve as antigen presenting cells.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent, and again more preferably the association is through at least one, preferably one, non-peptide bond. As used herein, the term "association" as it applies to the first and second attachment sites, not only encompass the direct binding or association of the first and second attachment site forming the compositions of the invention but also, alternatively and preferably, the indirect association or binding of the first and second attachment site leading to the compositions of the invention, and hereby typically and preferably by using a heterobifunctional cross-linker.

Attachment Site, First: As used herein, the phrase "first attachment site" refers to an element of non-natural or natural origin typically and preferably being comprised by the virus-like particle, to which the second attachment site typically and preferably being comprised by the MelanA peptide analogue of the invention may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the virus-like particle. Multiple first attachment sites are present on the surface of virus-like particle typically in a repetitive configuration. Preferably, the first attachment site is an amino acid or a chemically reactive group thereof.

Attachment Site, Second: As used herein, the phrase "second attachment site" refers to an element associated with, typically and preferably being comprised by, the MelanA peptide analogue of the invention to which the first attachment site located on the surface of the virus-like particle may associate. The second attachment site of the MelanA peptide analogue of the invention may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the MelanA peptide analogue of the invention. The term "MelanA peptide analogue with at least one second attachment site" refers, therefore, to an antigen or antigenic construct comprising at least the MelanA peptide analogue of the invention and the second attachment site. However, in particular for a second attachment site, which is of non-natural origin, i.e. not naturally occurring within the MelanA peptide analogue of the invention, these antigen or antigenic constructs comprise an "amino acid linker".

Bound: As used herein, the term "bound" refers to binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled", "fused", "associated" and "attached". Moreover, with respect to the immunostimulatory substance being bound to the virus-like particle the term "bound" also includes the enclosement, or partial enclosement, of the immunostimulatory substance. Therefore, with respect to the immunostimulatory substance being bound to the virus-like particle the term "bound" is broader than and includes terms such as "coupled," "fused," "enclosed", "packaged" and "attached." For example, the immunostimulatory substance such as the unmethylated CpG-containing oligonucleotide can be enclosed by the VLP without the existence of an actual binding, neither covalently nor non-covalently.

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Coupled: As used herein, the term "coupled" refers to attachment by covalent bonds or by non-covalent interactions. With respect to the coupling of the antigen to the virus-like particle the term "coupled" preferably refers to attachment by covalent bonds. Moreover, with respect to the coupling of the antigen to the virus-like particle the term "coupled" preferably refers to association and attachment, respectively, by at least one non-peptide bond. Any method normally used by those skilled in the art for the coupling of biologically active materials can be used in the present invention.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

CpG: As used herein, the term "CpG" refers to an oligonucleotide which contains at least one unmethylated cytosine, guanine dinucleotide sequence (e.g. "CpG DNA" or DNA containing a cytosine followed by guanosine and linked by a phosphate bond) and stimulates/activates, e.g. has a mitogenic effect on, or induces or increases cytokine expression by, a vertebrate cell. For example, CpGs can be useful in activating B cells, NK cells and antigen-presenting cells, such as monocytes, dendritic cells and macrophages, and T cells. The CpGs can include nucleotide analogs such as analogs containing phosphorothioester bonds and can be double-stranded or single-stranded. Generally, double-stranded molecules are more stable in vivo, while single-stranded molecules have increased immune activity.

Epitope: As used herein, the term "epitope" refers to portions of a polypeptide having antigenic or immunogenic activity in an animal, preferably a mammal, and most preferably in a human. An "immunogenic epitope," as used herein, is defined as a portion of a polypeptide that elicits an antibody response or induces a T-cell response in an animal, as determined by any method known in the art. (See, for example, Geysen et al., Proc. Natl. Acad. Sci. USA 81:3998 4002 (1983)). The term "antigenic epitope," as used herein, is defined as a portion of a protein to which an antibody can immunospecifically bind its antigen as determined by any method well known in the art. Immunospecific binding excludes non specific binding but does not necessarily exclude cross reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8-10 such amino acids. If the epitope is an organic molecule, it may be as small as Nitrophenyl. Preferred epitopes are the MelanA-peptide analogues of the invention.

Immune response: As used herein, the term "immune response" refers to a humoral immune response and/or cellular immune response leading to the activation or proliferation of B- and/or T-lymphocytes. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant.

Immunization: As used herein, the terms "immunize" or "immunization" or related terms refer to conferring the ability to mount a substantial immune response (comprising antibodies or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Immunostimulatory nucleic acid: As used herein, the term immunostimulatory nucleic acid refers to a nucleic acid capable of inducing and/or enhancing an immune response. Immunostimulatory nucleic acids, as used herein, comprise ribonucleic acids and in particular deoxyribonucleic acids. Preferably, immunostimulatory nucleic acids contain at least one CpG motif e.g. a CG dinucleotide in which the C is unmethylated. The CG dinucleotide can be part of a palindromic sequence or can be encompassed within a non-palindromic sequence. Immunostimulatory nucleic acids not containing CpG motifs as described above encompass, by way of example, nucleic acids lacking CpG dinucleotides, as well as nucleic acids containing CG motifs with a methylated CG dinucleotide. The term "immunostimulatory nucleic acid" as used herein should also refer to nucleic acids that contain modified bases such as 4-bromo-cytosine.

Immunostimulatory substance: As used herein, the term "immunostimulatory substance" refers to a substance capable of inducing and/or enhancing an immune response. Immunostimulatory substances, as used herein, include, but are not limited to, toll-like receptor activing substances and substances inducing cytokine secretion. Toll-like receptor activating substances include, but are not limited to, immunostimulatory nucleic acids, peptideoglycans, lipopolysaccharides, lipoteichonic acids, imidazoquinoline compounds, flagellins, lipoproteins, and immunostimulatory organic substances such as taxol.

The term "natural human Melan A peptide" or "normal human Melan A peptide" as used herein, shall refer to a peptide comprising, or alternatively consisting essentially of, or alternatively consisting of the amino acid sequence EAAGIGILTV (SEQ ID NO: 78) representing amino acids positions 26-35 of the normal human MelanA protein sequence or AAGIGILTV (SEQ ID NO: 79) representing amino acids positions 27-35 of the normal human MelanA protein sequence.

The term "MelanA peptide analogue" or "human MelanA peptide analogue" or "human melanoma MelanA peptide analogue" as used herein shall be defined as a peptide in which the amino acid sequence of the corresponding normal MelanA peptide is altered by at least one amino acid or amino acid derivative, wherein this alteration may comprise an amino acid substitution and/or deletion and/or insertion or a combination thereof. In a preferred embodiment of the present invention, the term "MelanA peptide analogue" as used herein shall be defined as a peptide in which the amino acid sequence of the corresponding normal MelanA peptide (SEQ ID NO: 91) is altered by three, preferably two, and even more preferably one, amino acid or amino acid derivative, wherein this alteration may comprise an amino acid substitution and/or deletion and/or insertion or a combination thereof. In a further preferred embodiment of the present invention, the term "MelanA peptide analogue" as used herein shall be defined as a peptide in which the amino acid sequence of the corresponding normal MelanA peptide is altered by three, preferably two, and even more preferably one, amino acid or amino acid derivative, wherein this alteration may comprise an amino acid substitution and/or deletion and/or insertion or a combination thereof, and wherein this alteration is at position 26, 27, 28 and/or 35 of the normal human MelanA protein sequence (SEQ ID NO: 91), and wherein said alteration is preferably an amino acid substitution. The terms "MelanA peptide analogue", "human MelanA peptide analogue", "human melanoma MelanA peptide analogue", and "human melanoma MelanA/MART-1 peptide analogue" are used interchangeably.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 0.5 to 30 nanometers, more preferably 3 to 15 nanometers, even more preferably 3 to 8 nanometers.

Oligonucleotide: As used herein, the terms "oligonucleotide" or "oligomer" refer to a nucleic acid sequence comprising 2 or more nucleotides, generally at least about 6 nucleotides to about 100,000 nucleotides, preferably about 6 to about 2000 nucleotides, and more preferably about 6 to about 300 nucleotides, even more preferably about 20 to about 300 nucleotides, and even more preferably about 20 to about 100 nucleotides. The terms "oligonucleotide" or "oligomer" also refer to a nucleic acid sequence comprising more than 100 to about 2000 nucleotides, preferably more than 100 to about 1000 nucleotides, and more preferably more than 100 to about 500 nucleotides. "Oligonucleotide" also generally refers to any polyribonucleotide or polydeoxribonucleotide, which may be unmodified RNA or DNA or modified RNA or DNA. "Oligonucleotide" includes, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "oligonucleotide" refers to triple-stranded regions comprising RNA or DNA or both RNA and DNA. Further, an oligonucleotide can be synthetic, genomic or recombinant, e.g., λ-DNA, cosmid DNA, artificial bacterial chromosome, yeast artificial chromosome and filamentous phage such as M13. In a very preferred embodiment of the present invention, the oligonucleotide is a synthetic oligonucleotide.

The term "oligonucleotide" also includes DNAs or RNAs containing one or more modified bases and DNAs or RNAs with backbones modified for stability or for other reasons. For example, suitable nucleotide modifications/analogs include peptide nucleic acid, inosin, tritylated bases, phosphorothioates, alkylphosphorothioates, 5-nitroindole deoxyribofuranosyl, 5-methyldeoxycytosine and 5,6-dihydro-5,6-dihydroxydeoxythymidine. A variety of modifications have been made to DNA and RNA; thus, "oligonucleotide" embraces chemically, enzymatically or metabolically modified forms of polynucleotides as typically found in nature, as well as the chemical forms of DNA and RNA characteristic of viruses and cells. Other nucleotide analogs/modifications will be evident to those skilled in the art.

Packaged: The term "packaged" as used herein refers to the state of an immunostimulatory substance, preferably of an immunostimulatory nucleic acid, in relation to the VLP. The term "packaged" as used herein includes binding that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds such as thioether bonds, carbon-phosphorus bonds, and the like. The term also includes the enclosement, or partial enclosement, of a substance. The term "packaged" includes terms such as "coupled, "enclosed" and "attached." For example, the immunostimulatory substance such as the unmethylated CpG-containing oligonucleotide can be enclosed by the VLP without the existence of an actual binding, neither covalently nor non-covalently. In preferred embodiments, in particular, if immunostimulatory nucleic acids are the immunostimulatory substances, the term "packaged" indicates that the immunostimulatory nucleic acid in a packaged state is not accessible to DNAse dr RNAse hydrolysis. In preferred embodiments, the immunostimulatory nucleic acid is packaged inside the VLP capsids, most preferably in a non-covalent manner.

The compositions of the invention can be combined, optionally, with a pharmaceutically-acceptable carrier. The term "pharmaceutically-acceptable carrier" as used herein means one or more compatible solid or liquid fillers, diluents or encapsulating substances which are suitable for administration into a human or other animal. The term "carrier" denotes an organic or inorganic ingredient, natural or synthetic, with which the active ingredient is combined to facilitate the application.

Peptide: The term "peptide" as used herein, and in particular with respect to the human melanoma MelanA peptide or the normal human Melan A peptide, shall refer to a molecule composed of monomers (amino acids), typically and preferably linearly, linked by amide bonds (also known as peptide bonds). It indicates a molecular chain of amino acids and does not refer to a specific length of the product.

Organic molecule: As used herein, the term "organic molecule" refers to any chemical entity of natural or synthetic origin. In particular the term "organic molecule" as used herein encompasses, for example, any molecule being a member of the group of nucleotides, lipids, carbohydrates, polysaccharides, lipopolysaccharides, steroids, alkaloids, terpenes and fatty acids, being either of natural or synthetic origin. In particular, the term "organic molecule" encompasses molecules such as nicotine, cocaine, heroin or other pharmacologically active molecules contained in drugs of abuse. In general an organic molecule contains or is modified to contain a chemical functionality allowing its coupling, binding or other method of attachment to the virus-like particle in accordance with the invention.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

A substance which "enhances" an immune response refers to a substance in which an immune response is observed that is greater or intensified or deviated in any way with the addition of the substance when compared to the same immune response measured without the addition of the substance.

Preferably, a substance which "enhances" an immune response refers herein (i) to a substance in which the frequency of MelanA-specific, preferably natural human MelanA peptide-specific or human melanoma MelanA peptide analogue-specific, T cells increases when compared to the frequency of MelanA-specific, preferably natural human MelanA peptide-specific or human melanoma MelanA peptide analogue-specific, T cells measured without the addition of the substance, or (ii) to a substance in which the functionality of MelanA-specific, preferably natural human MelanA peptide-specific or human melanoma MelanA peptide analogue-specific, T cells deviates, preferably improves, when compared to the functionality of MelanA-specific, preferably natural human MelanA peptide-specific or human melanoma MelanA peptide analogue-specific, T cells measured without the addition of the substance, or (iii) to a substance in which the phenotype of MelanA-specific, preferably natural human MelanA peptide-specific or human melanoma MelanA peptide analogue-specific, T cells deviates such as the resulting T cells are capable of increased proliferation, reduced apoptosis or more efficient homing to tumor tissues, when compared to the proliferation, apoptosis or homing to tumor tissues of MelanA-specific, preferably natural human MelanA peptide-specific or human melanoma MelanA peptide analogue-specific, T cells measured without the addition of the substance.

The frequency of MelanA-specific, preferably natural human MelanA peptide-specific T cells or human melanoma MelanA peptide analogue-specific, is measured by way of MHC-class I/peptide complexes such as tetramer or multimer staining, preferably tetramer staining as described in Speiser, DE. et al. Eur J Immunol. 2002, Vol. 32, 731-741, whereas the functionality of MelanA-specific, preferably natural human MelanA peptide-specific or human melanoma MelanA peptide analogue-specific, T cells, is measured by way of cytokine release such as intracellular staining, cytokine capture assay, Elispot, ELISA, and preferably by Elispot as described in Speiser, D E. et al. Eur J Immunol. 2002, Vol. 32, 731-741. Moreover, the functionality of MelanA-specific, preferably natural human MelanA peptide-specific or human melanoma MelanA peptide analogue-specific, T cells, can also be measured by way of measuring MelanA-specific, preferably natural human MelanA peptide-specific or human melanoma MelanA peptide analogue-specific, cytolytic CD8+ T cell response in Chromium or Europium release assay as described in Valmori, D. et al. J. Immunol. 1998, 161, 6956-6962. The phenotyping of MelanA-specific, preferably natural human MelanA peptide-specific or human melanoma MelanA peptide analogue-specific, T cells is measured by way of using antibodies against cell surface or intracellular proteins such as cell activation markers, cell differentiation markers, homing markers, chemokine and cytokine receptors, costimulatory receptors, death receptors, killer activatory or inhibitory receptors, integrins, expression of anti-apoptotic proteins and absence of senescence markers and preferably by way of cell activation markers as described in Speiser, DE. et al. Eur J Immunol. 2002, Vol. 32, 731-741.

Effective Amount: As used herein, the term “effective amount” refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with “sufficient amount.”

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Self antigen: As used herein, the term “self antigen” refers to proteins encoded by the host’s genome or DNA and products generated by proteins or RNA encoded by the host’s genome or DNA are defined as self. Preferably, the tem “self antigen”, as used herein, refers to proteins encoded by the human genome or DNA and products generated by proteins or RNA encoded by the human genome or DNA are defined as self. The inventive compositions, pharmaceutical compositions and vaccines comprising self antigens are in particular capable of breaking tolerance against a self antigen when applied to the host. In this context, “breaking tolerance against a self antigen” shall refer to enhancing an immune response, as defined herein, and preferably enhancing a B or a T cell response, specific for the self antigen when applying the inventive compositions, pharmaceutical compositions and vaccines comprising the self antigen to the host. In addition, proteins that result from a combination of two or several self-molecules or that represent a fraction of a self-molecule and proteins that have a high homology two self-molecules as defined above (>95%, preferably >97%, more preferably >99%) may also be considered self.

Treatment: As used herein, the terms “treatment”, “treat”, “treated” or “treating” refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

Vaccine: As used herein, the term “vaccine” refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies, cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term “adjuvant” as used herein refers to non-specific stimulators of the immune response or substances that allow generation of a depot in the host which when combined with the vaccine of the present invention provide for an even more enhanced immune response. A variety of adjuvants can be used. Examples include incomplete Freund’s adjuvant, aluminum hydroxide and modified muramyldipeptide. The term “adjuvant” as used herein also refers to typically specific stimulators of the immune response which when combined with the vaccine of the present invention provide for an even more enhanced and typically specific immune response. Examples include, but limited to, GM-CSF, IL-2, IL-12, IFNα. Further examples are within the knowledge of the person skilled in the art.

Virus-like particle: As used herein, the term “virus-like particle” refers to a structure resembling a virus particle but which has not been demonstrated to be pathogenic. Typically, a virus-like particle in accordance with the invention does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. As indicated, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (SEQ ID: No 10) generated by expression of a Qβ CP gene containing, for example, a TAA stop codon precluding any expression of the longer A1 protein through suppression, see Kozlovska, T. M., et al., Intervirology 39: 9-15 (1996)), or additionally contain A1 protein subunits (SEQ ID: No 11) in the capsid assembly. The readthrough process has a low efficiency and is leading to an only very low amount of A1 protein in the VLPs. An extensive number of examples have been performed with different combinations of ISS packaged and antigen coupled. No differences in the coupling efficiency and the packaging have been observed when VLPs of Qβ coat protein assembled exclusively from Qβ CP subunits or VLPs of Qβ coat protein containing additionally A1 protein subunits in the capsids were used. Furthermore, no difference of the immune response between these QβVLP preparations was observed. Therefore, for the sake of clarity the term "QβVLP" is used throughout the description of the examples either for VLPs of Qβ coat protein assembled exclusively from Qβ CP subunits or VLPs of Qβ coat protein containing additionally A1 protein subunits in the capsids.

The term "virus particle" as used herein refers to the morphological form of a virus. In some virus types it comprises a genome surrounded by a protein capsid; others have additional structures (e.g., envelopes, tails, etc.).

Non-enveloped viral particles are made up of a proteinaceous capsid that surrounds and protects the viral genome. Enveloped viruses also have a capsid structure surrounding the genetic material of the virus but, in addition, have a lipid bilayer envelope that surrounds the capsid. In a preferred embodiment of the invention, the VLP's are free of a lipoprotein envelope or a lipoprotein-containing envelope. In a further preferred embodiment, the VLP's are free of an envelope altogether.

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, 2nd edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," Meth. Enzymol. 128, Academic Press San Diego (1990); Scopes, R. K., "Protein Purification Principles and Practice," 3rd ed., Springer-Verlag, New York (1994)) are also adequately described in the literature, all of which are incorporated herein by reference.

2. Compositions and Methods for Enhancing an Immune Response

The disclosed invention provides compositions and methods for enhancing an immune response against one or more antigens in an animal. Compositions of the invention comprise, or alternatively consist essentially of, or alternatively consist of, a virus-like particle, at least one immunostimulatory substance, preferably an immunostimulatory nucleic acid, and even more preferably an unmethylated CpG-containing oligonucleotide, and at least one antigen or antigenic determinant, wherein the immunostimulatory substance, the immunostimulatory nucleic acid or the oligonucleotide is bound to the virus-like particle, and wherein said antigen or antigenic determinant is bound to said virus-like particle, and wherein said antigen comprises, alternatively consists essentially of, or alternatively consists of a human melanoma MelanA peptide analogue. Furthermore, the invention conveniently enables the practitioner to construct such a composition for various treatment and/or prophylactic prevention purposes, which include the prevention and/or treatment of cancers, for example.

Virus-like particles in the context of the present application refer to structures resembling a virus particle but which are not pathogenic. In general, virus-like particles lack the viral genome and, therefore, are noninfectious. Also, virus-like particles can be produced in large quantities by heterologous expression and can be easily purified.

In a preferred embodiment, the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus, measles virus, Sindbis virus, rotavirus, foot-and-mouth-disease virus, Norwalk virus, the retroviral GAG protein, the retrotransposon Ty protein p1, the surface protein of Hepatitis B virus, human papilloma virus, human polyoma virus, BK virus (BKV), RNA phages, Ty, fr-phage, GA-phage, AP 205-phage and, in particular, Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof.

In a more specific embodiment, the VLP can comprise, or alternatively consist of, recombinant polypeptides of Rotavirus; recombinant polypeptides of Norwalk virus; recombinant polypeptides of Alphavirus; recombinant proteins which form bacterial pili or pilus like structures; recombinant polypeptides of Foot and Mouth Disease virus; recombinant polypeptides of measles virus, recombinant polypeptides of Sindbis virus, recombinant polypeptides of Retrovirus; recombinant polypeptides of Hepatitis B virus (e.g., a HBcAg); recombinant polypeptides of Tobacco mosaic virus; recombinant polypeptides of Flock House Virus; recombinant polypeptides of human Papillomavirus; recombinant polypeptides of Polyoma virus and, in particular, recombinant polypeptides of human Polyoma virus, and in particular recombinant polypeptides of BK virus; recombinant polypeptides of bacteriophages, recombinant polypeptides of RNA phages; recombinant polypeptides of Ty; recombinant polypeptides of fr-phage, recombinant polypeptides of GA-phage, recombinant polypeptides of AP 205-phage and, in particular, recombinant polypeptides of Qβ-phage. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; 1) bacteriophage PP7; and m) bacteriophage AP205.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr or of the RNA-bacteriophage AP205.

In a further preferred embodiment of the present invention, the recombinant proteins comprise, or alternatively consist essentially of, or alternatively consist of coat proteins of RNA phages.

RNA-phage coat proteins forming capsids or VLPs, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein), bacteriophage R17 (PIR Accession No. VCBPR7), bacteriophage fr (SEQ ID NO:13; PIR Accession No. VCBPFR), bacteriophage GA (SEQ ID NO: 14; GenBank Accession No. NP-040754), bacteriophage SP (GenBank Accession No. CAA30374 referring to SP CP and Accession No. NP_695026 referring to SP A1 protein), bacteriophage MS2 (PIR Accession No. VCBPM2), bacteriophage M11 (GenBank Accession No. AAC06250), bacteriophage MX1 (GenBank Accession No. AAC14699), bacteriophage NL95 (GenBank Accession No. AAC14704), bacteriophage f2 (GenBank Accession No. P03611), bacteriophage PP7 (SEQ ID NO: 19), and bacteriophage AP205 (SEQ ID NO: 31). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of QβA1 protein relative to Qβ CP in the capsid assembly will be limited, in order to ensure capsid formation. Further specific examples of bacteriophage coat proteins are described in WO 02/056905 on page 45 and 46 incorporated herein by way of reference. Further preferred virus-like particles of RNA-phages, in particular of Qβ in accordance of this invention are disclosed in WO 02/056905, the disclosure of which is herewith incorporated by reference in its entirety.

In a further preferred embodiment of the present invention, the virus-like particle comprises, or alternatively consists essentially of, or alternatively consists of recombinant proteins, or fragments thereof, of a RNA-phage, wherein the recombinant proteins comprise, consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion. The deletion, substitution or addition of at least one lysine residue allows varying the degree of coupling, i.e. the amount of human melanoma MelanA peptide analogues per subunits of the VLP of the RNA-phages, in particular, to match and tailor the requirements of the vaccine. In a preferred embodiment of the present invention, on average at least 1.0 human melanoma MelanA peptide analogue per subunit are linked to the VLP of the RNA-phage. This value is calculated as an average over all the subunits or monomers of the VLP of the RNA-phage. In a further preferred embodiment of the present invention, at least 1.1, 1.2, 1.3, 1.4, 1.5, 1.6, 1.7, 1.8, 1.9 or at least 2.0 human melanoma MelanA peptide analogues are linked to the VLP of the RNA-phages as being calculated as a coupling average over all the subunits or monomers of the VLP of the RNA-phage.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:10, or a mixture of coat proteins having amino acid sequences of SEQ ID NO:10 and of SEQ ID NO: 11 or mutants of SEQ ID NO: 11 and wherein the N-terminal methionine is preferably cleaved.

In a further preferred embodiment of the present invention, the virus-like particle comprises, consists essentially of or alternatively consists of recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ-240" (Lys13-Arg; SEQ ID NO:20), "Qβ-243" (Asn 10-Lys; SEQ ID NO:21), "Qβ-250" (Lys 2-Arg, Lys13-Arg; SEQ ID NO:22), "Qβ-251" (SEQ ID NO:23) and "Qβ-259" (Lys 2-Arg, Lys16-Arg; SEQ ID NO:24). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO: 20; b) the amino acid sequence of SEQ ID NO:21; c) the amino acid sequence of SEQ ID NO: 22; d) the amino acid sequence of SEQ ID NO:23; and e) the amino acid sequence of SEQ ID NO: 24. The construction, expression and purification of the above indicated Qβ coat proteins, mutant Qβ coat protein VLPs and capsids, respectively, are disclosed in WO02/056905. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins, J., et al., J. Gen. Virol. 83: 1523-33 (2002)). AP205 coat protein can be expressed from plasmid pAP283-58 (SEQ ID NO: 30), which is a derivative of pQb10 (Kozlovska, T. M. et al., Gene 137:133-37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in WO 04/007538 which is incorporated by reference in its entirety. Vectors pQb10 and pQb185 are vectors derived from pGEM vector, and expression of the cloned genes in these vectors is controlled by the trp promoter (Kozlovska, T. M. et al., Gene 137:133-37 (1993)). Plasmid pAP283-58 (SEQ ID NO:30) comprises a putative AP205 ribosomal binding site in the following sequence, which is downstream of the XbaI site, and immediately upstream of the ATG start codon of the AP205 coat protein: tctagaATTTTCTGCGCACCCAT CCCGGGTGGCGCCCAAAGTGAGGAAAATCACatg (bases 77-133 of SEQ ID NO: 30). The vector pQb185 comprises a Shine Delagarno sequence downstream from the XbaI site and upstream of the start codon (tctagaTTAACCCAACGCGT AGGAGTCAGGCCatg (SEQ ID NO: 61), Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 31) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 32), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID NO: 33), which is derived directly from pQb185, and which contains the mutant AP205 coat protein gene instead of the Qβ coat protein gene. Vectors for expression of the AP205 coat protein are transfected into *E. coli* for expression of the AP205 coat protein.

Methods for expression of the coat protein and the mutant coat protein, respectively, leading to self-assembly into VLPs are described in WO 04/007538, which is incorporated by reference in its entirety. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., Gene 137:133-37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or alternatively consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in WO 04/007538, which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., *Structure* 4:543-554 (1996)). Using such information, one skilled in the art could readily identify surface exposed residues and modify bacteriophage coat proteins such that one or more reactive amino acid residues can be inserted. Thus, one skilled in the art could readily generate and identify modified forms of bacteriophage coat proteins which can be used in the practice of the invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used for the inventive compositions and vaccine compositions. Further possible examples of modified RNA bacteriophages as well as variants of proteins and N- and C terminal truncation mutants which form capsids or capsid like structures, as well as methods for preparing such compositions and vaccine compositions, respectively, which are suitable for use in the present invention are described in WO 02/056905 on page 50, line 33 to page 52, line 29.

The invention thus includes compositions and vaccine compositions prepared from proteins which form capsids or VLPs, methods for preparing these compositions from individual protein subunits and VLPs or capsids, methods for preparing these individual protein subunits, nucleic acid molecules which encode these subunits, and methods for vaccinating and/or eliciting immunological responses in individuals using these compositions of the present invention.

In another preferred embodiment of the invention, the VLP's are free of a lipoprotein envelope or a lipoprotein-containing envelope. In a further preferred embodiment, the VLP's are free of an envelope altogether.

The lack of a lipoprotein envelope or lipoprotein-containing envelope and, in particular, the complete lack of an envelope leads to a more defined virus-like particle in its structure and composition. Such more defined virus-like particles, therefore, may minimize side-effects. Moreover, the lack of a lipoprotein-containing envelope or, in particular, the complete lack of an envelope avoids or minimizes incorporation of potentially toxic molecules and pyrogens within the virus-like particle.

In one embodiment, the invention provides a vaccine composition of the invention comprising a virus-like particle, wherein preferably said virus-like particle is a recombinant virus-like particle. Preferably, the virus-like particle comprises, or alternatively consists essentially of, or alternatively consists of, recombinant proteins, or fragments thereof, of a RNA-phage, preferably of coat proteins of RNA phages. Alternatively, the recombinant proteins of the virus-like particle of the vaccine composition of the invention comprise, or alternatively consist essentially of, or alternatively consist of mutant coat proteins of RNA phages, wherein the RNA-phage is selected from the group consisting of: (a) bacteriophage Q(; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (k) bacteriophage f2; (1) bacteriophage PP7; and (m) bacteriophage AP205.

In a preferred embodiment, the mutant coat proteins of said RNA phage have been modified by removal, or by addition of at least one lysine residue by way of substitution. In another preferred embodiment, the mutant coat proteins of said RNA phage have been modified by deletion of at least one lysine residue or by addition of at least one lysine residue by way of insertion. In a preferred embodiment, the virus-like particle comprises recombinant proteins or fragments thereof, of RNA-phage Qβ, RNA-phage fr, or RNA-phage AP205.

As previously stated, the invention includes virus-like particles or recombinant forms thereof. Skilled artisans have the knowledge to produce such particles and attach antigens thereto. Further preferred embodiments of the present invention hereto are disclosed in the Example Section.

In one embodiment, the virus-like particle comprises, or alternatively consists essentially of, or alternatively consists of recombinant proteins, or fragments thereof, of the BK virus (BKV), wherein the recombinant proteins comprise, or alternatively consist essentially of, or alternatively consist of proteins having an amino acid sequence of SEQ ID NO:12. BK virus (BKV) is a non-enveloped double stranded DNA virus belonging to the polyoma virus subfamily of the papovaviridae. VP1 is the major capsid protein of BKV. VP1 has 362 amino acids (SEQ ID NO: 12, Gene Bank entry: AAA46882) and is 42 kDa in size. When produced in *E. coli*, insect cells or yeast VP1 spontaneously forms capsid structures (Salunke D. M., et al., Cell 46(6):895-904 (1986); Sasnauskas, K., et al., Biol. Chem. 380(3):381-6 (1999); Sasnauskas, K., et al., 3rd International Workshop "Virus-like particles as vaccines" Berlin, September 26-29 (2001); Touze, A., et al., J Gen Virol. 82(Pt 12):3005-9 (2001). The capsid is organized in 72 VPI pentamers forming an icosahedral structure. The capsids have a diameter of approximately 45 nm.

In one embodiment, the particles used in compositions of the invention are composed of a Hepatitis B capsid (core) protein (HBcAg) or a fragment of a HBcAg which has been modified to either eliminate or reduce the number of free cysteine residues. Zhou et al. (J. Virol. 66:5393 5398 (1992)) demonstrated that HBcAgs which have been modified to remove the naturally resident cysteine residues retain the ability to associate and form multimeric structures. Thus, core particles suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. For example, the HBcAg protein having the amino acid sequence shown in SEQ ID NO: 16 is 185 amino acids in length and is generated by the processing of a 212 amino acid Hepatitis B core antigen precursor protein. This processing results in the removal of 29 amino acids from the N terminus of the Hepatitis B core antigen precursor protein. Similarly, the HBcAg protein that is 185 amino acids in length is generated by the processing of a 214 amino acid Hepatitis B core antigen precursor protein.

In preferred embodiments, vaccine compositions of the invention will be prepared using the processed form of a HBcAg (i.e., a HBcAg from which the N terminal leader sequence of the Hepatitis B core antigen precursor protein have been removed).

Further, when HBcAgs are produced under conditions where processing will not occur, the HBcAgs will generally be expressed in "processed" form. For example, bacterial systems, such as *E. coli*, generally do not remove the leader sequences, also referred to as "signal peptides," of proteins which are normally expressed in eukaryotic cells. Thus, when an *E. coli* expression system directing expression of the protein to the cytoplasm is used to produce HBcAgs of the invention, these proteins will generally be expressed such that the N terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in WO 02/056905. For the latter application, it is in particular referred to Example 23, 24, 31 and 51. All three documents are explicitly incorporated herein by reference.

The present invention also includes HBcAg variants which have been modified to delete or substitute one or more additional cysteine residues. Thus, the vaccine compositions of the invention include compositions comprising HBcAgs in which cysteine residues not present in the amino acid sequence shown in SEQ ID NO: 16 have been deleted.

It is well known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (J. Virol. 73:10122 10128 (1999)), for example, describe variants in which the isoleucine residue at position corresponding to position 97 in SEQ ID NO:25 is replaced with either a leucine residue or a phenylalanine residue. The amino acid sequences of a number of HBcAg variants, as well as several Hepatitis B core antigen precursor variants, are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X85299, X85307, X65257, X85311, X85301 (SEQ ID NO:26), X85314, X85287, X85272, X85319, AB010289, X85285, AB010289, AF121242, M90520 (SEQ ID NO:27), P03153, AF110999, and M95589, the disclosures of each of which are incorporated herein by reference. The sequences of the hereinabove mentioned Hepatitis B core antigen precursor variants are further disclosed in WO 01/85208 in SEQ ID NOs: 89-138 of the application WO 01/85208. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:28. Further HBcAg variants suitable for use in the compositions of the invention, and which may be further modified according to the disclosure of this specification are described in WO 01/98333, WO 00/177158 and WO 00/214478.

HBcAgs suitable for use in the present invention can be derived from any organism so long as they are able to enclose or to be coupled or otherwise attached to, in particular as long as they are capable of packaging, an unmethylated CpG-containing oligonucleotide and induce an immune response.

As noted above, generally processed HBcAgs (i.e., those which lack leader sequences) will be used in the vaccine compositions of the invention. The present invention includes vaccine compositions, as well as methods for using these compositions, which employ the above described variant HBcAgs.

Further included within the scope of the invention are additional HBcAg variants which are capable of associating to form dimeric or multimeric structures. Thus, the invention further includes vaccine compositions comprising HBcAg polypeptides comprising, or alternatively consisting of, amino acid sequences which are at least 80%, 85%, 90%, 95%, 97% or 99% identical to any of the wild-type amino acid sequences, and forms of these proteins which have been processed, where appropriate, to remove the N terminal leader sequence.

Whether the amino acid sequence of a polypeptide has an amino acid sequence that is at least 80%, 85%, 90%, 95%, 97% or 99% identical to one of the wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The amino acid sequences of the hereinabove mentioned HBcAg variants and precursors are relatively similar to each other. Thus, reference to an amino acid residue of a HBcAg variant located at a position which corresponds to a particular position in SEQ ID NO:28, refers to the amino acid residue which is present at that position in the amino acid sequence shown in SEQ ID NO:28. The homology between these HBcAg variants is for the most part high enough among Hepatitis B viruses that infect mammals so that one skilled in the art would have little difficulty reviewing both the amino acid sequence shown in SEQ ID NO:28, and that of a particular HBcAg variant and identifying "corresponding" amino acid residues. Furthermore, the HBcAg amino acid sequence shown in SEQ ID NO:27, which shows the amino acid sequence of a HBcAg derived from a virus which infect woodchucks, has enough homology to the HBcAg having the amino acid sequence shown in SEQ ID NO:28 that it is readily apparent that a three amino acid residue insert is present in SEQ ID NO:27 between amino acid residues 155 and 156 of SEQ ID NO:28.

The invention also includes vaccine compositions which comprise HBcAg variants of Hepatitis B viruses which infect birds, as wells as vaccine compositions which comprise fragments of these HBcAg variants. As one skilled in the art would recognize, one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue. Expression and purification of an HBcAg-Lys variant has been described in Example 24 of WO 02/056905 and the construction of a HBcAg devoid of free cysteine residues and containing an inserted lysine residue has been described in Example 31 of WO 02/056905.

In other embodiments, compositions and vaccine compositions, respectively, of the invention will contain HBcAgs from which the C terminal region (e.g., amino acid residues 145 185 or 150 185 of SEQ ID NO: 28) has been removed. Thus, additional modified HBcAgs suitable for use in the practice of the present invention include C terminal truncation mutants. Suitable truncation mutants include HBcAgs where 1, 5, 10, 15, 20, 25, 30, 34, 35, amino acids have been removed from the C terminus.

HBcAgs suitable for use in the practice of the present invention also include N terminal truncation mutants. Suitable truncation mutants include modified HBcAgs where 1, 2, 5, 7, 9, 10, 12, 14, 15, or 17 amino acids have been removed from the N terminus.

Further HBcAgs suitable for use in the practice of the present invention include N and C terminal truncation mutants. Suitable truncation mutants include HBcAgs where 1, 2, 5, 7, 9, 10, 12, 14, 15, and 17 amino acids have been removed from the N terminus and 1, 5, 10, 15, 20, 25, 30, 34, 35 amino acids have been removed from the C terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the MelanA peptide analogue of the invention to the VLP of HBcAg. In preferred embodiments, compositions of the invention are prepared using a HBcAg comprising, or alternatively consisting of, amino acids 1-144, or 1-149, 1-185 of SEQ ID NO:28, which is modified so that the amino acids corresponding to positions 79 and 80 are replaced with a peptide having the amino acid sequence of Gly-Gly-Lys-Gly-Gly (SEQ ID NO:18) resulting in the HBcAg polypeptide having the sequence shown in SEQ ID NO:29). These compositions are particularly useful in those embodiments where an antigenic determinant is coupled to a VLP of HBcAg. In further preferred embodiments, the cysteine residues at positions 48 and 107 of SEQ ID NO:28 are mutated to serine. The invention further includes compositions comprising the corresponding polypeptides having amino acid sequences shown in any of the hereinabove mentioned Hepatitis B core antigen precursor variants, which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild type" HBcAg and a modified HBcAg in which one or more amino acid residues have been altered (e.g., deleted, inserted or substituted). Further, preferred vaccine compositions of the invention are those which present highly ordered and repetitive antigen arrays, wherein the antigen is a human melanoma MelanA peptide analog.

As previously disclosed, the invention is partly based on the surprising finding that immunostimulatory substances, preferably immunostimulatory nucleic acids and even more preferably DNA oligonucleotides or alternatively poly (I:C) can be packaged into VLPs. Unexpectedly, the nucleic acids present in VLPs can be replaced specifically by the immunostimulatory substances, preferably by the immunostimulatory nucleic acids and even more preferably by the DNA-oligonucleotides containing CpG motifs or poly (I:C). As an example, the CpG-VLPs are more immunogenic and elicit more specific effects than their CpG-free counterparts and induce enhanced B and T cell responses. The immune response against antigens coupled, fused or attached otherwise to the VLPs is similarly enhanced as the immune response against the VLP itself. In addition, the T cell responses against both the VLPs and antigens are especially directed to the Th1 type. Furthermore, the packaged nucleic acids and CpGs, respectively, are protected from degradation, i.e., they are more stable. Moreover, non-specific activation of cells from the innate immune system is dramatically reduced.

The innate immune system has the capacity to recognize invariant molecular pattern shared by microbial pathogens. Recent studies have revealed that this recognition is a crucial step in inducing effective immune responses. The main mechanism by which microbial products augment immune responses is to stimulate APC, especially dendritic cells to produce proinflammatory cytokines and to express high levels costimulatory molecules for T cells. These activated dendritic cells subsequently initiate primary T cell responses and dictate the type of T cell-mediated effector function.

Two classes of nucleic acids, namely 1) bacterial DNA that contains immunostimulatory sequences, in particular unmethylated CpG dinucleotides within specific flanking bases (referred to as CpG motifs) and 2) double-stranded RNA synthesized by various types of viruses represent important members of the microbial components that enhance immune responses. Synthetic double stranded (ds) RNA such as polyinosinic-polycytidylic acid (poly I:C) are capable of inducing dendritic cells to produce proinflammatory cytokines and to express high levels of costimulatory molecules.

A series of studies by Tokunaga and Yamamoto et al. has shown that bacterial DNA or synthetic oligodeoxynucleotides induce human PBMC and mouse spleen cells to produce type I interferon (IFN) (reviewed in Yamamoto et al., Springer Semin Immunopathol. 22:11-19). Poly (I:C) was originally synthesized as a potent inducer of type I IFN but also induces other cytokines such as IL-12.

Preferred ribonucleic acid encompass polyinosinic-polycytidylic acid double-stranded RNA (poly I:C). Ribonucleic acids and modifications thereof as well as methods for their production have been described by Levy, H. B (Methods Enzymol. 1981, 78:242-251), DeClercq, E (Methods Enzymol. 1981,78:227-236) and Torrence, P. F. (Methods Enzymol 1981;78:326-331) and references therein. Further preferred ribonucleic acids comprise polynucleotides of inosinic acid and cytidiylic acid such poly (IC) of which two strands forms double stranded RNA. Ribonucleic acids can be isolated from organisms. Ribonucleic acids also encompass further synthetic ribonucleic acids, in particular synthetic poly (I:C) oligonucleotides that have been rendered nuclease resistant by modification of the phosphodiester backbone, in particular by phosphorothioate modifications. In a further embodiment the ribose backbone of poly (I:C) is replaced by a deoxyribose. Those skilled in the art know procedures how to synthesize synthetic oligonucleotides.

In another preferred embodiment of the invention molecules that active toll-like receptors (TLR) are enclosed. Ten human toll-like receptors are known uptodate. They are activated by a variety of ligands. TLR2 is activated by peptidoglycans, lipoproteins, lipopolysacchrides, lipoteichonic acid and Zymosan, and macrophage-activating lipopeptide MALP-2; TLR3 is activated by double-stranded RNA such as poly (I:C); TLR4 is activated by lipopolysaccharide, lipoteichoic acids and taxol and heat-shock proteins such as heat shock protein HSP-60 and Gp96; TLR5 is activated by bacterial flagella, especially the flagellin protein; TLR6 is activated by peptidoglycans, TLR7 is activated by imiquimoid and imidazoquinoline compounds, such as R-848, loxoribine and bropirimine and TLR9 is activated by bacterial DNA, in particular CpG DNA. Ligands for TLR1, TLR8 and TLR10 are not known so far. However, recent reports indicate that same receptors can react with different ligands and that further receptors are present. The above list of ligands is not exhaustive and further ligands are within the knowledge of the person skilled in the art.

Preferably, the unmethylated CpG-containing oligonucleotide comprises the sequence:

5'X1X2CGX3X4 3' wherein X1, X2, X3 and X4 are any nucleotide. In addition, the oligonucleotide can comprise about 6 to about 100,000 nucleotides, preferably about 6 to about 2000 nucleotides, more preferably about 20 to about 2000 nucleotides, and even more preferably comprises about 20 to about 300 nucleotides. In addition, the oligonucleotide can comprise more than 100 to about 2000 nucleotides, preferably more than 100 to about 1000 nucleotides, and more preferably more than 100 to about 500 nucleotides.

In a preferred embodiment, the CpG-containing oligonucleotide contains one or more phosphorothioate modifications of the phosphate backbone. For example, a CpG-containing oligonucleotide having one or more phosphate backbone modifications or having all of the phosphate backbone modified and a CpG-containing oligonucleotide wherein one, some or all of the nucleotide phosphate backbone modifications are phosphorothioate modifications are included within the scope of the present invention. Thus, in a preferred embodiment, at least one of the nucleotide X1, X2, X3, and X4 has a phosphate backbone modification.

In a further very preferred embodiment of the present invention, the immunostimulatory substance is an unmethylated CpG-containing oligonucleotide, wherein said unmethylated CpG-containing oligonucleotide has a nucleic acid sequence selected from the group consisting of (a) GGGGACGATCGTCGGGGGG ((SEQ ID NO: 2); and typically abbreviated herein as G3-6), (b) GGGGGACGATCGTCGGGGGG ((SEQ ID NO: 3); and typically abbreviated herein as G4-6), (c) GGGGGGACGATCGTCGGGGGG ((SEQ ID NO: 4); and typically abbreviated herein as G5-6), (d) GGGGGGGACGATCGTCGGGGGG ((SEQ ID NO: 5); and typically abbreviated herein as G6-6), (e) GGGGGGGGACGATCGTCGGGGGGG ((SEQ ID NO: 6); and typically abbreviated herein as G7-7), (f) GGGGGGGGGACGATCGTCGGGGGGGG ((SEQ ID NO: 7); and typically abbreviated herein as G8-8), (g) GGGGGGGGGGACGATCGTCGGGGGGGGG ((SEQ ID NO: 8); and typically abbreviated herein as G9-9), (h) GGGGGGCGACGACGATCGTCGTCGGGGGGG ((SEQ ID NO: 9); and typically abbreviated herein as G6), (i) tccatgacgttcctgaataat ((SEQ ID NO: 34); and typically abbreviated herein as CyCpGpt), (j) TCCATGACGTTCCTGAATAAT ((SEQ ID NO: 35); and typically abbreviated herein CyCpG), (k) tccatgacgttcctgacgtt ((SEQ ID NO: 36); and typically abbreviated herein as B-CpGpt), (l) TCCATGACGTTCCTGACGTT ((SEQ ID NO: 37); and typically abbreviated herein as B-CpG), (m) ggggtcaacgttgaggggg ((SEQ ID NO: 38); and typically abbreviated herein as NKCpOpt), (n) GGGGTCAACGTTGA GGGGG ((SEQ ID NO: 39); and typically abbreviated herein as NKCpG), (o) attattcaggaacgtcatgga ((SEQ ID NO: 40); and typically abbreviated herein as CyCpG-rev-pt), (p) GGGGGGGGGGGACGATCGTCGGGGGGGGGG ((SEQ ID NO: 41); and typically abbreviated herein as g10gacga-PO (G10-PO)), (q) gggggggggggacgatcgtcgggggggggg ((SEQ ID NO: 42); and typically abbreviated herein g10gacga-PS (G10-PS)), (r) CGCGCGCGCGCGCGCGCGCGCGCGCGCGCGCGCGCGCGCGAAATGCATGTCAAAGACAGCAT ((SEQ ID NO: 43); and typically abbreviated herein as (CpG)20OpA), (s) TCCATGACGTTCCTGAATAATCGCGCGCGCGCGCGCGCGCGCGCGCGCGCGCGCGCGCGCGCG ((SEQ ID NO: 44); and typically abbreviated herein as Cy(CpG)20), (t) TCCATGACGTTCCTGAATAATCGCGCGCGCGCGCGCGCGCGCGCGCGCGCGCGCGCGCGCGCGAAATGCATGTCAAAGACAGCAT ((SEQ ID NO: 45); and typically abbreviated herein as Cy(CpG)20-OpA), (u) TCCATGACGTTCCTGAATAATAAATGCATGTCAAAGACAGCAT ((SEQ ID NO: 46); and typically abbreviated herein as CyOpA), (v) TCCATGACGTTCCTGAATAATTCCATGACGTTCCTGAATAATTCCATGACGTTCCTGAATAAT ((SEQ ID NO: 47); and typically abbreviated herein as CyCyCy), (w) TCCATGACGTTCCTGAATAATTCCATGACGTTCCTGAATAATTCCATGACGTTCCTGAATAATTGGATGACGTTGGTGAATAATTCCATGACGTTCCTGAATAATTCCATGACGTTCCTGAATAATTCCATGACGTTCCTGAATAATTCC ((SEQ ID NO: 48); and typically abbreviated herein as Cy150-1), and (x) CTAGAACTAGTGGATCCCCCGGGCTGCAGGAATTCGATTCATGACTTCCTGAATAATTCCATGACGTTGGTGAATAATTCCATGACGTTCCTGAATAATTCCATGACGTTCCTGAATAATTCCATGACGTTCCTGAATAATTCCATGACGTTCCTGAATAATTCCATGACGTTCCTGAATAATTCCATGACGTTCCTGAAAATTCCAATCAAGCTTATCGATACCGTCGACC (SEQ ID NO: 49), and typically abbreviated herein as dsCyCpG-253 (complementary strand not shown). Small letters as shown in the afore mentioned sequences of SEQ ID NO: 34 to SEQ ID NO: 49 indicate deoxynucleotides connected via phosphorothioate bonds while large letters indicate deoxynucleotides connected via phosphodiester bonds.

In again further very preferred embodiment of the present invention, the immunostimulatory substance is an unmethylated CpG-containing oligonucleotide, wherein said unmethylated CpG-containing oligonucleotide has a nucleic acid sequence of GGGGGGGGGGGACGATCGTCGGGGGGGGGG ((SEQ ID NO: 41); and typically abbreviated herein as g10gacga-PO or G10-PO).

The CpG-containing oligonucleotide can also be recombinant, genomic, synthetic, cDNA, plasmid-derived and single or double stranded. For use in the instant invention, the nucleic acids can be synthesized de novo using any of a number of procedures well known in the art. For example, the β-cyanoethyl phosphoramidite method (Beaucage, S. L., and Caruthers, M. H., Tet. Let. 22:1859 (1981); nucleoside H-phosphonate method (Garegg et al., Tet. Let. 27:4051-4054 (1986); Froehler et al., Nucl. Acid. Res. 14:5399-5407 (1986); Garegg et al., Tet. Let. 27:4055-4058 (1986), Gaffney et al., Tet. Let. 29:2619-2622 (1988)). These chemistries can be performed by a variety of automated oligonucleotide synthesizers available in the market. Alternatively, CpGs can be produced on a large scale in plasmids, (see Sambrook, T., et al., "Molecular Cloning: A Laboratory Manual," Cold Spring Harbor laboratory Press, New York, 1989) which after being administered to a subject are degraded into oligonucleotides. Oligonucleotides can be prepared from existing nucleic acid sequences (e.g., genomic or cDNA) using known techniques, such as those employing restriction enzymes, exonucleases or endonucleases.

The immunostimulatory substances, the immunostimulatory nucleic acids as well as the unmethylated CpG-containing oligonucleotide can be bound to the VLP by any way known is the art provided the composition enhances an immune response in an animal. For example, the oligonucleotide can be bound either covalently or non-covalently. In addition, the VLP can enclose, fully or partially, the immunostimulatory substances, the immunostimulatory nucleic acids as well as the unmethylated CpG-containing oligonucleotide. Preferably, the immunostimulatory nucleic acid as well as the unmethylated CpG-containing oligonucleotide can be bound to a VLP site such as an oligonucleotide binding site (either naturally or non-naturally occurring), a DNA binding site or a RNA binding site. In another embodiment, the VLP site comprises an arginine-rich repeat or a lysine-rich repeat.

One specific use for the compositions of the invention is to activate dendritic cells for the purpose of enhancing a specific immune response against antigens. The immune response can be enhanced using ex vivo or in vivo techniques. The ex vivo procedure can be used on autologous or heterologous cells, but is preferably used on autologous cells. In preferred embodiments, the dendritic cells are isolated from peripheral blood or bone marrow, but can be isolated from any source of dendritic cells. Ex vivo manipulation of dendritic cells for the purposes of cancer immunotherapy have been described in several references in the art, including Engleman, E. G., Cytotechnology 25:1 (1997); Van Schooten, W., et al., Molecular Medicine Today, June, 255 (1997); Steinman, R. M., Experimental Hematology 24:849 (1996); and Gluckman, J. C., Cytokines, Cellular and Molecular Therapy 3:187 (1997).

The dendritic cells can also be contacted with the inventive compositions using in vivo methods. In order to accomplish this, the CpGs are administered in combination with the VLP optionally coupled, fused or otherwise attached to an antigen directly to a subject in need of immunotherapy. In some embodiments, it is preferred that the VLPs/CpGs be administered in the local region of the tumor, which can be accomplished in any way known in the art, e.g., direct injection into the tumor.

A preferred embodiment of the present invention is to provide a composition for enhancing an immune response in an animal comprising (a) a virus-like particle; (b) at least one immunostimulatory substance; and (c) at least one antigen or antigenic determinant; wherein said antigen or said antigenic determinant is bound to said virus-like particle and wherein said antigen comprises, alternatively consists essentially of, or alternatively consists of a human melanoma MelanA peptide analogue, and wherein said immunostimulatory substance is bound to said virus-like particle, and wherein said immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 3'-terminus and at its 5'-terminus by more than two and less than 11 guanosine entities or, more preferably by 8-10 guanosine entities, or, most preferably by 10 guanosine entities.

We found that the inventive immunostimulatory substances, i.e. the unmethylated CpG-containing oligonucleotides, wherein the CpG motif of said unmethylated CpG-containing oligonucleotides are part of a palindromic sequence, wherein the palindromic sequence is GACGATCGTC (SEQ ID NO: 1), and wherein the palindromic sequence is flanked at its 3'-terminus and at its 5'-terminus by more than two and less than 11 guanosine entities, more preferably by 8-10 guanosine entities, or most preferably by 10 guanosine entities, are, in particular, effective at stimulating immune cells in vitro.

In a preferred embodiment of the present invention, the palindromic sequence comprises, or alternatively consist essentially of, or alternatively consists of or is GACGATCGTC (SEQ ID NO: 1), wherein said palindromic sequence is flanked at its 5'-terminus by at least 3 and at most 10 guanosine entities and wherein said palindromic sequence is flanked at its 3'-terminus by at least 6 and at most 10 guanosine entities. In another embodiment, the palindromic sequence is flanked at its 5'-terminus by at least 3 and at most 10 guanosine entities and wherein said palindromic sequence is flanked at its 3'-terminus by at least 6 and at most 10 guanosine entities.

In a further very preferred embodiment of the present invention, the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGACGATCGTCGGGGGG ((SEQ ID NO: 2); and typically abbreviated herein as G3-6), (b) GGGGGACGATCGTCGGGGGG ((SEQ ID NO: 3); and typically abbreviated herein as G4-6), (c) GGGGGGACGATCGTCGGGGGG ((SEQ ID NO: 4); and typically abbreviated herein as G5-6), (d) GGGGGGGACGATCGTCGGGGGG ((SEQ ID NO: 5); and typically abbreviated herein as G6-6), (e) GGGGGGGGACGATCGTCGGGGGGG ((SEQ ID NO: 6); and typically abbreviated herein as G7-7), (f) GGGGGGGGGACGATCGTCGGGGGGGG ((SEQ ID NO: 7); and typically abbreviated herein as G8-8), (g) GGGGGGGGGGACGATCGTCGGGGGGGGG ((SEQ ID NO: 8); and typically abbreviated herein as G9-9), (h) GGGGGGCGACGACGATCGTCGTCGGGGGGG ((SEQ ID NO: 9); and typically abbreviated herein as G6), and (i) GGGGGGGGGGGACGATCGTCGGGGGGGGGG ((SEQ ID NO: 41); and typically abbreviated herein as G10-PO).

In a further preferred embodiment of the present invention the immunostimulatory substance is an umnethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 5'-terminus by at least 4 and at most 10 guanosine entities and wherein said palindromic sequence is flanked at its 3'-terminus by at least 6 and at most 10 guanosine entities.

In another preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGGACGATCGTCGGGGGG ((SEQ ID NO: 3); and typically abbreviated herein as G4-6), (b) GGGGGGACGATCGTCGGGGGG ((SEQ ID NO: 4); and typically abbreviated herein as G5-6), (c) GGGGGGGACGATCGTCGGGGGG ((SEQ ID NO: 5); and typically abbreviated herein as G6-6), (d) GGGGGGGGACGATCGTCGGGGGGG ((SEQ ID NO: 6); and typically abbreviated herein as G7-7), (e) GGGGGGGGGACGATCGTCGGGGGGGG ((SEQ ID NO: 7); and typically abbreviated herein as G8-8), (f) GGGGGGGGGGACGATCGTCGGGGGGGGG ((SEQ ID NO: 8); and typically abbreviated herein as G9-9); and (g) GGGGGGGGGGGACGATCGTCGGGGGGGGGG ((SEQ ID NO: 41); and typically abbreviated herein as G10-PO).

In a further preferred embodiment of the present invention the immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 5'-terminus by at least 5 and at most 8 guanosine entities and wherein said palindromic sequence is flanked at its 3'-terminus by at least 6 and at most 10 guanosine entities.

The experimental data show that the ease of packaging of the preferred inventive immunostimulatory substances, i.e. the guanosine flanked, palindromic and unmethylated CpG-containing oligonucleotides, wherein the palindromic sequence is GACGATCGTC (SEQ ID NO: 1), and wherein the palindromic sequence is flanked at its 3'-terminus and at its 5'-terminus by less than 11 or less than 10 guanosine entities, into VLP's increases if the palindromic sequences are flanked by fewer guanosine entities. However, decreasing the number of guanosine entities flanking the palindromic sequences leads to a decrease of stimulating blood cells in vitro. Thus, packagability is paid by decreased biological activity of the indicated inventive immunostimulatory substances. The present preferred embodiments represent, thus, a compromise between packagability and biological activity.

In another preferred embodiment of the present invention the immunostimulatory substance is an umnethylated CpG-containing oligonucleotide, wherein the CpG motif of said unmethylated CpG-containing oligonucleotide is part of a palindromic sequence, wherein said unmethylated CpG-containing oligonucleotide has a nucleic acid sequence selected from (a) GGGGGGACGATCGTCGGGGGG ((SEQ ID NO: 4); and typically abbreviated herein as G5-6), (b) GGGGGGGACGATCGTCGGGGGG ((SEQ ID NO: 5); and typically abbreviated herein as G6-6), (c) GGGGGGGGACGATCGTCGGGGGGG ((SEQ ID NO: 6); and typically abbreviated herein as G7-7), (d) GGGGGGGGGACGATCGTCGGGGGGGG ((SEQ ID NO: 7); and typically abbreviated herein as G8-8); and (e) GGGGGGGGGGGACGATCGTCGGGGGGGGGG ((SEQ ID NO: 41); and typically abbreviated herein as G10-PO).

In a preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated has the nucleic acid sequence of SEQ ID NO: 7, i.e. the immunostimulatory substance is G8-8, or of SEQ ID NO: 41, i.e. G10-PO.

In a very preferred embodiment of the present invention the immunostimulatory substance is an unmethylated CpG-containing oligonucleotide, wherein the CpG motif of said unmethylated CpG-containing oligonucleotide is part of a palindromic sequence, wherein said unmethylated has the nucleic acid sequence of SEQ ID NO: 41, i.e. the immunostimulatory substance is G10-PO. Thus, in a very preferred embodiment, the present invention provides a composition for enhancing an immune response in an animal comprising (a) a virus-like particle; (b) at least one immunostimulatory substance; and (c) at least one antigen or antigenic determinant; wherein said antigen is bound to said virus-like particle and wherein said antigen comprises, alternatively consists essentially of, or alternatively consists of a human melanoma MelanA peptide analogue, and wherein said immunostimulatory substance is bound to said virus-like particle, and wherein said immunostimulatory substance is an unmethylated CpG-containing oligonucleotide, wherein the CpG motif of said unmethylated CpG-containing oligonucleotide is part of a palindromic sequence, wherein said palindromic sequence is GACGATCGTC (SEQ ID NO: 1), and wherein said palindromic sequence is flanked at its 3'-terminus and at its 5'-terminus by 10 guanosine entities.

As mentioned above, the optimal sequence used to package into VLPs is a compromise between packagability and biological activity. Taking this into consideration, the G8-8 immunostimulatoy substance is a preferred, and the G10-PO immunostimulatory substance a very preferred embodiment of the present invention since they are biologically highly active while still reasonably well packaged.

The inventive composition further comprise a human melanoma MelanA peptide analogue of the invention bound to the virus-like particle.

In a further preferred embodiment of the invention, the at least one MelanA peptide analogue is fused to the virus-like particle. As outlined above, a VLP is typically composed of at least one subunit assembling into a VLP. Thus, in again a further preferred embodiment of the invention, the MelanA peptide analogue is fused to at least one subunit of the virus-like particle or of a protein capable of being incorporated into a VLP generating a chimeric VLP-subunit-antigen fusion.

Fusion of the MelanA peptide analogue can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting MelanA peptide analogue sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of antigens or antigenic determinants to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79-81 are replaced with a foreign epitope. Thus, fusion, as referred to hereinafter, may be effected by insertion of the MelanA peptide analogue sequence in the sequence of a VLP subunit, by substitution of part of the sequence of the VLP subunit with the MelanA peptide analogue, or by a combination of deletion, substitution or insertions.

The chimeric MelanA peptide analogue—VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of, and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the VLP is a Hepatitis B core antigen VLP. Fusion proteins to either the N-terminus of a HBcAg (Neyrinck, S. et al., Nature Med. 5:1157-1163 (1999)) or insertions in the so called major immunodominant region (MIR) have been described (Pumpens, P. and Grens, E., Intervirology 44:98-114 (2001)), WO 01/98333), and are preferred embodiments of the invention. Naturally occurring variants of HBcAg with deletions in the MIR have also been described (Pumpens, P. and Grens, E., Intervirology 44:98-114 (2001), which is expressly incorporated by reference in its entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., Intervirology 44:98-114 (2001)). One skilled in the art will easily find guidance on how to construct fusion proteins using classical molecular biology techniques (Sambrook, J. et al., eds., Molecular Cloning, A Laboratory Manual, 2nd. edition, Cold Spring Habor Laboratory Press, Cold Spring Harbor, N.Y. (1989), Ho et al., Gene 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98-114 (2001), Neyrinck, S. et al., Nature Med. 5:1157-1163 (1999)) and can be used in the practice of the invention. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., Intervirology 44:98-114 (2001); EP 421 635; U.S. Pat. No. 6,231,864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., Intervirology 44:98-114 (2001); EP 421 635; U.S. Pat. No. 6,231,864). HBcAg contains a long arginine tail (Pumpens, P. and Grens, E., Intervirology 44:98-114 (2001)) which is dispensable for capsid assembly and capable of binding nucleic acids (Pumpens, P. and Grens, E., Intervirology 44:98-114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in *E. coli*. Specific examples of bacteriophage coat proteins which can be used to prepare compositions of the invention include the coat proteins of RNA bacteriophages such as bacteriophage Qβ (SEQ ID NO: 10; PIR Database, Accession No. VCBPQβ referring to Qβ CP and SEQ ID NO: 11; Accession No. AAA16663 referring to Qβ A1 protein) and bacteriophage fr (SEQ ID NO: 13; PIR Accession No. VCBPFR).

In another preferred embodiment, the at least one MelanA peptide analogue is fused to a Qβ coat protein. Fusion protein constructs wherein epitopes have been fused to the C-terminus of a truncated form of the A1 protein of Qβ, or inserted within the A1 protein have been described (Kozlovska, T. M., et al., Intervirology, 39:9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins. The part of the A1 gene, 3' of the UGA amber codon encodes the CP extension, which has a length of 195 amino acids. Insertion of the at least one MelanA peptide analogue between position 72 and 73 of the CP extension leads to further embodiments of the invention (Kozlovska, T. M., et al., Intervirology 39:9-15 (1996)). Fusion of an MelanA peptide analogue at the C-terminus of a C-terminally truncated Qβ A1 protein leads to further preferred embodiments of the invention. For example, Kozlovska et al., (Intervirology, 39: 9-15 (1996)) describe Qβ A1 protein fusions where the epitope is fused at the C-terminus of the Qβ CP extension truncated at position 19.

As described by Kozlovska et al. (Intervirology, 39: 9-15 (1996)), assembly of the particles displaying the fused epitopes may require the presence of both the A1 protein-MelanA-peptide-analogue fusion and the wt CP to form a mosaic particle. However, embodiments comprising virus-like particles, and hereby in particular the VLPs of the RNA phage Qβ coat protein, which are exclusively composed of VLP subunits having at least one MelanA peptide analogue fused thereto, are also within the scope of the present invention.

The production of mosaic particles may be effected in a number of ways. Kozlovska et al., Intervirology, 39:9-15 (1996), describe three methods, which all can be used in the practice of the invention. In the first approach, efficient display of the fused epitope on the VLPs is mediated by the expression of the plasmid encoding the Qβ A1 protein fusion having a UGA stop codon between CP and CP extension in a *E. coli* strain harboring a plasmid encoding a cloned UGA suppressor tRNA which leads to translation of the UGA codon into Trp (pISM3001 plasmid (Smiley B. K., et al., Gene 134:33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid (Kozlovska, T. M., et al., Intervirology 39:9-15 (1996)). In a third approach, CP and the A1 protein-antigen fusion are encoded in a bicistronic manner, operatively linked to a promoter such as the Trp promoter, as described in FIG. 1 of Kozlovska et al., Intervirology, 39:9-15 (1996).

In a further embodiment, the MelanA peptide analogue is inserted between amino acid 2 and 3 (numbering of the cleaved CP, that is wherein the N-terminal methionine is cleaved) of the fr CP, thus leading to an MelanA peptide analogue—fr CP fusion protein. Vectors and expression systems for construction and expression of fr CP fusion proteins self-assembling to VLP and useful in the practice of the invention have been described (Pushko P. et al., Prot. Eng. 6:883-891 (1993)). In a specific embodiment, the MelanA peptide analogue sequence is inserted into a deletion variant of the fr CP after amino acid 2, wherein residues 3 and 4 of the fr CP have been deleted.

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of the MelanA peptide analogue of the invention by insertion or substitution into the coat protein of MS-2 RNA phage is also falling under the scope of the invention.

In another embodiment of the invention, the MelanA peptide analogues of the invention is fused to a capsid protein of papillomavirus. In a more specific embodiment, the MelanA peptide analogues of the invention is fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., Proc. Natl. Acad. Sci.USA 96:2373-2378 (1999), WO 00/23955). Substitution of amino acids 130-136 of BPV-1 L1 with an MelanA peptide analogues of the invention leads to a BPV-1 L1-MelanA-peptide-analogue fusion protein, which is a preferred embodiment of the invention. Cloning in a baculovirus vector and expression in baculovirus infected Sf9 cells has been described, and can be used in the practice of the invention (Chackerian, B. et al., Proc. Natl. Acad. Sci.USA 96:2373-2378 (1999), WO 00/23955). Purification of the assembled particles displaying the fused MelanA peptide analogues of the invention can be performed in a number of ways, such as for example gel filtration or sucrose gradient ultracentrifugation (Chackerian, B. et al., Proc. Natl. Acad. Sci.USA 96:2373-2378 (1999), WO 00/23955).

In a further embodiment of the invention, the MelanA peptide analogues of the invention are fused to a Ty protein capable of being incorporated into a Ty VLP. In a more specific embodiment, the MelanA peptide analogues of the invention are fused to the p1 or capsid protein encoded by the TYA gene (Roth, J. F., Yeast 16:785-795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in The molecular and Cellular Biology of the Yeast *Saccharomyces*: Genome dynamics, Protein Synthesis, and Energetics, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., Nature 329:68-70 (1987)). So, for example, a MelanA peptide analogue of the invention may be fused to p1 by inserting a sequence coding for the MelanA peptide analogue into the BamH1 site of the pMA5620 plasmid. The cloning of sequences coding for foreign epitopes into the pMA5620 vector leads to expression of fusion proteins comprising amino acids 1-381 of p1 of Ty1-15, fused C-terminally to the N-terminus of the foreign epitope. Likewise, N-terminal fusion of a MelanA peptide analogues of the invention, or internal insertion into the p1 sequence, or substitution of part of the p1 sequence are also meant to fall within the scope of the invention. In particular, insertion of MelanA peptide analogues of the invention into the Ty sequence between amino acids 30-31, 67-68, 113-114 and 132-133 of the Ty protein p1 (EP06771 11) leads to preferred embodiments of the invention.

Further VLPs suitable for fusion of MelanA or MelanA peptide analogues of the invention are, for example, Retrovirus-like-particles (WO9630523), HIV2 Gag (Kang, Y. C., et al, Biol. Chem. 380:353-364 (1999)), Cowpea Mosaic Virus (Taylor, K. M. et al., Biol. Chem. 380:387-392 (1999)), parvovirus VP2 VLP (Rueda, P. et al., Virology 263:89-99 (1999)), HBsAg (U.S. Pat. No. 4,722,840, EP0201416B1).

Examples of chimeric VLPs suitable for the practice of the invention are also those described in Intervirology 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs are also within the scope of the present invention.

As indicated, embodiments comprising antigens fused to the virus-like particle by insertion within the sequence of the virus-like particle building monomer are also within the scope of the present invention. In some cases, antigens can be inserted in a form of the virus-like particle building monomer containing deletions. In these cases, the virus-like particle building monomer may not be able to form virus-like structures in the absence of the inserted antigen.

In some instances, recombinant DNA technology can be utilized to fuse a heterologous protein to a VLP protein (Kratz, P. A., et al., Proc. Natl. Acad. Sci. USA 96:1915 (1999)). For example, the present invention encompasses VLPs recombinantly fused or chemically conjugated (including both covalently and non covalently conjugations) to an antigen (or portion thereof, preferably at least 10, 20 or 50 amino acids) of the present invention to generate fusion proteins or conjugates. The fusion does not necessarily need to be direct, but can occur through linker sequences. More generally, in the case that epitopes, either fused, conjugated or otherwise attached to the virus-like particle, are used as antigens in accordance with the invention, spacer or linker sequences are typically added at one or both ends of the epitopes. Such linker sequences preferably comprise sequences recognized by the proteasome, proteases of the endosomes or other vesicular compartment of the cell.

One way of coupling is by a peptide bond, in which the conjugate can be a contiguous polypeptide, i.e. a fusion protein. In a fusion protein according to the present invention, different peptides or polypeptides are linked in frame to each other to form a contiguous polypeptide. Thus a first portion of the fusion protein comprises an antigen or immunogen and a second portion of the fusion protein, either N-terminal or C-terminal to the first portion, comprises a VLP. Alternatively, internal insertion into the VLP, with optional linking sequences on both ends of the antigen, can also be used in accordance with the present invention.

When HBcAg is used as the VLP, it is preferred that the antigen is linked to the C-terminal end of the HBcAg particle. The hepatitis B core antigen (HBcAg) exhibiting a C-terminal fusion of the MHC class I restricted peptide p33 derived from lymphocytic choriomeningitis virus (LCMV) glycoprotein can be and was typically used as a model antigen (HBcAg-p33). The 185 amino acids long wild type HBc protein assembles into highly structured particles composed of 180 subunits assuming icosahedral geometry. The flexibility of the HBcAg and other VLPs in accepting relatively large insertions of foreign sequences at different positions while retaining the capacity to form structured capsids is well documented in the literature. This makes the HBc VLPs attractive candidates for the design of non-replicating vaccines.

A flexible linker sequence (e.g. a polyglycine/polyserine-containing sequence such as [Gly4 Ser]2 (Huston et al., Meth. Enzymol 203:46-88 (1991)) can be inserted into the fusion protein between the antigen and ligand. Also, the fusion protein can be constructed to contain an "epitope tag", which allows the fusion protein to bind an antibody (e.g. monoclonal antibody) for example for labeling or purification purposes. An example of an epitope tag is a Glu-Glu-Phe tripeptide which is recognized by the monoclonal antibody YL1/2.

The invention also relates to the chimeric DNA which contains a sequence coding for the VLP and a sequence coding for the MelanA peptide analogue. The DNA can be expressed, for example, in insect cells transformed with Baculoviruses, in yeast or in bacteria. There are no restrictions regarding the expression system, of which a large selection is available for routine use. Preferably, a system is used which allows expression of the proteins in large amounts. In general, bacterial expression systems are preferred on account of their efficiency. One example of a bacterial expression system suitable for use within the scope of the present invention is the one described by Clarke et al., J. Gen. Virol. 71: 1109-1117 (1990); Borisova et al., J. Virol. 67: 3696-3701 (1993); and Studier et al., Methods Enzymol. 185:60-89 (1990). An example of a suitable yeast expression system is the one described by Emr, Methods Enzymol. 185:231-3 (1990); Baculovirus systems, which have previously been used for preparing capsid proteins, are also suitable. Constitutive or inducible expression systems can be used. By the choice and possible modification of available expression systems it is possible to control the form in which the proteins are obtained.

In a specific embodiment of the invention, the antigen to which an enhanced immune response is desired is coupled, fused or otherwise attached in frame to the Hepatitis B virus capsid (core) protein (HBcAg). However, it will be clear to all individuals in the art that other virus-like particles can be utilized in the fusion protein construct of the invention.

In a further preferred embodiment of the present invention, the at least one MelanA peptide analogue is bound to the virus-like particle by at least one covalent bond. Preferably, the least one MelanA peptide analogue is bound to the virus-like particle by at least one covalent bond, said covalent bond being a non-peptide bond leading to an ordered and repetitive array and a MelanA peptide analogue—VLP conjugate, respectively. This MelanA peptide analogue array and conjugate, respectively, has typically and preferably a repetitive and ordered structure since the at least one MelanA peptide analogue is bound to the VLP in an oriented manner. Preferably, equal and more than 120, more preferably equal and more than 180, even more preferably more than 270, and again more preferably equal and more than 360 MelanA-peptides of the invention are bound to the VLP. The formation of a repetitive and ordered MelanA peptide analogue—VLP array and conjugate, respectively, is ensured by an oriented and directed as well as defined binding and attachment, respectively, of the at least one MelanA peptide analogue to the VLP as will become apparent in the following. Furthermore, the typical inherent highly repetitive and organized structure of the VLPs advantageously contributes to the display of the MelanA peptide analogue in a highly ordered and repetitive fashion leading to a highly organized and repetitive MelanA peptide analogue—VLP array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of the particle in an expression host guaranteeing proper folding and assembly of the VLP, to which the antigen, i.e. the at least one MelanA peptide analogue of the invention, is then further coupled The present invention discloses methods of binding or association of MelanA peptide analogue of the invention to VLPs. As indicated, in one aspect of the invention, the at least one MelanA peptide analogue of the invention is bound to the VLP by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the VLP or at least one VLP subunit, and a further functional group which can react with a preferred second attachment site, i.e. a cysteine residue fused to the MelanA peptide analogue of the invention and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the MelanA peptide analogue of the invention is reacted with the activated VLP, and this step is typically called the coupling step. Unreacted MelanA peptide analogue may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the MelanA peptide analogue and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigens or antigenic determinants per subunits of the VLP can be adjusted by varying the experimental conditions described above to match the requirements of the vaccine.

A particularly favored method of binding of antigens or antigenic determinants to the VLP, is the linking of a lysine residue on the surface of the VLP with a cysteine residue on the MelanA peptide analogue of the invention. In some embodiments, fusion, coupling, attachment or binding of an amino acid linker containing a cysteine residue, as a second attachment site or as a part thereof, to the MelanA peptide analogue of the invention for coupling to the VLP may be required. Such constructs comprising said amino acid linker may also be obtained by simple peptide syntheses known in the art.

Therefore, in a further preferred embodiment of the present invention, the antigen or antigenic determinant further comprises an amino acid linker, wherein preferably said amino acid linker comprises, or alternatively consists of, a second attachment site.

In general, flexible amino acid linkers are favored. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) (G)kC(G)n with n=0-12 and k=0-5; (g) N-terminal glycine-serine linkers; (h) (G)kC(G)m(S)l (GGGGS)n with n=0-3, k=0-5, m=0-10, l=0-2 (SEQ ID NO: 62); (i) GGC; (k) GGC-NH2; (l) C-terminal gamma 1-linker; (m) C-terminal gamma 3-linker; (n) C-terminal glycine linkers; (o) (G)nC(G)k with n=0-12 and k=0-5; (p) C-terminal glycine-serine linkers; (q) (G)m(S)l(GGGGS)n(G)oC(G)k with n=0-3, k=0-5, m=0-10, l=0-2, and o=0-8 (SEQ ID NO: 63).

Further examples of amino acid linkers are the hinge region of Immunoglobulins, glycine serine linkers (GGGGS)n (SEQ ID NO: 64), and glycine linkers (G)n all further containing a cysteine residue as second attachment site and optionally further glycine residues. Typically preferred examples of said amino acid linkers are N-terminal gamma1: CGDKTHTSPP (SEQ ID NO: 65); C-terminal gamma 1: DKTHTSPPCG (SEQ ID NO: 66); N-terminal gamma 3: CGGPKPSTPPGSSGGAP (SEQ ID NO: 67); C-terminal gamma 3: PKPSTPPGSSGGAPGGCG (SEQ ID NO: 68); N-terminal glycine linker: GCGGGG (SEQ ID NO: 69); C-terminal glycine linker: GGGGCG (SEQ ID NO: 70); C-terminal glycine-lysine linker: GGKKGC (SEQ ID NO: 71); N-terminal glycine-lysine linker: CGKKGG (SEQ ID NO: 72).

Other amino acid linkers particularly suitable in the practice of the invention, when a hydrophobic antigen or antigenic determinant is bound to a VLP, are CGKKGG (SEQ ID NO: 73), or CGDEGG (SEQ ID NO: 74) for N-terminal linkers, or GGKKGC (SEQ ID NO: 75) and GGEDGC (SEQ ID NO: 76), for the C-terminal linkers. For the C-terminal linkers, the terminal cysteine is optionally C-terminally amidated.

Further linkers useful for this invention are amino acid sequences that allow the release of the antigenic peptide, i.e. the human melanoma MelanA peptide analogue, from the VLP. Examples for these linkers are described in Toes R E et al. J Exp Med. 2001 Jul. 2;194(1):1-12. Moreover, the PAProC- a prediction algorithm for proteasomal cleavages might be used (Nussbaum A K, et. al. Immunogenetics. 2001 Mar;53(2):87-94) for prediction of aforementioned amino acid sequences that allow the release of the antigenic peptide, i.e. the human melanoma MelanA peptide analogue, from the VLP.

In preferred embodiments of the present invention, GGCG (SEQ ID NO: 77), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In the most preferred embodiment of the invention, the amino acid linker GGC-NH2 is fused to the C-terminus of the MelanA peptide analogue of the invention.

The cysteine residue added to the MelanA peptide analogue of the invention has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required. Low concentrations of reducing agent are compatible with coupling as described in WO 02/05690, higher concentrations inhibit the coupling reaction, as a skilled artisan would know, in which case the reductand has to be removed or its concentration decreased prior to coupling, e.g. by dialysis, gel filtration or reverse phase HPLC.

Binding of the MelanA peptide analogue of the invention to the VLP by using a hetero-bifunctional cross-linker according to the preferred methods described above, allows coupling of the MelanA peptide analogue of the invention to the VLP in an oriented fashion. Other methods of binding the MelanA peptide analogue of the invention to the VLP include methods wherein the MelanA peptide analogue of the invention is cross-linked to the VLP using the carbodiimide EDC, and NHS. In further methods, the MelanA peptide analogue of the invention is attached to the VLP using a homo-bifunctional cross-linker such as glutaraldehyde, DSG, BM[PEO]4, BS3, (Pierce Chemical Company, Rockford, Ill., USA) or other known homo-bifunctional cross-linkers with functional groups reactive towards amine groups or carboxyl groups of the VLP.

Other methods of binding the VLP to an MelanA peptide analogue of the invention include methods where the VLP is biotinylated, and the MelanA peptide analogue of the invention expressed as a streptavidin-fusion protein, or methods wherein both the MelanA peptide analogue of the invention and the VLP are biotinylated, for example as described in WO 00/23955. In this case, the MelanA peptide analogue of the invention may be first bound to streptavidin or avidin by adjusting the ratio of MelanA peptide analogue of the invention to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the MelanA peptide analogue of the invention, may be used as binding agents for binding MelanA peptide analogue of the invention to the VLP. Alternatively, either the ligand or the receptor may be fused to the MelanA peptide analogue of the invention, and so mediate binding to the VLP chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. one or several antigens or antigenic determinants, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least one MelanA peptide analogue of the invention to the virus-like particle is by way of interaction and association, respectively, between at least one first attachment site of the virus-like particle and at least one second attachment of the MelanA peptide analogue of the invention.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the MelanA peptide analogue of the invention is bound via a cysteine residue, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows to achieve very high epitope density. In particular, a density of more than 1.5 epitopes per subunit has been reached by coupling a peptide to the VLP of Qβ coat protein (e.g. the human Aβ 1-6 peptide as described in WO 2004/016282). The preparation of compositions of VLPs of RNA phage coat proteins with a high epitope density can be effected using the teaching of this application. In prefered embodiment of the invention, when a MelanA peptide analogue of the invention is coupled to the VLP of Qβ coat protein, an average number of MelanA peptide analogue of the invention per subunit of 0.5, 0.6, 0.7, 0.8, 0.9, 1.0, 1.1, 1.2, 1.3, 1.4, 1.5, 1.6 , 1.7, 1.8, 1.9, 2.0, 2.1, 2.2, 2.3, 2.4 2.5, 2.6, 2.7, 2.8, 2.9, or higher is preferred.

The second attachment site, as defined herein, may be either naturally or non-naturally present with the MelanA peptide analogue of the invention. In the case of the absence of a suitable natural occurring second attachment site on the MelanA peptide analogue of the invention, such a, then non-natural second attachment can be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO:20), Qβ-250 (Lys 2-Arg, Lys13-Arg; SEQ ID NO: 22) and Qβ-259 (Lys 2-Arg, Lys16-Arg; SEQ ID NO:24). The constructs were cloned, the proteins expressed, the VLPs purified and used for coupling to MelanA peptide analogues of the invention. Qβ-251; (SEQ ID NO: 23) was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO: 21), was cloned, the protein expressed, and the capsid or VLP isolated and purified, showing that introduction of the additional lysine residue is compatible with self-assembly of the subunits to a capsid or VLP. Thus, MelanA peptide analogue arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue added to the antigen. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductand, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in WO 02/056905, higher concentrations inhibit the coupling reaction, as a skilled artisan would know, in which case the reductand has to be removed or its concentration decreased, e.g. by dialysis, gel filtration or reverse phase HPLC . Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GMBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibility to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction, with e.g. 2-mercaptoethylamine, TCEP, β-mercaptoethanol or DTT. Mild reduction conditions not affecting the immunogenicity of the antigen will be chosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In very preferred embodiments, the MelanA peptide analogue of the invention comprises an added single second attachment site or a single reactive attachment site capable of association with the first attachment sites on the core particle and the VLPs or VLP subunits, respectively. This further ensures a defined and uniform binding and association, respectively, of the at least one, but typically more than one, preferably more than 10, 20, 40, 80, 120, 150, 180, 210, 240, 270, 300, 360, 400, 450 MelanA peptide analogue of the invention to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine—(as the first attachment site) and cysteine—(as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the MelanA peptide analogue of the invention require the fusion of an amino acid linker containing an amino acid suitable as second attachment site according to the disclosures of this invention. Therefore, in a preferred embodiment of the present invention, an amino acid linker is bound to the MelanA peptide analogue of the invention by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already been mentioned above.

In another specific embodiment of the invention, the attachment site is selected to be a lysine or cysteine residue that is fused in frame to the HBcAg. In a preferred embodiment, the antigen is fused to the C-terminus of HBcAg via a three leucine linker.

When an antigen or antigenic determinant is linked to the VLP through a lysine residue, it may be advantageous to either substitute or delete one or more of the naturally resident lysine residues, as well as other lysine residues present in HBcAg variants.

In many instances, when the naturally resident lysine residues are eliminated, another lysine will be introduced into the HBcAg as an attachment site for an antigen or antigenic determinant. Methods for inserting such a lysine residue are known in the art. Lysine residues may also be added without removing existing lysine residues.

The C terminus of the HBcAg has been shown to direct nuclear localization of this protein. (Eckhardt et al., J. Virol. 65:575 582 (1991)). Further, this region of the protein is also believed to confer upon the HBcAg the ability to bind nucleic acids.

As indicated, HBcAgs suitable for use in the practice of the present invention also include N terminal truncation mutants. Suitable truncation mutants include modified HBcAgs where 1, 2, 5, 7, 9, 10, 12, 14, 15, or 17 amino acids have been removed from the N terminus. However, variants of virus-like particles containing internal deletions within the sequence of the subunit composing the virus-like particle are also suitable in accordance with the present invention, provided their compatibility with the ordered or particulate structure of the virus-like particle. For example, internal deletions within the sequence of the HBcAg are suitable (Preikschat, P., et al., J. Gen. Virol. 80:1777-1788 (1999)).

Further HBcAgs suitable for use in the practice of the present invention include N- and C terminal truncation mutants. Suitable truncation mutants include HBcAgs where 1, 2, 5, 7, 9, 10, 12, 14, 15, and 17 amino acids have been removed from the N terminus and 1, 5, 10, 15, 20, 25, 30, 34, 35, 36, 37, 38, 39 40, 41, 42 or 48 amino acids have been removed from the C terminus.

Vaccine compositions of the invention can comprise mixtures of different HBcAgs. Thus, these vaccine compositions can be composed of HBcAgs which differ in amino acid sequence. For example, vaccine compositions could be prepared comprising a "wild type" HBcAg and a modified HBcAg in which one or more amino acid residues have been altered (e.g., deleted, inserted or substituted). In most applications, however, only one type of a HBcAg will be used.

In a preferred embodiment, the virus-like particle comprises at least one first attachment site and the antigen or antigenic determinant comprises at least one second attachment site. Preferably, the first attachment site comprises, or preferably consists of, an amino group or a lysine residue. The second attachment site is preferably selected from the group consisting of (a) an attachment site not naturally occurring with said antigen or antigenic determinant; and (b) an attachment site naturally occurring with said antigen or antigenic determinant. Even more preferably, the second attachment site comprises, or preferably consists of, a sulfhydryl group or a cysteine residue. In a preferred embodiment, the binding of the antigen or antigenic determinant to the virus-like particle is effected through association between the first attachment site and the second attachment site, wherein preferably the association is through at least one non-peptide bond, and wherein preferably the antigen or antigenic determinant and the virus-like particle interact through said association to form an ordered and repetitive antigen array. In one embodiment, the first attachment site is a lysine residue and the second attachment site is a cysteine residue. In another embodiment, the first attachment site is an amino group and the second attachment site is a sulfhydryl group.

In a specific embodiment of the invention, the antigen, and herein in particular, the melanoma MelanA peptide analogue, comprises one or more cytotoxic T cell epitopes, Th cell epitopes, or a combination of the two epitopes. Thus, in one embodiment, the antigen or antigenic determinant comprises one, two, or more cytotoxic T cell epitopes. In another embodiment, the antigen or antigenic determinant comprises one, two, or more Th cell epitopes. In yet another embodiment, the antigen or antigenic determinant comprises one, two or more cytotoxic T cell epitopes and one, two or more Th cell epitopes.

The natural MelanA/Mart-1 epitopes, and for example the MelanA/Mart-1 26-35 epitope bind with low affinity to human HLA-2 only. Thus, in vivo presentation of the natural MelanA epitopes and peptides, respectively, upon vaccination may be a limiting factor. This is particularly important if Melan A epitopes and peptides, respectively, bound, coupled or fused to VLPs are used for vaccination, since under these conditions, MelanA peptides load HLA molecules by cross-presentation. The process of cross-presentation is, however, not as efficient as classical pathways of antigen presentation and the affinity of the MelanA peptide for HLA is even more important. Thus, for VLP-based vaccinations, it is very preferable to use MelanA peptide analogues that bind with relatively high affinity to HLA. Similarly, it may also be advantageous to use MelanA peptide analogues that are recognized with higher affinity by the natural T cell repertoire of the host. As a general rule, MelanA epitopes and peptide analogues, respectively, are preferred that contain anchor residues at the proper positions allowing for efficient binding to MHC molecules.

Therefore, a further aspect of the present invention and a very preferred embodiment of the present invention is to provide a composition for enhancing an immune response in an animal comprising (a) a virus-like particle; and (b) an immunostimulatory substance, wherein said immunostimulatory substance is bound to said virus-like particle, and wherein said composition further comprises at least one antigen or antigenic determinant, wherein said antigen or antigenic determinant is bound to said virus-like particle, and wherein said at least one antigen or antigenic determinant comprises, alternatively consists essentially of, or alternatively consists of a human melanoma MelanA peptide analogue, and wherein said human melanoma MelanA peptide analogue is bound to said virus-like particle.

In a preferred embodiment of the present invention, the Melan A peptide analogue is capable of allowing an efficient binding to MHC molecules. The use of a MelanA peptide analogue, thus, allows, in particular, the introduction of such anchor residues leading to an improved binding to MHC molecules. The introduction of such anchor residues leading to an improved binding to MHC molecules is in particular advantageous, if the natural and normal, respectively, MelanA peptide does not contain such anchor residues or does not contains only such anchor residues which are inferior to the newly introduced anchor residue(s) replacing the natural and normal, respectively anchor residue.

The modification of the normal human MelanA peptide leading to the MelanA peptide analogue, and hereby preferably the introduction of these anchor residues is effected either by (i) induced mutation (e.g. chemical induction, irradiation or other procedures known to a person skilled in the art) and subsequent selection of modified peptides with improved binding to MHC or (ii) of selection of modified peptides with improved binding to MHC arising from natural mutations arising at any level of protein sythesis, including but not limited to mutations arising at the DNA, transcriptional, RNA or translational level of protein expression or (iii) or by systematic or random amino acid exchanges, deletions, substitutions or insertions by using classical peptide synthesis known by the person skilled in the art. The identification of such anchor residues is typically and preferably effected by using the SYFPEITHI database as described by Rammensee et al. in Immunogenetics 50:213-219 (1999). The SYFPEITHI database allows calculating the efficiency of HLA binding for any peptide of choice and it is possible to optimize the peptides regarding the efficiency of HLA binding using this program. Alternatively, identification of preferred peptide analogues can be achieved by MHC-peptide binding assays involving but not limited to whole cell assays of T cell activation or recognition or MHC upregualtion in mutant cell lines, MHC-tetramer-peptide binding assays, competitive binding assays with labelled peptides, surface plasmon resonance assays, all known to the person skilled in the art.

In a further preferred embodiment of the present invention, the MelanA peptide analogue is characterized by two, more preferably by a single amino acid substitution with respect to the corresponding normal MelanA peptide.

In another preferred embodiment of the present invention, the MelanA peptide analogue is protected from protease or peptidase mediated degradation. The use of MelanA peptide analogues that are protected from protease or peptidase degradation leads to increased stability of the peptide in vivo after application of the peptide to a subject or and/or to increased stability of the peptide during storage in the presence of proteases or peptidases. The consequence of this increased stability is more efficient and prolonged presentation of the human melanoma MelanA peptide analogue on MHC and thus the enhanced stimulation of a specific T cell response.

Preferably, the human MelanA peptide analogue is protected by substitution of selected amino acid residues of the natural human MelanA peptide by non natural amino acid derivatives as exemplified in Blanchet et al, J. Immunol. 167: 5852-5861 (2001) and references cited therein. This overcomes the limitation typically imposed by the fact that chemically modified MelanA peptides and MelanA peptide analogues, respectively, may not be recognized by the T cells equally well as compared to the natural and normal, respectively, MelanA peptide.

In another preferred embodiment, the antigen comprises, alternatively consists essentially of, or alternatively consists of a human melanoma MelanA/MART-1 peptide analogue having an amino acid sequence which is selected without limitation from the group consisting of (a) LAGIGILTV (SEQ ID NO: 84); (b) MAGIGILTV (SEQ ID NO: 85), (c) EAMGIGILTV (SEQ ID NO: 86), (d) ELAGIGILTV (SEQ ID NO: 50), (e) EMAGIGILTV (SEQ ID NO: 87), (f) YAAGIGILTV (SEQ ID NO: 88), (g) FAAGIGILTV (SEQ ID NO: 89), (h) GHGHSYTTAE ELAGIGILTV (SEQ ID NO: 51), (i) SYTTAEELAGIGILTVILGVL (SEQ ID NO: 52), and (j) ELAGIGILTVILGVL (SEQ ID NO: 53). In a very preferred embodiment, the antigen comprises, alternatively consists essentially of, or alternatively consists of a human melanoma MelanA/MART-1 peptide analogue having an amino acid sequence which is selected without limitation from the group consisting of (a) LAGIGILTV (SEQ ID NO: 84); (b) MAGIGILTV (SEQ ID NO: 85), (c) EAMGIGILTV (SEQ ID NO: 86), (d) ELAGIGILTV (SEQ ID NO: 50), (e) EMAGIGILTV (SEQ ID NO: 87), (f) YAAGIGILTV (SEQ ID NO: 88), and (g) FAAGIGILTV (SEQ ID NO: 89). These peptide analogues as well as their synthesies have been described by Valmori at al., J. Immunol. 160: 1750-1758 (1998). These peptide analogues show increased relative recognition and target cell lysis by five different cytotoxic T cell clones raised against the natural melanoma peptides.

In a very preferred embodiment of the present invention the human melanoma MelanA/MART-1 peptide analogue comprises, alternatively consists essentially of, or alternatively consists of the sequence ELAGIGILTV (SEQ ID NO: 50). As indicated throughout the examples this very preferred embodiment induces expansion of functional MelanA-specific CD8+T cells in HLA-A2 transgenic mice and represents a good compromise between HLA-binding and TCR-recognition (cf. Valmori at al., J. Immunol. 160: 1750-1758 (1998)).

In a further preferred embodiment of the present invention the human melanoma MelanA/MART-1 peptide analogue with the second attachment site has an amino acid sequence selected without limitation from the group consisting of (a) CGHGHSYTTAE EAAGIGILTV (SEQ ID NO: 54); and typically abbreviated herein as 16-35, (b) CGHGHSYTTAEELAGIGILTV (SEQ ID NO: 55); and typically abbreviated herein as MelanA 16-35 A/L), (c) CGGEAAGIGILTV (SEQ ID NO: 56); and typically abbreviated herein as MelanA 26-35, (d) CGGELAGIGILTV (SEQ ID NO: 57); and typically abbreviated herein as MelanA 26-35 A/L), (e) CSYTTAEELAGIGILTVILGVL (SEQ ID NO: 58); and typically abbreviated herein as MelanA 20-40 A/L), (f) CGGELAGIGILTVILGVL (SEQ ID NO: 59); and typically abbreviated herein as MelanA 26-40 A/L), (g) ELAGIGILTVGGC (SEQ ID NO: 60); and typically abbreviated herein as MelanA 26-35-C A/L), (h) CSPKSLELAGIGILTV (SEQ ID NO: 92), and typically abbreviated herein as CSPKSL-MelanA 26-35 A/L; and (i) ELAGIGILTVILGVLGGC (SEQ ID NO: 93), and typically abbreviated herein as MelanA 26-40-C A/L. In a very preferred embodiment of the present invention the human melanoma MelanA/MART-1 peptide analogue with the second attachment site has an amino acid sequence selected from (a) CGHGHSYTTAEELAGIGILTV (SEQ ID NO: 55); and typically abbreviated herein as MelanA 16-35 A/L), (b) CGGELAGIGILTV (SEQ ID NO: 57); and typically abbreviated herein as MelanA 26-35 A/L), (c) CSYTTAEELAGIGILTVILGVL (SEQ ID NO: 58); and typically abbreviated herein as MelanA 20-40 A/L), (d) CGGELAGIGILTVILGVL (SEQ ID NO: 59); and typically abbreviated herein as MelanA 26-40 A/L), (e) ELAGIGILTVGGC (SEQ ID NO: 60); and typically abbreviated herein as MelanA 26-35-C A/L).

In another very preferred embodiment of the present invention the human melanoma MelanA/MART-1 peptide analogue with the second attachment has an amino acid sequence of CGHGHSYTTAEELAGIGILTV (SEQ ID NO: 55) (MelanA 16-35 A/L). As indicated in Example 21, the inventive vaccine composition comprising this very preferred embodiment, i.e. the Qβ MelanA 16-35 A/L vaccine, is processed by dendritic cells.

In another embodiment of the present invention, the MelanA peptide analogue of the invention, being coupled, fused or otherwise attached to the virus-like particle, is a T cell epitope, either a cytotoxic or a Th cell epitope. In a further preferred embodiment, the antigen is a combination of at least two, being either similar or different, preferably different, epitopes, wherein the at least two epitopes are linked directly or by way of a linking sequence. These epitopes are preferably selected from the group consisting of cytotoxic and Th cell epitopes described for melanomas (gp100, tyrosinase, MAGE-family or NY-ESO-1).

Thus, in a further preferred embodiment of the present invention, said antigen comprises, or alternatively further comprises, a cytotoxic T cell epitope, a Th cell epitope or a combination of at least two of said epitopes, wherein said at least two epitopes are bound directly or by way of a linking sequence, and wherein preferably said cytotoxic T cell epitope is a viral or a tumor cytotoxic T cell epitope.

Preferred cytotoxic T cell epitopes are MelanA epitopes: (16-36 A/L) (25-36 A/L); Tyrosinase epitopes: (1-9) and (368-376) (Panelli, M. C. et.al., J. Immunol., 2000, 164, 495-504); Gp100 epitopes: (154-162), (209-217 (T210M)), (280-288) and (280-288 (A288V)) and (457-466) (Nielsen, M. B. et. al., 2000. J Immunol., 164 (4)., 2287-96 and Linette, G. P. et. al. J Immunol, 2000, 164, 3402-3412 and Skipper, J. C., Int. J. Cancer, 1999, 82, 669-677 and Pass, H. A., et. al., Cancer J Sci Am., 1998, 4, 316-323); TRP2 epitopes: (180-188) (288-296) (455-463) (Sun, Y. et.al., Int. J Cancer, 2000, 87 (3), 399-404 and Parkhurst, M. R. et.al., Cancer Res., 1998, 58, 4895-8901 and Harada, M., et.al., Cancer Res., 2001, 61, 1089-1094)); NY-ESO-1 epitope: 157-165 (Chen, J. L., et. al., J. Immunol, 2000, 165, 948-955); and MAGE-A epitope: (248V9) (Graff-Dubois, S., et.al., 2002, J. Immunol, 169, 575-580)

A preferred combination of cytotoxic T cell epitopes is the combination MelanA (25-36 A/L), Tyrosinase (368-376), Gp100 (209-217 (T210M)) and (457-466), and NY-ESO-1 (157-165).

Preferred Th cell epitopes are Mage-3 epitopes: (281-295), (141-155), and (146-160) (Kobayashi, H., et.al., Cancer Res., 2001, 61, 4773-4778); Tyrosinase epitopes: (188-208), (193-203) (Kobayashi H., et.al., Immunogenetics,1998, 47, 398-403); GP100 epitope: (44-59); and NY-ESO-1 epitopes: (115-132), (121-138), (139-156), (119-143), and (134-148) (Zarour, H. M., et.al., Cancer Res., 2002, 62, 213-218).

Preferred combinations of cytotoxic and Th cell epitopes are MelanA epitopes (1-118 A/L) (SEQ ID NO: 94); NY-ESO-1 epitopes 115-165; or the combination of MelanA (25-36 A7L), gp100 (209-217 (T210M), Mage-3(146-160), and gp100 (44-59).

It should also be understood that a mosaic virus-like particle, e.g. a virus-like particle composed of subunits attached to different antigens and epitopes, respectively, is within the scope of the present invention. Such a composition of the present invention can be, for example, obtained by transforming *E. coli* with two compatible plasmids encoding the subunits composing the virus-like particle fused to different antigens and epitopes, respectively. In this instance, the mosaic virus-like particle is assembled either directly in the cell or after cell lysis. Moreover, such an inventive composition can also be obtained by attaching a mixture of different antigens and epitopes, respectively, to the isolated virus-like particle.

The MelanA peptide analogue of the present invention, and in particular the indicated epitope or epitopes, can be synthesized or recombinantly expressed and coupled to the virus-like particle, or fused to the virus-like particle using recombinant DNA techniques. Exemplary procedures describing the attachment of antigens to virus-like particles are disclosed in WO 00/32227, in WO 01/85208 and in WO 02/056905, the disclosures of which are herewith incorporated by reference in its entirety.

The invention also provides a method of producing a composition for enhancing an immune response in an animal comprising a VLP and an immunostimulatory substance, preferably an unmethylated CpG-containing oligonucleotide bound to the VLP which comprises incubating the VLP with the immunostimulatory substance and oligonucleotide, respectively, adding RNase and purifying said composition. Preferably, the method further comprises the step of binding an antigen or antigenic determinant to said virus-like particle, wherein said antigen comprises, alternatively consists essentially of, or alternatively consists of a human melanoma MelanA peptide analogue. In a preferred embodiment, the anigen or antigenic determinant is bound to the virus-like particle before incubating the virus-like particle with the immunostimulatory substance. In another preferred embodiment, the anigen or antigenic determinant is bound to the virus-like particle after purifying the composition. In an equally preferred embodiment, the method comprises incubating the VLP with RNase, adding the immunostimulatory substance and oligonucleotide, respectively, and purifying the composition. Preferably, the method further comprises the step of binding an antigen or antigenic determinant to said virus-like particle, wherein said antigen comprises, alternatively consists essentially of, or alternatively consists of a human melanoma MelanA peptide analogue. In a preferred embodiment, the anigen or antigenic determinant is bound to the virus-like particle before incubating the virus-like particle with the RNase. In another preferred embodiment, the anigen or antigenic determinant is bound to the virus-like particle after purifying the composition. In one embodiment, the VLP is produced in a bacterial expression system. In another embodiment, the RNase is RNase A.

The invention further provides a method of producing a composition for enhancing an immune response in an animal comprising a VLP bound to an immunostimulatory substance, preferably to an unmethylated CpG-containing oligonucleotide which comprises disassembling the VLP, adding the immunostimulatory substance and oligonucleotide, respectively, and reassembling the VLP. The method can further comprise removing nucleic acids of the disassembled VLP and/or purifying the composition after reassembly. Preferably, the method further comprises the step of binding an antigen or antigenic determinant to the virus-like particle, wherein said antigen comprises, alternatively consists essentially of, or alternatively consists of a human melanoma MelanA peptide analogue. In a preferred embodiment, the anigen or antigenic determinant is bound to the virus-like particle before disassembling the virus-like particle. In another preferred embodiment, the anigen or antigenic determinant is bound to the virus-like particle after reassembling the virus-like particle, and preferably after purifying the composition.

The invention also provides vaccine compositions which can be used for preventing and/or attenuating diseases or conditions. Vaccine compositions of the invention comprise, or alternatively consist of, an immunologically effective amount of the inventive immune enhancing composition together with a pharmaceutically acceptable diluent, carrier or excipient. The vaccine can also optionally comprise an adjuvant.

Thus, in a preferred embodiment, the invention provides a vaccine comprising an immunologically effective amount of the inventive immune response enhancing composition together with a pharmaceutically acceptable diluent, carrier or excipient, wherein the composition comprises, (a) a virus-like particle; (b) at least one immunostimulatory substance; and (c) at least one antigen or antigenic determinant; wherein the antigen or antigenic determinant is bound to the virus-like particle, and wherein the immunostimulatory substance is bound to the virus-like particle, and wherein the antigen comprises, alternatively consists essentially of, or alternatively consists of a human melanoma MelanA peptide analogue. Preferably, the vaccine further comprises an adjuvant.

The invention further provides vaccination methods for preventing and/or attenuating diseases or conditions in animals. In one embodiment, the invention provides vaccines for the prevention of cancer in a wide range of species, particularly mammalian species such as human, monkey, cow, dog, cat, horse, pig, etc., preferably human. Vaccines can be designed to treat all types of cancer, preferably melanomas.

It is well known that homologous prime-boost vaccination strategies with proteins or viruses are most often unsuccessful. Preexisting antibodies, upon re-encountering the antigen, are thought to interfere with the induction of a memory response. To our surprise, the RNA-phage derived VLPs, in particular the VLP derived from Qβ, do very efficiently induce a memory $CD8^+$ T cell response in a homologous prime-boost vaccination scheme. In contrast, as described in Example 26, live vaccinia virus immunizations are very ineffective for the induction of a primary $CD8^+$ T cell response and homologous boosting with vaccinia does hardly lead to an expansion of memory $CD8^+$ T cells.

Therefore, in a further aspect, the invention provides a method of immunizing or treating an animal comprising priming a T cell response in the animal by administering an immunologically effective amount of the inventive vaccine. Preferably, the method further comprises the step of boosting the immune response in the animal, wherein preferably the boosting is effected by administering an immunologically effective amount of a vaccine of the invention or an immunologically effective amount of a heterologous vaccine, wherein even more preferably the heterologous vaccine is a DNA vaccine, peptide vaccine, recombinant virus or a dendritic cell vaccine.

Moreover, in again another aspect, the invention further provides a method of immunizing or treating an animal comprising the steps of priming a T cell response in the animal, and boosting a T cell response in the animal, wherein the boosting is effected by administering an immunologically effective amount of the vaccine of the invention. Preferably, the priming is effected by administering an immunologically effective amount of a vaccine of the invention or an immunologically effective amount of a heterologous vaccine, wherein even more preferably said heterologous vaccine is a DNA vaccine, peptide vaccine, recombinant virus or a dendritic cell vaccine.

Moreover, in again another aspect, the invention further provides for a composition comprising a virus-like particle, at least one immunostimulatory substance; and at least one antigen or antigenic determinant; wherein said antigen or antigenic determinant is bound to said virus-like particle, and wherein said immunostimulatory substance is bound to said virus-like particle, and wherein said antigen comprises a cytotoxic T cell epitope, a Th cell epitope or a combination of at least two of said epitopes, wherein said at least two epitopes are bound directly or by way of a linking sequence, and wherein preferably said cytotoxic T cell epitope is a viral or a tumor cytotoxic T cell epitope.

In again a further aspect, the present invention provides a composition, typically and preferably for enhancing an immune response in an animal comprising: (a) a virus-like particle; (b) an immunostimulatory substance; wherein said immunostimulatory substance (b) is bound to said virus-like particle (a); and (c) an antigen, wherein said antigen is mixed with said virus-like particle (a), and wherein said antigen comprises, alternatively consists essentially of, or alternatively consists of a human melanoma MelanA peptide analogue. As used herein, the term "mixed" refers to the combination of two or more substances, ingredients, or elements that are added together, are not chemically combined with each other and are capable of being separated. Methods of mixing antigens with virus-like particles are described in WO 04/000351, which is incorporated herein by reference in its entirety.

As would be understood by one of ordinary skill in the art, when compositions of the invention are administered to an animal, they can be in a composition which contains salts, buffers, adjuvants or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and Corynebacterium parvum. Such adjuvants are also well known in the art. Further adjuvants that can be administered with the compositions of the invention include, but are not limited to, Monophosphoryl lipid immunomodulator, AdjuVax 100a, QS 21, QS 18, CRL1005, Aluminum salts, MF 59, and Virosomal adjuvant technology. The adjuvants can also comprise a mixture of these substances.

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention can be administered by various methods known in the art. The particular mode selected will depend of course, upon the particular composition selected, the severity of the condition being treated and the dosage required for therapeutic efficacy. The methods of the invention, generally speaking, can be practiced using any mode of administration that is medically acceptable, meaning any mode that produces effective levels of the active compounds without causing clinically unacceptable adverse effects. Such modes of administration include oral, rectal, parenteral, intracistemal, intravaginal, intraperitoneal, topical (as by powders, ointments, drops or transdermal patch), bucal, or as an oral or nasal spray. The term "parenteral" as used herein refers to modes of administration which include intravenous, intramuscular, intraperitoneal, intrasternal, subcutaneous and intraarticular injection and infusion. The composition of the invention can also be injected directly in a lymph node.

Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Combinations can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Dosage levels depend on the mode of administration, the nature of the subject, and the quality of the carrier/adjuvant formulation. Typical amounts are in the range of about 0.1 μg to about 20 mg per subject. Preferred amounts are at least about 1 μg to about 1 mg, more preferably at least about 10 to about 400 μg per subject. Multiple administration to immunize the subject is preferred, and protocols are those standard in the art adapted to the subject in question.

The compositions can conveniently be presented in unit dosage form and can be prepared by any of the methods well-known in the art of pharmacy. Methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration can be presented as discrete units, such as capsules, tablets or lozenges, each containing a predetermined amount of the compositions of the invention. Other compositions include suspensions in aqueous liquids or non-aqueous liquids such as a syrup, an elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art.

Other embodiments of the invention include processes for the production of the compositions of the invention and methods of medical treatment for cancer and allergies using said compositions.

Further aspects and embodiments of the present invention will become apparent in the following examples and the appended claims.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference in their entirety.

EXAMPLE 1

Generation of p33-HBcAg VLPs.

The DNA sequence of HBcAg containing peptide p33 from LCMV is given in SEQ ID NO: 15. The p33-HBcAg VLPs were generated as follows: Hepatitis B clone pEco63 containing the complete viral genome of Hepatitis B virus was purchased from ATCC. The gene encoding HBcAg was introduced into the EcoRI/HindIII restriction sites of expression vector pkk223.3 (Pharmacia) under the control of a strong tac promoter. The p33 peptide (KAVYNFATM) (SEQ ID NO: 80) derived from lymphocytic choriomeningitis virus (LCMV) was fused to the C-terminus of HBcAg (1-185) via a three leucine-linker by standard PCR methods. A clone of *E. coli* K802 selected for good expression was transfected with the plasmid, and cells were grown and resuspended in 5 ml lysis buffer (10 mM Na2HPO4, 30 mM NaCl, 10 mM EDTA, 0.25% Tween-20, pH 7.0). 200 μl of lysozyme solution (20 mg/ml) was added. After sonication, 4 μl Benzonase and 10 mM MgCl2 was added and the suspension was incubation for 30 minutes at RT, centrifuged for 15 minutes at 15,000 rpm at 4° C. and the supernatant was retained.

Next, 20% (w/v) (0.2 g/ml lysate) ammonium sulfate was added to the supernatant. After incubation for 30 minutes on ice and centrifugation for 15 minutes at 20,000 rpm at 4° C. the supernatant was discarded and the pellet resuspended in 2-3 ml PBS. 20 ml of the PBS-solution was loaded onto a Sephacryl S-400 gel filtration column (Amersham Pharmacia Biotechnology AG), fractions were loaded onto a SDS-Page gel and fractions with purified p33-VLP capsids were pooled. Pooled fractions were loaded onto a Hydroxyapatite column. Flow through (which contains purified p33-VLP capsids) was collected and loaded onto a reducing SDS-PAGE gel for monomer molecular weight analysis. Electron microscopy was performed according to standard protocols.

Thus, the structure of the p33-VLPs was assessed by electron microscopy and SDS PAGE. Recombinantly produced HBcAg wild-type VLPs (composed of HBcAg [aa 1-185] monomers) and p33-VLPs were loaded onto a Sephacryl S-400 gel filtration column (Amersham Pharmacia Biotechnology AG) for purification. Pooled fractions were loaded onto a Hydroxyapatite column. Flow through (which contains purified p33-VLPs) was collected and loaded onto a reducing SDS-PAGE gel for monomer molecular weight analysis.

Throughout the description the terms p33-HBcAg VLP, HBcAg-p33 VLP, p33-VLPs and HBc33 are used interchangeably.

EXAMPLE 2

Cloning, Expression and Purification of GA VLP

The cDNA of GA phage coat protein was amplified from GA phage by reverse transcription followed by a PCR amplification step, using the RevertAid First strand cDNA synthesis Kit (Fermentas). The cDNA was cut with the enzymes NcoI and HindIII, and cloned in vector pQβ185 previously cut with the same enzymes, leading to plasmid 355.24, harboring GA cDNA. The sequence of the inserted cDNA was checked by DNA sequencing.

Plasmid 355.24 was transformed in *E. coli* JM109. Expression was performed essentially as described for Qβ VLP. A single colony was inoculated in LB medium containing 20 mg/L Ampicillin overnight without shaking. This inoculum was transferred the next day into a larger flask containing M9 medium supplemented with 1% casaminoacids, 0.2% glucose and 20 mg/L Ampicillin, and incubated under shaking for 14-20 h.

GA VLP was isolated essentially as described for Qβ VLP. Cells were lysed, and the cleared lysate was loaded onto a Sepharose CL-4B column (Amersham Pharmacia). The eluate was concentrated by ammonium sulphate precipitation, and rechromatographed onto a Sepharose CL-6B column (Amersham Pharmacia). The final step was either an ultracentrifugation on sucrose gradient (20-50% w/v), or on CsCl. The isolated VLPs were subsequently dialysed against 20 mM Tris, 150 mM NaCl, pH 8.0.

EXAMPLE 3

Fluorescein Labeled CpG-Containing Oligonucleotides can be Packaged into BKV, HBcAg and Qβ-VLPs.

VLPs produced in yeast contain small amounts of RNA which can be easily digested and so eliminated by incubating the VLPs with RNase A. The highly active RNase A enzyme has a molecular weight of about 14 kDa and is small enough to enter the VLPs to eliminate the undesired ribonucleic acids. Recombinantly produced BKV VLPs (SEQ ID NO: 12) were concentrated to 1 mg/ml in PBS buffer pH7.2 and incubated in the absence or presence of RNase A (200 μg/ml, Roche Diagnostics Ltd, Switzerland) for 3 h at 37° C. After RNase A digestion BKV VLPs were supplemented with 75 nmol/ml 5'-fluorescein labeled phosphorothioate CpG-FAM oligonucleotide (oligonucleotide from SEQ ID NO: 34) and incubated for 3 h at 37° C. Subsequently BKV VLPs were subjected to DNaseI digestion for 3 h at 37° C. (40 u/ml AMPD1, Sigma, Division of Fluka AG, Switzerland) or loaded without DNaseI digestion. The samples were complemented with 6-fold concentrated DNA-loading buffer (10 mM Tris pH7.5, 10% v/v glycerol, 0.4% orange G) and run for 1 h at 65 volts in a 0.8% native tris-acetate pH 7.5 agarose gel. Upon staining with ethidium bromide nucleic acids are detected, while in the absence of ethidium bromide UV excitation leads to fluorescence of the fluorescein-label in the CpG-FAM.

BKV VLPs (15 μg) was analyzed by a native 0.8% agarose gel electrophoresis after control incubation or after digestion with RNase A and subsequent incubation with double stranded (ds) DNA (246 bp) (SEQ ID NO: 17), upon staining with ethidium bromide or Coomassie Blue. The following samples were loaded on the gel: 1: BKV VLPs untreated; 2: BKV VLPs RNase A treated; 3: BKV VLPs treated with RNase A and incubated with dsDNA; lane M: Gene Ruler 1 kb DNA ladder (MBI Fermentas GmbH, Heidelberg, Germany).

BKV VLPs (15 μg) was analyzed by a native 0.8% agarose gel electrophoresis after control incubation or after digestion with RNase A and subsequent incubation with CpG-oligonucleotides (with phosphate- or with phosphorothioate (pt) backbone) upon staining with ethidium bromide or Coomassie Blue. The following samples were loaded on the gel: 1: BKV VLPs stock (PBS/50% glycerol); 2: BKV VLPs untreated (PBS buffer); 3: BKV VLPs RNase A treated; 4: BKV VLPs RNase A treated post- dialysis; 5: BKV VLPs RNase A treated with CpG-oligonucleotides; 6: BKV VLPs RNase A treated with CpG(pt)-oligomers; 7: BKV VLPs RNase A treated with CpG(pt)-oligomers post-dialysis; lane M: Gene Ruler 1 kb DNA ladder (MBI Fermentas GmbH, Heidelberg, Germany).

The RNase A digestion leads to a change in migration of the VLP, visible on Coomassie stained agarose gel, presumably due to the lack of negative charges from the RNA. Addition of CpG-oligonucleotide restores the migration of BKV VLPs and results in a fluorescent band with the same migration as the RNA band present in untreated VLPs. This clearly shows that CpG-FAM oligonucleotides have been packaged into VLPs.

EXAMPLE 4

Large Double Stranded Oligonucleotides can be Packaged into BKV VLPs.

To introduce double stranded (ds) nucleotide sequences, the RNase A treated recombinant BKV VLPs (Example 3) were supplemented with 50 μg/ml (ds) DNA fragments (246 bp in length, dsDNA, SEQ ID NO: 17) and incubated for 3 h at 37° C. The samples were complemented with 6-fold concentrated DNA-loading buffer (10 mM Tris pH8.0, 10% v/v glycerol, 0.4% orange G) and run for 1 h at 65 volts in a 0.8% native tris-acetate pH8.0 agarose gel. BKV VLPs (15 μg) were loaded on a native 0.8% agarose gel electrophoresis and analyzed after control incubation or after digestion with RNase A and subsequent incubation with (ds) DNA upon staining with ethidium bromide or Coomassie Blue in order to assess the presence of RNA/DNA or protein. Packaged DNA molecules are visible in the presence of ethidium bromide as a band with the same migration as the VLP band visualized with Coomassie Blue.

Addition of (ds) DNA restores the migration of BKV VLPs and results in a DNA band with the same migration as the Coomassie Blue stained VLPs. This clearly shows that (ds) DNA has been packaged into BKV VLPs.

EXAMPLE 5

CpG-Containing Oligonucleotides can be Packaged into BKV VLPs.

To introduce immunostimulatory CpG-oligonucleotides, the RNase A treated recombinant BKV VLPs (Example 3) were supplemented with 150 nmol/ml CpG-oligonucleotides CyCpG with phosphodiester backbone or CyCpOpt with phosphorothioate backbone and incubated for 3 h at 37° C. VLP preparations for mouse immunization were extensively dialysed (10,000-fold diluted) for 24 h against PBS pH7.2 with a 300 kDa MWCO dialysis membrane (Spectrum Medical industries Inc., Houston, USA) to eliminate RNase A and the excess of CpG-oligonucleotides. The samples were complemented with 6-fold concentrated DNA-loading buffer (10 mM Tris pH7.5, 10% v/v glycerol, 0.4% orange G) and run for 1 h at 65 volts in a 0.8% native tris-acetate pH7.5 agarose gel. BKV VLPs (15 μg) were loaded on a native 0.8% agarose gel electrophoresis and analyzed after control incubation or after digestion with RNase A and subsequent incubation with CpG-oligonucleotides (with phosphodiester- or with phosphorothioate backbone) upon staining with ethidium bromide or Coomassie Blue in order to assess the presence of RNA/DNA or protein and the reduction of unbound CpG-oligonucleotides after dialysis. Unbound CpG-oligonucleotides are visible as a low molecular weight ethidium bromide stained band. Addition of CpG-oligonucleotides restores the migration of BKV VLPs and results in a DNA band with the same migration as the Coomassie Blue stained VLPs. This clearly shows that CpG-oligonucleotides are packaged into BKV VLPs.

EXAMPLE 6

VLPs Containing CpG-Oligonucleotides (with Phosphorothioate Modification of the Phosphate Backbone) Induce Enhanced Th1 Directed Immune response.

Female BALB/c mice (three mice per group) were subcutaneously injected with 10 μg BKV VLPs containing phosphorothioate CpG-oligonucleotide CyCpGpt (SEQ ID NO: 34). As controls mice were subcutaneously injected with either 10 μg of RNase treated BKV VLPs alone or BKV VLPs mixed with 0.3 nmol or 20 nmol phosphorothioate CpG-oligonucleotides in 200 μl PBS pH7.2 or were left untreated. BKV VLPs were prepared as described in Example 5 and before immunization extensively purified from unbound CpG-oligonucleotide by dialysis. On day 14 after immunization blood was taken and IgG1 and IgG2a antibody response to BKV VLPs was determined (see Table 1).

TABLE 1

Mouse IgG1 and IgG2a OD50% antibody titers to BKV VLPs on day 14 after immunization with BKV VLPs and phosphorothioate (pt) CpG-oligonucleotides.

| OD 50% titer | BKV | BKV plus 0.3 nmol CpG(pt) | BKV plus 20 nmol CpG(pt) | BKV/0.3 nmol CpG(pt) |
|---|---|---|---|---|
| IgG1 | 1015 | 823 | <40 | 340 |
| Stdev | 470 | 412 | 0 | 241 |
| IgG2a | 1190 | 1142 | 4193 | 2596 |
| Stdev | 406 | 1219 | 1137 | 1232 |

Immunization with RNase A treated BKV VLPs containing phosphorothioate CpG-oligonucleotides CyCpGpt results in a decreased IgG1 and an increased anti-BKV VLP IgG2a titer as compared to immunization with the same amount (0.3 nmol) of CpG-oligonucleotides mixed with BKV VLPs or BKV VLPs alone. Mice immunized with BKV VLPs mixed with 20 nmol phosphorothioate CpG-oligonucleotide CyCpGpt show very low IgG1 and high IgG2a titers. The decrease in IgG1 titer and the increase in IgG2a titer as compared to controls demonstrates a Th1 cell directed immune response induced by phosphorothioate CpG-oligonucleotides packaged in BKV VLPs. Table 1 clearly demonstrates the higher potency of BKV VLPs containing CpG-oligonucleotides packaged within the particles as compared to BKV VLPs simply mixed with CpG-oligonucleotides.

EXAMPLE 7

Immunostimulatory nucleic acids can be packaged into HBcAg VLPs comprising fusion proteins with antigens.

HBcAg VLPs, when produced in *E. coli* by expressing the Hepatitis B core antigen fusion protein p33-HBcAg (HBc33) (see Example 1) or the fusion protein to the peptide P1A (HBcP1A), contain RNA which can be digested and so eliminated by incubating the VLPs with RNase A.

The gene P1A codes for a protein that is expressed by the mastocytoma tumor cell line P815. The dominant CTL epitope, termed P1A peptide, binds to MHC class I (Ld) and the complex is recognized by specific CTL clones (Brändle et al., 1998, Eur. J. Immunol. 28: 4010-4019). Fusion of peptide P1A-1 (LPYLGWLVF) ((SEQ ID NO: 90) to the C-terminus of HBcAg (aa 185, see Example 1) was performed by PCR using appropriate primers using standard molecular biology techniques. A three leucine linker was cloned between the HBcAg and the peptide sequence. Expression was performed as described in Example 1. The fusion protein of HBcAg with P1A, termed HBcP1A, formed capsids when expressed in *E. coli* which could be purified similar to the procedure described in Example 1.

Enzymatic RNA hydrolysis: Recombinantly produced HBcAg-p33 (HBc33) and HBcAg-P1A (HBcP1A) VLPs at a concentration of 1.0 mg/ml in 1×PBS buffer (KCl 0.2 g/L, KH2PO4 0.2 g/L, NaCl 8 g/L, Na2HPO4 1.15 g/L) pH 7.4, were incubated in the presence of 300 μg/ml RNase A (Qiagen AG, Switzerland) for 3 h at 37° C. in a thermomixer at 650 rpm.

Packaging of immunostimulatory nucleic acids: After RNA digestion with RNAse A HBcAg-p33 VLPs were supplemented with 130 nmol/ml CpG-oligonucleotides B-CpG, NKCpG, G10-PO (Table 2). Similarly, the 150mer single-stranded Cy150-1 and 253mer double stranded dsCy-CpG-253, both containing multiple copies of CpG motifs, were added at 130 nmol/ml or 1.2 nmol/ml, respectively, and incubated in a thermomixer for 3 h at 37° C. Double stranded CyCpG-253 DNA was produced by cloning a double stranded multimer of CyCpG into the EcoRV site of pBluescript KS-. The resulting plasmid, produced in *E. coli* XL1-blue and isolated using the Qiagen Endofree plasmid Giga Kit, was digested with restriction endonucleases XhoI and XbaI and resulting restriction products were separated by agarose electrophoresis. The 253 bp insert was isolated by electro-elution and ethanol precipitation. Sequence was verified by sequencing of both strands.

TABLE 2

Terminology and sequences of immunostimulatory nucleic acids used in the Examples. Small letters indicate deoxynucleotides connected via phosphorothioate bonds while large letters indicate deoxynucleotides connected via phosphodiester bonds

| Terminology | Sequence | SEQ ID NO |
|---|---|---|
| CyCpGpt | tccatgacgttcctgaataat | 34 |
| CyCpG | TCCATGACGTTCCTGAATAAT | 35 |
| B-CpGpt | tccatgacgttcctgacgtt | 36 |
| B-CpG | TCCATGACGTTCCTGACGTT | 37 |
| NKCpGpt | ggggtcaacgttgaggggg | 38 |
| NKCpG | GGGGTCAACGTTGAGGGGG | 39 |
| CyCpG-rev-pt | attattcaggaacgtcatgga | 40 |
| g10gacga-PO (G10-PO) | GGGGGGGGGGGACGATCGTCGGGGGGGG | 41 |
| g10gacga-PS (G10-PS) | ggggggggggggacgatcgtcgggggggggg | 42 |
| (CpG)20OpA | CGCGCGCGCGCGCGCGCGCGCGCGCGCGCG CGCGCGCGCGAAATGCATGTCAAAGACAGCAT | 43 |
| Cy(CpG)20 | TCCATGACGTTCCTGAATAATCGCGCGCGCG CGCGCGCGCGCGCGCGCGCGCGCGCGCGCG | 44 |
| Cy(CpG)20-OpA | TCCATGACGTTCCTGAATAATCGCGCGCGCG CGCGCGCGCGCGCGCGCGCGCGCGCGCGCGAA ATGCATGTCAAAGACAGCAT | 45 |
| CyOpA | TCCATGACGTTCCTGAATAATAAATGCATGT CAAAGACAGCAT | 46 |
| CyCyCy | TCCATGACGTTCCTGAATAATTCCATGACGT TCCTGAATAATTCCATGACTGGCCTGAATAAT | 47 |
| Cy150-1 | TCCATGACGTTCCTGAATAATTCCATGACGT TCCTGAATAATTCCATGACTGGCCTGAATAA TTGGATGACGTTGGTGAATAATTCCATGACG TTCCTGAATAATTCCATGACGTTCCTGAAAT AATTCCATGACGTTCCTGAATAATTCC | 48 |
| dsCyCpG-253 (complementary strand not shown) | CTAGAACTAGTGGATCCCCCGGGCTGCAGATT CGATTCATGACTTCCTGAATAATTCCATGACG TTGGTGAATAATCCATGACGTTCCTGAATAAT TCCATGACGTTCCTGAATAATTCCAGACGTTC CTGAATAATTCCATGACGTTCCTGAATAATTC CATGACCTCCTGAATAATTCCATGACGTTCCT GAATAATTCCATGACGTTCCTAAAATTCCAAT CAAGCTTATCGATACCGTCGACC | 49 |

DNAse I treatment: Packaged HBcAg-p33 VLPs were subsequently subjected to DNaseI digestion (5 U/ml) for 3 h at 37° C. (DNaseI, RNase free Fluka AG, Switzerland) and were extensively dialysed (2× against 200-fold volume) for 24 h against PBS pH 7.4 with a 300 kDa MWCO dialysis membrane (Spectrum Medical industries Inc., Houston, USA) to eliminate RNAse A and the excess of CpG-oligonucleotides.

Benzonase treatment: Since some single stranded oligodeoxynucleotides were partially resistant to DNaseI treatment, Benzonase treatment was used to eliminate free oligonucleotides from the preparation. 100-120 U/ml Benzonase (Merck KGaA, Darmstadt, Germany) and 5 mM MgCl2 were added and incubated for 3 h at 37° C. before dialysis.

Dialysis: VLP preparations packaged with immunostimulatroy nucleic acids used in mouse immunization experiments were extensively dialysed (2× against 200 fold volume) for 24 h against PBS pH 7.4 with a 300 kDa MWCO dialysis membrane (Spectrum Medical Industries, Houston, US) to eliminate added enzymes and free nucleic acids.

Analytics of packaging: release of packaged immunostimulatory nucleic acids: To 50 μl capsid solution 1 μl of proteinase K (600 U/ml, Roche, Mannheim, Germany), 3 μl 10% SDS-solution and 6 μl 10fold proteinase buffer (0.5 M NaCl, 50 mM EDTA, 0.1 M Tris pH 7.4) were added and subsequently incubated overnight at 37° C. VLPs are completed hydrolysed under these conditions. Proteinase K was inactivated by heating for 20 min at 65° C. 1 μl RNAse A (Qiagen, 100 μg/ml, diluted 250 fold) was added to 25 μl of capsid. 2-30 μg of capsid were mixed with 1 volume of 2× loading buffer (1×TBE, 42% w/v urea, 12% w/v Ficoll, 0.01% Bromphenolblue), heated for 3 min at 95° C. and loaded on a 10% (for oligonucleotides of about 20 nt length) or 15% (for>than 40 mer nucleic acids) TBE/urea polyacrylamid gel (Invitrogen). Alternatively samples were loaded on a 1% agarose gel with 6× loading dye (10 mM Tris pH 7.5, 50 mM EDTA, 10% v/v glycerol, 0.4% orange G). TBE/urea gels were stained with SYBRGold and agarose gels with stained with ethidium bromide.

The oligonucleotides B-CpG, NKCpG and G10-PO were packaged into HBc33. The analysis of B-CpG packaged into HBc33 VLPs was done on a 1% agarose gel stained with ethidium bromide and Coomassie Blue. Loaded on the gel were 50 μg of the following samples: 1. HBc33 VLP untreated; 2. HBc33 VLP treated with RNase A; 3. HBc33 VLP treated with RNase A and packaged with B-CpG; 4. HBc33 VLP treated with RNase A, packaged with B-CpG and treated with DNaseI; 5. HBc33 VLP treated with RNase A, packaged with B-CpG, treated with DNaseI and dialysed; 6.1 kb MBI Fermentas DNA ladder. The amount of packaged B-CpG extracted from the VLP was analyzed on a 1.5% agarose gel stained with ethidium bromide: Loaded on gel were the following samples: 1. 0.5 nmol B-CpG control; 2. 0.5 nmol B-CpG control; 3. B-CpG oligo content HBc33 after phenol/chloroform extraction; 4. B-CpG oligo content HBc33 after phenol/chloroform extraction and RNase A treatment; 5. B-CpG oligo content HBc33 after phenol/chloroform extraction and DNaseI treatment; 6. empty; 7. MBI Fermentas 100 bp DNA ladder.

The analysis of NKCpG packaged into HBc33 VLPs was done on a 1% agarose gel stained with ethidiurn bromide and Coomassie Blue. Loaded on the gel were 15 μg of the following samples: 1. HBc33 VLP untreated; 2. HBc33 VLP treated with RNase A; 3. HBc33 VLP treated with RNase A and packaged with NKCpG; 4. HBc33 VLP treated with RNase A, packaged with NKCpG, treated with DNaseI and dialysed; 5. 1 kb MBI Fermentas DNA ladder. The analysis of the amount of packaged NKCpG extracted from the VLP was analyzed on a 15% TBE/urea gel stained with SYBR Gold. Loaded on gel were the following samples: 1. NKCpG oligo content HBc33 after proteinase K digestion and RNase A treatment; 2. 20 pmol NKCpG control; 3. 10 pmol NKCpG control; 4. 40 pmol NKCpG control.

The analysis of g10gacga-PO packaged into HBc33 VLPs was done on a 1% agarose gel stained with ethidium bromide and Coomassie Blue. Loaded on the gel were 15 μg of the following samples: 1. 1 kb MBI Fermentas DNA ladder; 2. HBc33 VLP untreated; 3. HBc33 VLP treated with RNase A; 4. HBc33 VLP treated with RNase A and packaged with g10gacga-PO; 5. HBc33 VLP treated with RNase A, packaged with g10gacga-PO, treated with Benzonase and dialysed.

RNA content in the VLPs was strongly reduced after RNaseA treatment while most of the capsid migrated as a slow migrating smear presumably due to the removal of the negatively charged RNA. After incubation with an excess of oligonucleotides the capsids contained a higher amount of nucleic acid than the RNAseA treated capsids and therefore migrated at similar velocity as the untreated capsids. Additional treatment with DNAse I or Benzonase degraded the free oligonucleotides while oligonucleotides packaged in the capsids did not degrade, clearly showing packaging of oligonucleotides. In some cases packaging of oligonucleotides was confirmed by proteinase K digestion after DNAseI/Benzonase treatment and dialysis. The finding that oligonucleotides released from the capsid with the procedure described above were of the same size than the oligonucleotide used for packaging clearly demonstrated packaging of oligonucleotides.

Large single-stranded oligonucleotide Cy150-1 was packaged into HBc33. Cy150-1 contains 7.5 repeats of CyCpG and was synthesized according standard oligonucleotide synthesis methods (IBA, Göttingen, Germany). The analysis of Cy150-1 packaged into HBc33 VLPs was analyzed on a 1% agarose gel stained with ethidium bromide and Coomassie Blue. Loaded on the gel were 15 μg of the following samples: 1. 1 kb MBI Fermentas DNA ladder; 2. HBc33 VLP untreated; 3. HBc33 VLP treated with RNase A; 4. HBc33 VLP treated with RNase A and packaged with Cy150-1; 5. HBc33 VLP treated with RNase A, packaged with Cy150-1, treated with DNaseI and dialysed; 6. HBc33 VLP treated with RNase A, packaged with Cy150-1, treated with DNaseI and dialysed. The analysis of the amount of packaged Cy150-1 extracted from the VLP was analyzed on a 10% TBE/urea gel stained with SYBR Gold. Loaded on gel are the following samples: 1. 20 pmol Cy150-1 control; 2. 10 pmol Cy150-1 control; 3. 4 pmol Cy150-1 control; 4. Cy150-1 oligo content of 4 μg HBc33 after 3 min at 95° C. with 1 volume TBE/urea sample buffer. RNA content in the capsid was strongly reduced after RNaseA treatment while most of the capsid migrated as a slow migrating smear. Capsid were diluted with 4 volumes of water and concentrated to 1 mg/ml. After incubation with an excess of Cy150-1 the capsid contained a bigger amount of nucleic acid and thus migrated at similar velocity as the untreated capsids. Additional treatment with DNAseI degraded the free, not packaged oligonucleotides while oligonucleotides in capsids were not degraded. Release of the DNAseI-resistant nucleic acid from the packaged VLPs by heating for 3 min at 95° C. in TBE/urea loading buffer revealed the presence of the 150 mer.

The oligonucleotide NKCpGpt was also packaged into HBcP1A. The analysis of NKCpGpt packaged into HBcP1A VLPs was done on a 1% agarose gel stained with ethidium bromide and Coomassie Blue. Loaded on the gel were 15 μg of the following samples: 1. 1 kb MBI Fermentas DNA ladder; 2. HBcP1A VLP untreated; 3. HBcP1A VLP treated with RNase A; 4. HBcP1A VLP treated with RNase A and packaged with NKCpGpt. Treatment with RNAse reduced nucleic acid content and slowed migration of the capsids. Addition of NKCpGpt restored nucleic acid content in capsids and fast migration.

EXAMPLE 8

Immunostimulatory Nucleic Acids can be Packaged in HBcAg-wt Coupled with Antigens.

Recombinantly produced HBcAg-wt VLPs were packaged after coupling with peptide p33 (CGG-KAVYNFATM) (SEQ ID NO: 81), derived from lymphocytic choriomeningitis virus (LCMV). For coupling HBcAg-wt VLPs (2 mg/ml) were derivatized with 25× molar excess of SMPH (Succinimidyl-6-[(β-maleimido-propionamido)hexanoate], Pierce) for 1 h at 25° C. in a thermomixer. The derivatized VLPs were dialyzed to Mes buffer (2-(N-morpholino) ethanesulphonic acid) pH 7.4 for 2×2 h using MWCO 10.000 kD dialysis membranes at 4° C. VLPs (50 μM) were subsequently coupled to the N-terminal cysteine of the p33 peptide (250 μM) during a 2 h incubation in a thermomixer at 25° C. Samples were dialyzed (MWCO 300.000) extensively to 1× PBS pH 7.4 to eliminate undesired free peptide.

HBcAg-wt VLPs derivatization with SMPH and coupling to p33 peptide was analyzed on SDS-PAGE. Samples were analysed by 16% SDS PAGE and stained with Coomassie Blue. Loaded on the gel were the following samples: 1.NEB Prestained Protein Marker, Broad Range (# 7708S), 10 μl; 2. p33 peptide; 3. HBcAg-wt VLP derivatized with SMPH, before dialysis; 4. HBcAg-wt VLP derivatized with SMPH, after dialysis; 5. HBcAg-wt VLP coupled with p33, supernatant; 6. HBcAg-wt VLP coupled with p33, pellet. HBcAg-wt was visible as a 21 kD protein band. Due to the low molecular weight of SMPH is the derivatised product only slightly larger and can not be distinguished by SDS-PAGE. Peptide alone was visible as a 3 kD band and coupled product, termed HBx33, showed a strong secondary band at approximately 24 kD accounting for more than 50% of total HBcAg-wt.

Enzymatic RNA hydrolysis: HBx33 VLPs (0.5-1.0 mg/ml, 1×PBS buffer pH7.4) in the presence of RNase A (300 μg/ml, Qiagen AG, Switzerland) were diluted with 4 volumes H2O to decrease salt concentration to a final 0.2×PBS concentration and incubated for 3 h at 37° C. in a thermomixer at 650 rpm.

Packaging of immunostimulatory nucleic acids: After RNase A digestion HBx33 VLPs were concentrated using Millipore Microcon or Centriplus concentrators, then supplemented with 130 nmol/ml CpG-oligonucleotide B-CpGpt and incubated in a thermomixer for 3 h at 37° C. in 0.2×PBS pH 7.4. Subsequently, reaction mixtures were subjected to DNaseI digestion (5 U/ml) for 3 h at 37° C. (DNaseI, RNase free Fluka AG, Switzerland). VLP preparations for mouse immunization were extensively dialysed (2× against 200-fold volume) for 24 h against PBS pH 7.4 with a 300 kDa MWCO dialysis membrane (Spectrum Medical industries Inc., Houston, USA) to eliminate RNase A and the excess of CpG-oligonucleotides. The analysis of B-CpGpt packaged into HBx33 VLPs was done on a 1% agarose gel stained with ethidium bromide and Coomassie Blue. Loaded on the gel were 50 μg of the following samples: 1. HBx33 VLP untreated; 2. HBx33 VLP treated with RNase A; 3. HBx33 VLP treated with RNase A and packaged with B-CpGpt; 4. HBx33 VLP treated with RNase A, packaged with B-CpGpt and treated with DNaseI; 5. HBx33 VLP treated with RNase A, packaged with B-CpGpt, treated with DNaseI and dialysed; 6. 1 kb MBI Fermentas DNA ladder. It could be shown that RNAse treatment reduced the nucleic acid content of the capsids and slowed their migration. Addition of B-CpGpt restored nucleic acid content and fast migration of capsids. DNAse I only digested the free oligonucleotides while the packaged oligonucleotides remained in the VLP also after dialysis.

EXAMPLE 9

Immunostimulatory Nucleic Acids can be Packaged into Qβ VLPs Coupled with Antigens.

Coupling of p33 peptides to Qβ VLPs:

Recombinantly produced virus-like particles of the RNA-bacteriophage Qb (Qβ VLPs) were used untreated or after coupling to p33 peptides containing an N-terminal CGG or and C-terminal GGC extension (CGG-KAVYNFATM (SEQ ID NO: 81) and KAVYNFATM-GGC (SEQ ID NO: 82)). Recombinantly produced Qβ VLPs were derivatized with a 10 molar excess of SMPH (Pierce) for 0.5 h at 25° C., followed by dialysis against 20 mM HEPES, 150 mM NaCl, pH 7.2 at 4° C. to remove unreacted SMPH. Peptides were added in a 5 fold molar excess and allowed to react for 2 h in a thermomixer at 25° C. in the presence of 30% acetonitrile. The analysis of the p33 coupling to Qb VLPs was done on SDS-PAGE after Coomassie Blue staining. Loaded were the following samples: (A) 1. NEB Prestained Protein Marker, Broad Range (# 7708S), 10 μl; 2. Qb VLP, 14 μg; 3. Qb VLP derivatized with SMPH, after dialysis; 4. Qb VLP coupled with CGG-p33, supernatant. (B) 1. NEB Prestained Protein Marker, Broad Range (# 7708S), 10 μl; 2. Qb VLP, 10 μg; 3. Qb VLP coupled with GGC-p33, supernatant. The SDS-PAGE analysis demonstrated multiple coupling bands consisting of one, two or three peptides coupled to the Qβ monomer. For the sake of simplicity the coupling product of the peptide p33 and Qβ VLPs was termed, in particular, throughout the example section Qbx33.

Qβ VLPs, when produced in *E. coli* by expressing the bacteriophage Qβ capsid protein, contain RNA which can be digested and so eliminated by incubating the VLPs with RNase A.

Low Ionic Strength and Low Qβ Concentration Allow RNA Hydrolysis of Qβ VLPs by RNAse A:

Qβ VLPs at a concentration of 1.0 mg/ml in 20 mM Hepes/150 mM NaCl buffer (HBS) pH 7.4 were either digested directly by addition of RNase A (300 μg/ml, Qiagen AG, Switzerland) or were diluted with 4 volumes H2O to a final 0.2×HBS concentration and then incubated with RNase A (60 μg/ml, Qiagen AG, Switzerland). Incubation was allowed for 3 h at 37° C. in a thermomixer at 650 rpm. RNA hydrolysis from Qb VLPs by RNase A under low and high ionic strength was analyzed on a 1% agarose gel stained with ethidium bromide and Coomassie Blue. Loaded on the gel were the following samples: (A, B) 1. MBI Fermentas 1 kb DNA ladder; 2. Qb VLP untreated; 3. Qb VLP treated with RNase A in 1×HBS buffer pH7.2. (C, D) 1. MBI Fermentas 1 kb DNA ladder; 2. Qb VLP untreated; 3. Qb VLP treated with RNase A in 0.2× HBS buffer pH7.2. It was demonstrated that in 1× HBS only a very weak reduction of RNA content was observed, while in 0.2× HBS most of the RNA were hydrolysed. In agreement, capsid migration was unchanged after addition of RNAse A in 1× HBS, while migration was slower after addition of RNAse in 0.2× HBS.

Low Ionic Strength Increases Nucleic Acid Packaging in Qβ VLPs:

After RNase A digestion in 0.2× HBS the Qβ VLPs were concentrated to 1 mg/ml using Millipore Microcon or Centriplus concentrators and aliquots were dialysed against 1× HBS or 0.2× HBS. Qβ VLPs were supplemented with 130 nmol/ml CpG-oligonucleotide B-CpG and incubated in a thermomixer for 3 h at 37° C. Subsequently Qβ VLPs were subjected to Benzonase digestion (100 U/ml) for 3 h at 37° C. Samples were analysed on 1% agarose gels after staining with ethidium bromide or Coomassie Blue. Loaded on the gel were the following samples: 1. Qb VLP untreated; 2. Qb VLP treated with RNase A; 3. Qb VLP treated with RNase A and packaged with B-CpG in 0.2× HBS buffer pH7.2 and treated with Benzonase; 4. HBx33 VLP (see example 12) treated with RNase A, packaged with B-CpG in 1× HBS buffer pH7.2 and treated with Benzonase. In 1× HBS only a very low amount of oligonucleotides could be packaged, while in 0.2×

HBS a strong ethidium bromide stained band was detectable, which colocalized with the Coomassie blue stain of the capsids.

Different Immunostimulatory Nucleic Acids can be Packaged in Qβ and Qbx33 VLPs:

After RNase A digestion in 0.2× HBS the Qβ VLPs or Qbx33 VLPs were concentrated to 1 mg/ml using Millipore Microcon or Centriplus concentrators and supplemented with 130 nmol/ml CpG-oligonucleotides B-CpGpt, g10gacga and the 253 mer dsCyCpG-253 (Table 2) and incubated in a thermomixer for 3 h at 37° C. Subsequently Qβ VLPs or Qbx33 VLPs were subjected to DNAse I digestion (5 U/ml) or Benzonase digestion (100 U/ml) for 3 h at 37° C. Samples were analysed on 1% agarose gels after staining with ethidium bromide or Coomassie Blue.

Loaded on the gel were 50 μg of the following samples: 1. Qbx33 VLP untreated; 2. Qbx33 VLP treated with RNase A; 3. Qbx33 VLP treated with RNase A and packaged with B-CpGpt; 4. Qbx33 VLP treated with RNase A, packaged with B-CpGpt, treated with DNaseI and dialysed; 5. 1 kb MBI Fermentas DNA ladder. (C) depicts the analysis of the amount of packaged oligo extracted from the VLP on a 15% TBE/urea stained with SYBR Gold. Loaded on gel are the following samples: 1. BCpGpt oligo content of 2 μg Qbx33 VLP after proteinase K digestion and RNase A treatment; 2. 20 pmol B-CpGpt control; 3. 10 pmol B-CpGpt control; 4. 5 pmol B-CpGpt control.

Loaded on another gel were 15 μg of the following samples: 1. MBI Fermentas 1 kb DNA ladder; 2. Qbx33 VLP untreated; 3. Qbx33 VLP treated with RNase A; 4. Qbx33 VLP treated with RNase A and packaged with g10gacga-PO; 5. Qbx33 VLP treated with RNase A, packaged with g10gacga-PO, treated with Benzonase and dialysed.

Loaded on a third gel were 15 μg of the following samples: 1. MBI Fermentas 1 kb DNA ladder; 2. Qbx33 VLP untreated; 3. Qbx33 VLP treated with RNase A; 4. Qbx33 VLP treated with RNase A, packaged with dsCyCpG-253 and treated with DNaseI; 5. Qbx33 VLP treated with RNase A, packaged with dsCyCpG-253, treated with DNaseI and dialysed.

The different nucleic acids B-CpGpt, g10gacga and the 253mer dsDNA could be packaged into Qbx33. Packaged nucleic acids were resistant to DNAse I digestion and remained packaged during dialysis. Packaging of B-CpGpt was confirmed by release of the nucleic acid by proteinase K digestion followed by agarose electrophoresis and ethidium bromide staining.

EXAMPLE 10

AP205 Disassembly-Purification-Reassembly and Packaging of Immunostimulatory Nucleic Acids.

A. Disassembly and Reassembly of AP205 VLP from Material able to Reassemble without Addition of Oligonucleotide Disassembly: 40 mg of lyophilized purified AP205 VLP (SEQ-ID: 80 or 81) were resolubilized in 4 ml 6 M GuHCl, and incubated overnight at 4° C. The disassembly mixture was centrifuged at 8000 rpm (Eppendorf 5810 R, in fixed angle rotor F34-6-38, used in all the following steps). The pellet was resolubilized in 7 M urea, while the supernatant was dialyzed 3 days against NET buffer (20 mM Tris-HCI, pH 7.8 with 5 mM EDTA and 150 mM NaCl) with 3 changes of buffer. Alternatively, dialysis was conducted in continuous mode over 4 days. The dialyzed solution was centrifuged at 8000 rpm for 20 minutes, and the pellet was resolubilized in 7 M urea, while the supernatant was pelletted with ammonium sulphate (60% saturation), and resolubilized in a 7 M urea buffer containing 10 mM DTT. The previous pellets all resolubilized in 7 M urea were joined, and precipitated with ammonium sulphate (60% saturation), and resolubilized in a 7 M urea buffer containing 10 mM DTT. The materials resolubilized in the 7 M urea buffer containing 10 mM DTT were joined and loaded on a Sephadex G75 column equilibrated and eluted with the 7 M urea buffer containing 10 mM DTT at 2 ml/h. One peak eluted from the column. Fractions of 3 ml were collected. The peak fractions containing AP205 coat protein were pooled and precipitated with ammonium sulphate (60% saturation). The pellet was isolated by centrifugation at 8000 rpm, for 20 minutes. It was resolubilized in 7 M urea, 10 mM DTT, and loaded on a short Sepharose 4B column (1.5×27 cm Sepharose 4B, 2 ml/h, 7 M urea, 10 mM DTT as elution buffer). Mainly one peak, with a small shoulder eluted from the column. The fractions containing the AP205 coat protein were identified by SDS-PAGE, and pooled, excluding the shoulder. This yielded a sample of 10.3 ml. The protein concentration was estimated spectrophotometrically by measuring an aliquot of protein diluted 25-fold for the measurement, using the following formula: (1.55×OD280-0.76×OD260)×volume. The average concentration was of 1 nmol/ml of VLP (2.6 mg/ml). The ratio of absorbance at 280 nm vs. 260 nm was of 0.12/0.105.

Reassembly: 1.1 ml beta-mercaptoethanol was added to the sample, and the following reassembly reactions were set up:

1 ml of AP205 coat protein, no nucleic acids 1 ml of AP205 coat protein, rRNA (approx. 200 OD260 units, 10 nmol)

9 ml of AP205 coat protein, CyCpG (370 ul of 225 pmol/μl solution, i.e. 83 μnmol).

These mixtures were dialyzed 1 hour against 30 ml of NET buffer containing 10% beta-mercaptoethanol. The mixture containing no nucleic acids was dialyzed separately. The dialysis was then pursued in a continuous mode, and 1 l of NET buffer was exchanged over 3 days. The reaction mixtures were subsequently extensively dialyzed against water (5 changes of buffer), and lyophilized. They were resolubilized in water, and analyzed by electron microscope (EM). All mixtures contained capsids, showing that AP205 VLP reassembly is independent of the presence of detectable nucleic acids, as measured by agarose gel electrophoresis using ethidium bromide staining. The EM procedure was as follows: A suspension of the proteins was absorbed on carbon-formvar coated grids and stained with 2% phosphotungstic acid (pH 6,8). The grids were examined with a JEM 100C (JEOL,Japan) electron microscope at an accelerating voltage of 80 kV. Photographic records (negatives) were performed on Kodak electron image film and electron micrographs were obtained by printing of negatives on Kodak Polymax paper. The VLP reassembled in the presence of the CyCpG was purified over a Sepharose 4B column (1×50 cm), eluted with NET buffer (1 ml/h). The fractions were analyzed by Ouchterlony assay, and the fractions containing VLP were pooled. This resulted in a sample of 8 ml, which was desalted against water by dialysis, and dried. The yield of capsid was of 10 mg. Analysis of resolubilized material in a 0.6% agarose gel stained with ethidium-bromide showed that the capsids were empty of nucleic acids. Samples of the reassembly reaction containing CyCpG taken after the reassembly step and before extensive dialysis were analysed on a 0.6% agarose gel stained with ethidium-bromide and Coomassie blue. A band migrating at the same height than intact AP205 VLP and staining both for ethidium-bromide and Coomassie blue staining could be obtained, showing that AP205 VLP containing oligodeoxynucleotide had been reassembled. The extensive dialysis steps following the reassembly procedure are likely to have led to diffusion of the oligodeoxynucleotide outside of the VLPs. Significantly, the AP205 VLPs could also be reassembled in the absence of detectable oligodeoxynucleotide, as measured by agarose gel electrophoresis using ethidium bromide staining. Oligodeoxynucleotides could thus be successfully bound to AP205 VLP after initial disassembly of the VLP, purification of the disassembled coat protein from nucleic acids and subsequent reassembly of the VLP in the presence of oligodeoxynucleotide.

B. Reassembly of AP205 VLP using Disassembled Material which does not Reassemble in the Absence of Added Oligonucleotide Disassembly: 100 mg of purified and dried recombinant AP205 VLP were used for disassembly as described above. All steps were performed essentially as described under disassembly in part A, but for the use of 8 M urea to solublize the pellets of the ammonium sulphate precipitation steps and the omission of the gel filtration step using a CL-4B column prior to reassembly . The pooled fractions of the Sephadex G-75 column contained 21 mg of protein as determined by spectroscopy using the formula described in part A. The ratio of absorbance at 280 nm to the absorbance at 260 nm of the sample was of 0.16 to 0.125. The sample was diluted 50 times for the measurement.

Reassembly: The protein preparation resulting from the Sephadex G-75 gel filtration purification step was precipitated with ammonium sulphate at 60% saturation, and the resulting pellet solubilized in 2 ml 7 M urea, 10 mM DTT. The sample was diluted with 8 ml of 10% 2-mercaptoethanol in NET buffer, and dialyzed for 1 hour against 40 ml of 10% 2-mercaptoethanol in NET buffer. Reassembly was initiated by adding 0.4 ml of a CyCpG solution (109 nmol/ml) to the protein sample in the dialysis bag. Dialysis in continous mode was set up, and NET buffer used as eluting buffer. Dialysis was pursued for two days and a sample was taken for EM analysis after completion of this dialysis step. The dialyzed reassembly solution was subsequently dialyzed against 50% v/v Glycerol in NET buffer, to achieve concentration. One change of buffer was effected after one day of dialysis. The dialysis was pursued over a total of three days.

The dialyzed and concentrated reassembly solution was purified by gel filtration over a Sepharose 4-B column (1×60 cm) at a flow rate of 1 ml/hour, in NET buffer. Fractions were tested in an Ouchterlony assay, and fractions containing capsids were dried, resuspended in water, and rechromatographed on the 4-B column equilibrated in 20 mM Hepes pH 7.6. Using each of the following three formula:

$$(183*OD230\ \text{nm}-75.8*OD260\ \text{nm})*\text{volume (ml)} \quad 2.$$

$$((OD235\ \text{nm}-OD280\ \text{nm})/2.51)\times\text{volume} \quad 3.$$

$$((OD228.5\ \text{nm}-OD234.5\ \text{nm})*0.37)\times\text{volume} \quad 1.$$

protein amounts of 6-26 mg of reassembled VLP were determined.

The reassembled AP205 VLPs were analyzed by EM as described above, agarose gel electrophoresis and SDS-PAGE under non-reducing conditions.

The EM analysis of disassembled material shows that the treatment of AP205 VLP with guanidinium-chloride essentially disrupts the capsid assembly of the VLP. Reassembly of this disassembled material with an oligonucleotide yielded capsids, which were purified and further enriched by gel filtration. Two sizes of particles were obtained; particles of about 25 nm diameter and smaller particles are visible in the electron micrograph. No reassembly was obtained in the absence of oligonucleotides. Loading of the reassembled particles on agarose electrophoresis showed that the reassembled particles contained nucleic acids. Extraction of the nucleic acid content by phenol extraction and subsequent loading on an agarose gel stained with ethidium bromide revealed that the particles contained the oligonucleotide used for reassembly. Identity of the packaged oligonucleotide was controlled by loading a sample of this oligonucleotide side to side to the nucleic acid material extracted from the particles. The agarose gel where the reassembled AP205 VLP had been loaded and previously stained with ethidium bromide was subsequently stained with Coomassie blue, revealing comigration of the oligonucleotide content with the protein content of the particles, showing that the oligonucleotide had been packaged in the particles. Loaded on the gel were untreated AP205 VLP, 3 samples with differing amount of AP205 VLP reassembled with CyCpG and purified, and untreated Qβ VLP.

Loading of the reassembled AP205 VLP on an SDS-PAGE gel, run in the absence of reducing agent demonstrated that the reassembled particles have formed disulfide bridges, as is the case for the untreated AP205 VLP. Moreover, the disulfide bridge pattern is identical to the untreated particles. The samples loaded on the SDS gel were: Protein Marker, untreated wt Qβ, reassembled wt Qβ, untreated AP205 VLP, reassembled AP205 VLP. The Molecular Weight of the AP205 VLP subunit is 14.0 kDa, while the molecular weight of the Qβ subunit is 14.3 kDa (both molecular weights calculated with the N-terminal methionine).

C. Coupling of p33 epitope (sequence: H2N-KAVYNFATMGGCCOOH, with free N- and C-termini, (SEQ ID NO: 82) to AP205 VLPs reassembled with CYCpG Reassembled AP205 VLP obtained as described in part B, and in 20 mM Hepes, 150 mM NaCl, pH 7.4 was reacted at a concentration of 1.4 mg/ml with a 5-fold excess of the crosslinker SMPH diluted from a 50 mM stock in DMSO for 30 minutes at 15° C. The obtained so-called derivatized AP205 VLP was dialyzed 2×2 hours against at least a 1000-fold volume of 20 mM Hepes, 150 mM NaCl, pH 7.4 buffer. The derivatized AP205 was reacted at a concentration of 1 mg/ml with either a 2.5-fold, or with a 5-fold excess of peptide, diluted from a 20 mM stock in DMSO, for 2 hours at 15° C. The sample was subsequently flash frozen in liquid nitrogen for storage.

The coupling reaction was analyzed on an SDS-PAGE. Loaded on a gel were the following samples: protein marker; derivatized AP205 VLP (d); AP205 VLP coupled with a 2.5-fold excess of peptide, supernatant (s); AP205 VLP coupled with a 2.5-fold excess of peptide, pellet (p); AP205 VLP coupled with a 5-fold excess of peptide, supernatant (s); AP205 VLP coupled with a 5-fold excess of peptide, pellet (p). The result of the coupling reaction revealed that a higher degree of coupling could be achieved by using a 5-fold excess of peptide rather than with a 2.5 fold excess of peptide in the coupling reaction.

EXAMPLE 11

Non-enzymatic hydrolysis of the RNA content of VLPs and packaging of immunostimulatory nucleic acids.

ZnSO4 dependent degradation of the nucleic acid content of a VLP:

5 mg Qβ VLP (as determined by Bradford analysis) in 20 mM HEPES, pH 7.4, 150 mM NaCl was dialysed either against 2000 ml of 50 mM TrisHCl pH 8.0, 50 mM NaCl, 5% glycerol, 10 mM MgCl2 or 2000 ml of 4 mM HEPES, pH 7.4, 30 mM NaCl for 2 h at 4° C in SnakeSkin™ pleated dialysis tubing (Pierce, Cat. No. 68035). Each of the dialysis buffers was exchanged once and dialysis was allowed to continue for another 16 h at 4° C. The dialysed solution was clarified for 10 minutes at 14 000 rpm (Eppendorf 5417 R, in fixed angle rotor F45-30-11, used in all the following steps) and Protein concentration was again determined by Bradford analysis. Qβ VLPs in 50 mM TrisHCl pH 8.0, 50 mM NaCl, 5% glycerol, 10 mM MgCl2 were diluted with the corresponding buffer to a final protein concentration of 1 mg/ml whereas Qβ VLPs in 4 mM HEPES pH 7.4, 30 mM NaCl were diluted with the corresponding buffer to a final protein concentration of 0.5 mg/ml. This capsid-containing solutions were centrifuged again for 10 minutes at 14 000 rpm at 4° C. The supernatants were than incubated with ZnSO4 which was added to a final concentration of 2.5 mM for 24 h at 60° C. in an Eppendorf Thermomixer comfort at 550 rpm. After 24 h the solutions were clarified for 10 minutes at 14000 rpm and the sediment was discarded. The efficiency of the ZnSO4-dependent degradation of nucleic acids was confirmed by agarose gelelectrophoresis. The supernatants were dialysed against 5000 ml of 4 mM HEPES pH 7.4, 30 mM NaCl for 2 h at 4° C. 5000 ml buffer was exchanged once and dialysis continued over night at 4° C. The dialysed solution was clarified for 10 minutes at 14 000 rpm and 4° C., a negligible sediment was discarded and the protein concentration of the supernatants were determined by Bradford analysis. Similar results were obtained with copper chloride/phenanthroline/hydrogen peroxide treatment of capsids. Those skilled in the art know alternative non-enzymatic procedures for hydrolysis or RNA.

ZnSO4-treated Qβ VLPs was analyzed by agarose gelelectrophoresis: Qβ VLPs which had been purified from *E. coli* and dialysed either against buffer 1 (50 mM TrisHCl pH 8.0, 50 mM NaCl, 5% glycerol, 10 mM MgCl2) or buffer 2 (4 mM HEPES, pH 7.4, 30 mM NaCl) were incubated either without or in the presence of 2.5 mM zinc sulfate (ZnSO4) for 24 hrs at 60° C. After this treatment equal amounts of the indicated samples (5 μg protein) were mixed with loading dye and loaded onto a 0.8% agarose gel. After the run the gel was stained with ethidium bromide. Treatment of VLPs with ZnSO4 caused degradation of the nucleic acid content, while the mock-treated controls were unaffected.

Packaging of Oligodeoxynucleotides into ZnSO4-Treated VLPs:

ZnSO4-treated and dialysed Qβ capsids with a protein concentration (as determined by Bradford analysis) beween 0.4 mg/ml and 0.9 mg/ml (which corresponds to a concentration of capsids of 159 nM and 357.5 nM, respectively) were used for the packaging of the oligodeoxynucleotides. The oligodeoxynucleotides were added at a 300-fold molar excess to the of Qβ-VLP capsids and incubated for 3 h at 37° C. in an Eppendorf Thermomixer comfort at 550 rpm . After 3 h the reactions were centrifuged for 10 minutes at 14 000 rpm and 4° C. The supernatants were dialysed in Spectra/Por®CE DispoDialyzer with a MWCO 300,000 (Spectrum, Cat. No. 135 526) against 5000 ml of 20 mM HEPES pH 7.4, 150 mM NaCl for 8 h at 4° C. 5000 ml buffer was exchanged once and dialysis continued over night at 4° C. The protein concentration of the dialysed samples were determined by Bradford analysis. Qβ capsids and their nucleic acid contents were analyzed as described in Examples 7 and 9.

Packaging of oligodeoxynucleotides into ZnSO4-treated VLPs was analyzed by agarose gelelectrophoresis. Qβ VLPs which had been treated with 2.5 mM zinc sulfate (+ZnSO4) were dialysed against 4 mM HEPES, pH 7.4, 30 mM NaCl and incubated for 3 hrs at 37° C. with an excess of oligodeoxynucleotides (due to the dialysis the concentration of ZnSO4 was decreased by an order of 106, therefore its indicated only in parenthesis) After this incubation in presence of oligodeoxynucleotides, equal amounts of the indicated samples (5 μg protein) were mixed with loading dye and loaded onto a 0.8% agarose gel. After the run the gel was stained with ethidium bromide. Adding of oligodeoxynucleotides to ZnSO4-treated Qβ VLPs could restore the electrophoretical behaviour of the so treated capsids when compared to untreated Qβ capsids which had been purified from *E. coli.*

The nucleic acid content of ZnSO4- and oligodeoxynucleotide treated Qβ VLPs was analyzed by Benzonase and proteinase K digestion and polyacrylamide TBE/Urea gelelectrophoresis: Oligodeoxynucleotides were packaged into ZnSO4-treated Qβ VLPs as described above. 25 μg of these VLPs were digested with 25 μl Benzonase (Merck, Cat. No. 1.01694.0001) according to the manufactures instructions. After heat-inactivation of the nuclease (30 minutes at 80° C.) the VLPs were treated with Proteinase K (final enzyme concentration was 0.5 mg/ml) according to the manufactures instructions. After 3 hrs the equivalent of 2 ug Qβ VLPs which had been digested by Benzonase and proteinase K were mixed with TBE-Urea sample buffer and loaded on a 15% polyacrylamide TBE-Urea gel (Novex®, Invitrogen Cat. No. EC6885). The capsids loaded in lane 2 were treated with 2.5 mM ZnSO4 in presence of buffer 1 (see above), while the capsids loaded in lane 3 were treated with 2.5 mM ZnSO4 in presence of buffer 2 (see above). As qualitative as well as quantitative standard, 1 pmol, 5 pmol and 10 pmol of the oligodeoxynucleotide which was used for the reassembly reaction, was loaded onto the same gel (lanes 4 -6). As control, Qβ capsids which had been purified from *E. coli* were treated exactly the same and analyzed on the same polyacrylamide TBE-Urea gel (lane 1). After the run was completed, the gel was fixed, equilibrated to neutral pH and stained with SYBR-Gold (Molecular Probes Cat. No. S-11494). Intact Qβ VLPs (which had been purified from *E. coli*) did not contain nucleic acids of similar size than those which had been extracted from ZnSO4-and oligodeoxynucleotide treated Qβ capsids. In addition, nucleic acids isolated from the latter VLPs were comigrating with the oligodeoxynucleotides which had been used in the reassembly reaction. This results confirmed that the used oligodeoxynucleotides were packaged into ZnSO4-treated Qβ capsids.

EXAMPLE 12

Coupling of Antigenic Peptides after Packaging of Immunostimulatory Nucleic Acids into VLPs.

RNaseA and ZnSO4 mediated degradation of the nucleic acid content of a VLP.

Qβ VLPs were treated with RNaseA as described in Example 9 under low ionic strength conditions (20 mM Hepes pH 7.4 or 4 mM Hepes, 30 mM NaCl, pH 7.4 ). Similarly, other VLPs such as described in Examples 2, 3, 7, and 10, i.e. GA, BKV, HBcAg, and AP205 are treated. Alternatively, Qβ VLPs and AP205 VLPs were treated with ZnSO4 under low ionic strength conditions (20 mM Hepes pH 7.4 or 4 mM Hepes, 30 mM NaCl pH 7.4) as described in Example 11. AP205 VLP (1 mg/ml) in either 20 mM Hepes pH 7.4 or 20 mM Hepes, 1 mM Tris, pH 7.4 was treated for 48 h with 2.5 mM ZnSO4 at 50° C. in an Eppendorf Thermomixer comfort at 550 rpm. Qβ and AP205 VLP samples were clarified as described in Example 11 and supernatants were dialysed in 10.000 MWCO Spectra/Por® dialysis tubing (Spectrum, Cat. nr. 128 118) against first 2 l 20 mM Hepes, pH 7.4 for 2 h at 4° C. and, after buffer exchange, overnight. Samples were clarified after dialysis as described in Example 11 and protein concentration in the supernatants was determined by Bradford analysis.

Packaging of ISS into RnaseA and ZnSO4 Treated VLPs.

After RNA hydrolysis and dialysis, Qβ and AP205 VLPs (1-1.5 mg/ml) were mixed with 130 μl of CpG oligonucleotides (NKCpG, G10-PO—cf. Table 2; G3-6, G8-8—cf. Table 3; 1 mM oligonucleotide stock in 10 mM Tris pH 8) per ml of VLPs. Samples were incubated for 3 h at 37° C. in a thermoshaker at 650 rpm. Subsequently, samples were treated with 125 U Benzonase/ml VLPs (Merck KGaA, Darmstadt, Germany) in the presence of 2 mM MgCl2 and incubated for 3 h at 37° C. before dialysis. Samples were dialysed in 300.000 MWCO Spectra/Por® dialysis tubing (Spectrum, Cat. nr. 131 447) against 20 mM Hepes, pH 7.4 for 2 h at 4° C., and after buffer exchange overnight against the same buffer. After dialysis samples were clarified as described in Example 11 and protein concentration in the supernatants were determined by Bradford analysis.

Coupling of Immunogenic Peptides to ISS Packaged VLPs.

Qβ VLPs, packaged with ISS were coupled to p33 peptides containing a C-terminal GGC extension (KAVYNFATM-GGC) (SEQ ID NO: 82), resulting in Qb VLPs termed Qb-ISS-33 VLPs. Packaged Qβ VLPs in 20 mM Hepes, pH 7.4 were derivatized with a 10-fold molar excess of SMPH (Pierce) for 0.5 h at 25° C., followed by two dialysis steps of 2 hours each against 20 mM HEPES pH 7.4 at 4° C. to remove unreacted SMPH. Peptides were added in a 5-fold molar excess to the dialysed derivatization mixture, and allowed to react for 2 h in a thermomixer at 25° C. Samples were dialysed in 300.000 MWCO Spectra/Por® dialysis tubing against 20 mM Hepes pH 7.4 for 2 h at 4° C., and after buffer exchange overnight against the same buffer. After dialysis samples were clarified as described in Example 11 and protein concentration in the supernatants were determined by Bradford analysis. Coupling of peptide p33 to Qβ was analysed by SDS-PAGE on 16% PAGE Tris-Glycine gels (Novex® by Invitrogen, Cat. No. EC64952), using a sample buffer containing 2% SDS and β-mercapto ethanol or DTT. Packaging was analysed on 1% agarose gels and, after proteinase K digestion, on TBE/urea gels as described in Example 7.

AP205 VLPs (1.24 mg/ml) packaged with G8-8 oligonucleotide as described above are derivatized and coupled to MelanA 16-35 A/L containing a N-terminal C extension (c GHGHSYTTAE ELAGIGILTV) (SEQ ID NO: 55), resulting in AP205-G8-8-MelanA VLPs. AP205 VLPs (packaged with G8-8), in 20 mM Hepes pH 7.4, are derivatized with a 20-fold molar excess of SMPH for 0.5 h at 25° C., and subsequently dialysed two times against 20 mM HEPES, pH 7.4 at 4° C. to remove unreacted SMPH. Peptide is added to the dialyzed derivatization mixture in a 10-fold molar excess and allowed to react for 2 h in a thermomixer at 25° C. Samples were dialysed in 10.000 MWCO dialysis tubing against 20 mM Hepes pH 7.4 for 2 h at 4° C., and after buffer exchange, overnight against the same buffer. After dialysis, samples are clarified as described in Example 11 and protein concentration in the supernatants are determined by Bradford analysis. Coupling efficiency of peptide MelanA 16-35 A/L to AP205 is analysed by SDS-PAGE on 16% PAGE Tris-Glycine gels. G8-8 oligonucleotide packaging in AP205 is analysed on 1% agarose gels and, after proteinase K digestion, G8-8 oligonucleotide amount in AP205-G8-8- MelanA 16-35 A/L is analysed on TBE/urea gels as described in Example 7.

Packaging of RNAseA and ZnSO4-treated Qβ VLPs with NKCpG before as well as after coupling to p33 peptide was analyzed by agarose gelelectrophoresis. Qβ VLPs containing NKCpG oligonucleotides and subsequently coupled to p33 peptide were termed Qb-NKCpG-33 VLPs. On a 1% agarose gel, the fluorescent band visible on the ethidium bromide stained gel co-migrates with the protein band visible on the Coomassie Blue stained gel demonstrating packaging. Thus, upon packaging, both RNaseA and ZnSO4 treated Qβ VLPs contain NKCpG oligonucleotides before as well as after coupling to p33 peptide. Coupling efficiency of the p33 peptide is maintained as can be judged from the multiple coupling products visible after SDS-PAGE analysis on a 16% PAGE Tris-Glycine gel, as bands migrating slower than residual Qβ VLP subunit monomers which have not reacted with peptide. The packaging efficiency can be estimated from the analysis of the TBE/urea gel by comparison of the signal of the oligonucleotide from the packaged Qb-NKCpG-33 lane with the signal of the oligonucleotide standard loaded on the same gel. Packaged amounts of NKCPG were between 1 and 4 nmol/100 μg Qb-NKCpG-33 VLPs.

Packaging of G8-8 oligonucleotides into Qβ VLPs and subsequent coupling to p33 peptide was analyzed by agarose gelelectrophoresis. Qβ VLPs containing G8-8 oligonucleotides and subsequently coupled to p33 peptide were termed Qb-G8-8-33 VLPs. Ethidium bromide staining of G8-8 packaged Qβ VLPs can be seen on a 1% agarose gel stained with ethidium bromide. Comigration of the ethidium bromide fluorescent band with the Qβ VLP protein band visible on the same gel subsequently stained with Coomassie Blue demonstrates packaging. Coupling efficiency can be estimated to be 30% by SDS-PAGE analysis on a 16% PAGE Tris-Glycine gel. Analysis of the G8-8 content of Qb-G8-8-33 VLPs was done on a 1% agarose gel, where the amount of oligonucleotide packaged was of approximately 1 nmol/100 μg Qb-G8-8-33 VLPs.

Packaging of G8-8 oligonucleotides into AP205 VLPs was analyzed by agarose gelelectrophoresis. Staining of G8-8 packaged AP205 VLPs can be seen on a 1% agarose gel stained with ethidium bromide. Comigration of the AP205 VLPs protein band detected on the same gel subsequently stained with Coomassie Blue demonstrated packaging. Coupling efficiency with the MelanA 16-35 A/L peptide can be estimated from the SDS-PAGE analysis on a 16% PAGE Tris-Glycine gel where multiple coupling bands migrating slower than the residual AP205 VLP monomer subunits, which did not react with peptide, cam be visible. Coupling efficiency is compared to the coupling efficiency obtained for the Qb-G8-8-33 VLPs. Analysis of the G8-8 oligonucleotide content of AP205 VLPs after coupling to MelanA 16-35 A/L can be seen on TBE/urea gel electrophoresis.

EXAMPLE 13

Packaging of Immunostimulatory Guanosine Flanked Oligonucleotides into VLPs.

Qbx33 VLPs (Qβ VLPs coupled to peptide p33, see Example 9) were treated with RNaseA under low ionic conditions (20 mM Hepes pH 7.4) as described in Example 9 to hydrolyse RNA content of the Qbx33 VLP. After dialysis against 20 mM Hepes pH 7.4, Qbx33 VLPs were mixed with guanosine flanked oligonucleotides (Table 2: G10-PO, Table 3: G3-6, G7-7, G8-8, G9-9 or G6, from a 1 mM oligonucleotide stock in 10 mM Tris pH 8) and incubated as described in Example 12. Subsequently, Qbx33 VLPs were treated with Benzonase and dialysed in 300.000 MWCO tubing. Samples with oligos G7-7, G8-8 and G9-9 were extensively dialysed over 3 days with 4 buffer exchanges to remove free oligo. Packaging was analysed on 1% agarose gels and, after proteinase K digestion, on TBE/urea gels as described in Example 7.

TABLE 3

Sequences of immunostimulatory nucleic acids used in the Examples.

| ISS name | 5'-3' sequence | SEQ ID NO |
|---|---|---|
| | GACGATCGTC | 1 |
| G3-6 | GGGGACGATCGTCGGGGGG | 2 |
| G4-6 | GGGGGACGATCGTCGGGGGG | 3 |

TABLE 3-continued

| Sequences of immunostimulatory nucleic acids used in the Examples. | | |
|---|---|---|
| ISS name | 5'-3' sequence | SEQ ID NO |
| G5-6 | GGGGGGACGATCGTCGGGGGG | 4 |
| G6-6 | GGGGGGGACGATCGTCGGGGGG | 5 |
| G7-7 | GGGGGGGGACGATCGTCGGGGGGG | 6 |
| G8-8 | GGGGGGGGGACGATCGTCGGGGGGGG | 7 |
| G9-9 | GGGGGGGGGGACGATCGTCGGGGGGGGG | 8 |
| G6 | GGGGGGCGACGACGATCGTCGTCGGGGGGG | 9 |
| G10-PO | GGGGGGGGGGGACGATCGTCGGGGGGGGGG | 41 |

Packaging of G3-6, G6, G8-8 oligonucleotides in RNaseA treated Qbx33 VLPs was analyzed by agarose gelelectrophoresis. Upon oligonucleotide packaging, a fluorescent band migrating slightly slower than reference untreated Qβ VLP becomes visible on the 1% agarose gel stained with ethidium bromide indicating the presence of oligonucleotides. The signal is maintained after treatment with Benzonase, indicating packaging of the oligonucleotides within the Qbx33 VLPs. The packaging efficiency can be estimated from the TBE/urea gel electrophoresis. The amount of the G3-6 oligonucleotide (approximately 4 nmol/100 μg Qbx33 VLPs) packaged is much higher than the amount of packaged G8-8 oligonucleotide (approximately 1 nmol/100 μg Qbx33 VLPs). This indicates a dependence of packaging ability on the length of the guanosine nucleotides tail flanking the CpG motif.

EXAMPLE 14

Packaging Ribonucleic Acid into VLPs.

ZnSO4 dependent degradation of the nucleic acid content of a VLP.

Qβ VLPs were treated with ZnSO4 under low ionic strength conditions (20 mM Hepes pH 7.4 or 4 mM Hepes, 30 mM NaCl, pH 7.4) as described in Example 11. AP205 VLPs (1 mg/ml) in either 20 mM Hepes pH 7.4 or 20 mM Hepes, 1 mM Tris, pH 7.4 were treated for 48 h with 2.5 mM ZnSO4 at 50° C. in an Eppendorf Thermomixer comfort at 550 rpm. Qβ and AP205 VLP samples were clarified as in Example 11 and dialysed against 20 mM Hepes, pH 7.4 as in Example 12.

Packaging of Poly (I:C) into ZnSO4-Treated VLPs:

The immunostimulatory ribonucleic acid poly (I:C), (Cat. nr. 27-4732-01, poly(I).poly(C), Pharmacia Biotech) was dissolved in PBS (Invitrogen cat. nr. 14040) or water to a concentration of 4 mg/ml (9 μM). Poly (I:C) was incubated for 10 minutes at 60° C. and then cooled to 37° C. Incubated poly (I:C) was added in a 10-fold molar excess to either ZnSO4-treated Qβ p or AP205 VLPs (1-1.5 mg/ml) and the mixtures were incubated for 3 h at 37° C. in a thermomixer at 650 rpm. Subsequently, excess of free poly (I:C) was enzymatically hydrolysed by incubation with 125 U Benzonase per ml VLP mixture in the presence of 2 mM MgCl2 for 3 h at 37° C. in a thermomixer at 300 rpm. Upon Benzonase hydrolysis samples were clarified as described in Example 11 and supernatants were dialysed in 300.000 MWCO Spectra/Por® dialysis tubing (Spectrum, Cat. nr. 131 447) against 2 120 mM Hepes, pH 7.4 for 2 h at 4° C., and after buffer exchange overnight against the same buffer.. After dialysis, samples were clarified as described in Example 11 and protein concentration in the supernatants were determined by Bradford analysis.

Coupling of Immunogenic Peptides to Poly (I:C) Packaged VLPs.

Qβ VLPs (1 mg/ml) packaged with poly (I:C) were derivatized and coupled either to p33 peptide (KAVYNFATM-GGC) (SEQ ID NO: 82) as described in Example 12, or to MelanA peptide (MelanA 16-35A/L CGHGHSYTTAEELA-GIGILTV) (SEQ ID NO: 55), resulting in Qb-pIC-33 and Qb-pIC-MelanA VLPs, respectively. For coupling to MelanA peptide, the packaged Qβ VLP was derivatized with a 2.1 -fold molar excess of SMPH (Pierce) for 0.5 h at 25° C., followed by two dialysis steps against 20 mM HEPES, pH 7.4 at 4° C. to remove unreacted SMPH. Peptides were added in a 2.1 -fold molar excess and allowed to react for 1.5 h in a thermomixer at 25° C. Samples were dialysed in 300.000 MWCO Spectra/Por® CE Dispo Dialyzer against 20 mM Hepes, pH 7.2 for 3 h at 4° C., and after buffer exchange, overnight against the same buffer. After dialysis samples were clarified as described in Example 11 and protein concentration in the supernatants were determined by Bradford analysis. Coupling of peptide p33 and peptide MelanA to Qβ was analysed by SDS-PAGE on 16% PAGE Tris-Glycine gels. Packaging was analysed on 1% agarose gels and, after proteinase K digestion, on TBE/urea gels as described in Example 7.

Packaging of poly (I:C) into ZnSO4 treated Qβ VLPs and coupling with MelanA peptide resulting in Qb-pIC-MelanA VLPs was analyzed by agarose gelelectrophoresis. The fluorescent signal visible on an ethidium bromide stained 1% agarose gel, indicating presence of nucleic acid, co-migrates with the protein band that became visible upon Coomassie Blue staining of the gel, demonstrating packaging. Coupling efficiency of the MelanA peptide was estimated by SDS-PAGE analysis on a 16% PAGE Tris-Glycine gel. Multiple coupling products were visible as bands migrating slower than the Qβ VLP monomer subunits, which had not reacted with peptide. Coupling efficiency of MelanA was overall comparable to the coupling efficiency obtained for the Qb-G8-8-33 VLPs (Example 12), albeit slightly lower. The packaging efficiency into Qb-pIC-MelanA could be estimated from the TBE/urea gel; the packaged amount of poly (I:C) in Qβ was approximately 25 pmol and remained the same upon MelanA coupling.

AP205 VLPs (1 mg/ml) packaged with poly (I:C) are derivatized and coupled to MelanA 16-35 A/L containing a N-terminal C extension (cGHGHSYTTAE ELAGIGILTV) (SEQ ID NO: 55), resulting in AP205-G8-8-MelanA VLPs. AP205 VLPs, in 20 mM Hepes, pH 7.4 are derivatized with a 20-fold molar excess of SMPH for 0.5 h at 25° C., and subsequently dialysed two times against 20 mM HEPES, pH 7.4 at 4° C. to remove unreacted SMPH. Peptide is added to the dialyzed derivatization mixture in a 10-fold molar excess and allowed to react for 2 h in a thermomixer at 25° C. Samples are dialysed in 10.000 MWCO dialysis tubing against 20 mM Hepes pH 7.4 for 2 h at 4° C., and after buffer exchange, overnight against the same buffer. After dialysis, samples are clarified as described in Example 11 and protein concentration in the supernatants are determined by Bradford analysis. Coupling efficiency of peptide MelanA 16-35 A/L to AP205 is analysed by SDS-PAGE on 16% PAGE Tris-Glycine gels. Poly (I:C) packaging is analysed on 1% agarose gels and, after proteinase K digestion, on TBE gels as described in Example 7.

Packaging of poly (I:C) into ZnSO4 treated AP205 VLPs and the coupling product AP205-pIC-MelanA after coupling to MelanA is analyzed by agarose gelelectrophoresis. Coupling efficiency of the MelanA peptide is estimated from the appearance of multiple coupling products visible as bands migrating slower than AP205 VLP subunit monomer, which do not react with peptide, after SDS-PAGE analysis on a 16% PAGE Tris-Glycine gel electrophoresis. The packaging efficiency can be estimated from the TBE gel.

EXAMPLE 15

Packaging of Immunostimulatory Guanosine Flanked Oligonucleotides into HBcAg VLPs.

HBcAg VLPs are treated with RNaseA under low ionic strength conditions (20 mM Hepes pH 7.4) as described in Example 9 to hydrolyse RNA content of the VLP. After dialysis against 20 mM Hepes, pH 7.4, VLPs are mixed with guanosine flanked oligonucleotides (Table 3; G3-6, G7-7, G8-8, G9-9, G10-PO or G6, 1 mM stock in 10 mM Tris pH 8) and incubated as described in Example 12. Subsequently, VLPs are treated with Benzonase and dialysed in 300.000 MWCO tubing. Packaging is analysed on 1% agarose gels and on TBE/urea gels after proteinase K digestion as described in Example 7.

EXAMPLE 16

Packaging of Immunostimulatory Guanosine Flanked Oligonucleotides into GA VLPs.

GA VLPs are treated with RNaseA under low ionic conditions (20 mM Hepes pH 7.4) as described in Example 9 to hydrolyse RNA content of the VLP. After dialysis against 20 mM Hepes pH 7.4, VLPs are mixed with guanosine flanked oligonucleotides (Table 3; G3-6, G7-7, G8-8, G9-9, G10-PO or G6, 1 mM stock in 10 mM Tris pH8) and incubated as described in Example 12. Subsequently, VLPs are treated with Benzonase and dialysed in 300.000 MWCO tubing. Packaging is analysed on 1% agarose gels and on TBE/urea gels after proteinase K digestion as described in Example 7.

EXAMPLE 17

Packaging Ribonucleic Acid into HBcAg VLPs.

HBcAg VLPs are treated with ZnSO4 under low ionic strength conditions (20 mM Hepes pH 7.4 or 4 mM Hepes, 30 mM NaCl, pH 7.4 ) as described in Example 11 and are dialysed against 20 mM Hepes pH 7.4 as in Example 12. Poly (I:C) is added in a 10-fold molar excess to HBcAg VLPs (1-1.5 mg/ml) and incubated for 3 h at 37° C. in a thermomixer at 650 rpm as described in Example 14. Subsequently, excess of free poly (I:C) is enzymatically hydrolysed by incubation with 125 U Benzonase per ml VLP mixture in the presence of 2 mM MgCl2 for 3 h at 37° C. in a thermomixer at 300 rpm. Samples are clarified after Benzonase hydrolysis as described in Example 11 and dialysed as in Example 14. After dialysis, samples are clarified as described in Example 11 and protein concentration in the supernatants are determined by Bradford analysis. HBcAg VLPs (1 mg/l) packaged with poly (I:C) are derivatized and coupled to MelanA, and dialysed as in Example 14.

EXAMPLE 18

Packaging Ribonucleic Acid into GA VLPs.

GA VLPs are treated with ZnSO4 under low ionic strength conditions (20 mM Hepes pH 7.4 or 4 mM Hepes, 30 mM NaCl, pH 7.4 ) as described in Example 11 and are dialysed against 20 mM Hepes, pH 7.4 as in Example 12. Poly (I:C) is added in a 10-fold molecular excess to GA VLPs (1-1.5 mg/ml) and incubated for 3 h at 37° C. in a thermomixer at 650 rpm as described in Example 14. Subsequently, excess of free poly (I:C) is enzymatically hydrolysed by incubation with 125 U Benzonase per ml VLP mixture in the presence of 2 mM MgCl2 for 3 h at 37° C. in a thermomixer at 300 rpm. Samples are clarified after Benzonase hydrolysis as described in Example 11 and dialysed as in Example 14. After dialysis, samples are clarified as described in Example 11 and protein concentration in the supernatants are determined by Bradford analysis. GA VLPs (1 mg/ml) packaged with poly (I:C) are derivatized and coupled to MelanA, and dialysed as in Example 14.

EXAMPLE 19

Qβ Disassembly, Reassembly and Packaging of Oligodeoxynucleotides.

Disassembly and Reassembly of Qβ VLP

Disassembly: 45 mg Qβ VLP (2.5 mg/ml, as determined by Bradford analysis) in PBS (20 mM Phosphate, 150 mM NaCl, pH 7.5), was reduced with 10 mM DTT for 15 min at RT under stirring conditions. A second incubation of 15 min at RT under stirring conditions followed after addition of magnesium chloride to a final concentration of 700 mM, leading to precipitation of the encapsulated host cell RNA and concomitant disintegration of the VLPs. The solution was centrifuged 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatography purification steps.

Two-step purification method for Qβ coat protein by cation exchange chromatography and size exclusion chromatography: The supernatant of the disassembly reaction, containing dimeric coat protein, host cell proteins and residual host cell RNA, was applied onto a SP-Sepharose FF column (xk16/20, 6 ml, Amersham Bioscience). During the run, which was carried out at RT with a flow rate of 5 ml/min, the absorbance at 260 nm and 280 nm was monitored. The column was equilibrated with 20 mM sodium phosphate buffer pH 7 and the sample was diluted 1:15 in water to adjust a conductivity below 10 mS/cm in order to achieve proper binding of the coat protein to the column. The elution of the bound coat protein was accomplished by a step gradient to 20 mM sodium phosphate/500 mM sodium chloride and the protein was collected in a fraction volume of approx. 25 ml. The column was regenerated with 0.5 M NaOH.

In the second step, the isolated Qβ coat protein dimer (the eluted fraction from the cation exchange column) was applied (in two runs) onto a Sephacryl S-100 HR column (xk26/60, 320 ml, Amersham Bioscience) equilibrated with 20 mM sodium phosphate/250 mM sodium chloride; pH 6.5. Chromatography was performed at RT with a flow rate of 2.5 ml/min. Absorbance was monitored at 260 nm and 280 nm. Fractions of 5 ml were collected. The column was regenerated with 0.5 M NaOH.

Reassembly by dialysis: A stock solution of purified Qβ coat protein dimer at a concentration of 2 mg/ml was used for the reassembly of Qβ VLP in the presence of the oligodeoxynucleotide G8-8 or G10-PO. The concentration of oligodeoxynucleotide in the reassembly mixture was 10 μM. The concentration of coat protein dimer in the reassembly mixture was 40 μM (approx. 1.13 mg/ml). Stock solutions of urea and DTT were added to the solution to give final concentrations of 1 M urea and 5 mM DTT respectively. The oligodeoxynucleotide was added as last component, together with $H_2O$, giving a final volume of the reassembly reaction of 3 ml. This solution was dialysed at 4° C. for 72 h against 1500 ml buffer containing 20 mM TrisHCl, 150 mM NaCl, pH 8.0. The dialysed reassembly mixture was centrifuged at 14 000 rpm for 10 minutes at 4° C. A negligible sediment was discarded while the supernatant contained the reassembled and packaged VLPs. Reassembled and packaged VLPs were concentrated with centrifugal filter devices (Millipore, UFV4BCC25, 5K NMWL) to a final protein concentration of 3 mg/ml. Protein concentration was determined by Bradford analysis.

Purification of reassembled and packaged VLPs by size exclusion chromatography: Up to 10 mg total protein was loaded onto a Sepharose™ CL-4B column (xk16/70, Amersham Biosciences) equilibrated with 20 mM HEPES, 150 mM NaCl, pH 7.4. The chromatography was performed at room temperature at a flow-rate of 0.4 ml/min. Absorbance was monitored at 260 nm and 280 nm. Two peaks were observed, collected in fractions of 0.5 ml size and analysed by SDS-PAGE. The disulfide-bond pattern in reassembled and purified Qβ capsids was analyzed by non-reducing SDS-PAGE. 5 μg of the indicated capsids were mixed with sample buffer (containing SDS) that contained no reducing agent and loaded onto a 16% Tris-Glycine gel. After the run was completed the gel was stained with Coomassie blue. When compared to "intact" capsids purified from *E. coli*, the reassembled Qβ VLP displayed the same disulfide bond pattern with the bands corresponding to dimer, trimer, tetramer, pentamer and hexamers of the Qb coat protein. Calibration of the column with intact and highly purified Qβ capsids from *E. coli* revealed that the apparent molecular weight of the major first peak was consistent with Qβ capsids.

Reassembly by diafiltration (optimized method): 20 ml of a stock solution of purified coat protein (1.5 mg/ml) was mixed with stock solutions of urea, DTT, oligodeoxynucleotide G10-PO and water. The oligodeoxynucleotide was added as last component. The volume of the mixture was 30 ml and the final concentrations of the components are 35 μM dimeric coat protein (reflecting 1 mg/ml), 35 μg oligodeoxynucleotide, 1 M urea and 2.5 mM DTT. The mixture was then diafiltrated against 300 ml of 20 mM sodium phosphate/250 mM sodium chloride, pH 7.2, in a tangential flow filtration apparatus at RT, using a Pellicon XL membrane cartridge (Biomax 5K, Millipore). The total flow rate was set to 10 ml/min and the permeate flow rate set to 2.5 ml/min. After completion of the diafiltration step, $H_2O_2$ was added to the solution to a final concentration of 7 mM and the solution was further incubated at RT for 60 min, to accelerate the formation of the structural disulfide bonds in the formed VLPs. The removal of non-incorporated oligodeoxynucleotide and coat protein was achieved by a $2^{nd}$ diafiltration against 600 ml of 20 mM sodium phosphate/250 mM sodium chloride, pH 7.2, using a Pellicon XL membrane cartridge (PLCMK 300K, Millipore).

Analysis of Qβ VLPs which had been reassembled in the presence of oligodeoxynucleotides:

A) Hydrodynamic size of reassembled capsids: Qβ capsids, which had been reassembled in the presence of oligodeoxynucleotide G8-8, were analyzed by dynamic light scattering (DLS) and compared to intact Qβ VLPs, which had been purified from *E. coli*. Reassembled capsids showed the same hydrodynamic size (which depends both on mass and conformation) as the intact Qβ VLPs.

B) Disulfide-bond formation in reassembled capsids: Reassembled Qβ VLPs were analyzed by non-reducing SDS-PAGE and compared to intact Qβ VLPs, which had been purified from *E. coli*. Reassembled capsids displayed a band pattern, with the presence of disulfide-linked pentameric and hexameric forms of the coat protein, similar to the intact Qβ VLPs (as described above).

C) Analysis of nucleic acid content of the Qβ VLPs which had been reassembled in the presence of oligodeoxynucleotides by denaturing polyacrylamide TBE-Urea gelelectrophoresis: Reassembled Qβ VLPs (0.4 mg/ml) containing G8-8 oligodeoxynucleotides were incubated for 2 h at 37° C. with 125 U benzonase per ml Qβ VLPs in the presence of 2 mM $MgCl_2$. Subsequently the benzonase treated Qβ VLPs were treated with proteinase K (PCR-grade, Roche Molecular Biochemicals, Cat. No. 1964364) as described in Example 7. The reactions were then mixed with a TBE-Urea sample buffer and loaded on a 15% polyacrylamide TBE-Urea gel (Novex®, Invitrogen Cat. No.

EC6885). As a qualitative as well as quantitative standard, 1 pmol, 5 pmol and 10 pmol of the oligodeoxynucleotide which was used for the reassembling reaction, was loaded on the same gel. This gel was stained with SYBR®-Gold (Molecular Probes Cat. No. S-11494). The SYBR®-Gold stain showed that the reassembled Qβ capsids contained nucleic acid co-migrating with the oligodeoxynucleotides which were used in the reassembly reaction. Taken together, resistance to benzonase digestion of the nucleic acid content of the Qβ VLPs which had been reassembled in the presence of oligodeoxynucleotides and isolation of the oligodeoxynucleotide from purified particles by proteinase K digestion, demonstrate packaging of the oligodeoxynucleotide.

EXAMPLE 20

Coupling of Peptides Derived from MelanA Melanoma Antigen to Qb

TABLE 4

The following MelanA peptide moieties were chemically synthesized:

| Abbreviation* | Sequence** | SEQ ID NO: |
|---|---|---|
| | ELAGIGILTV | 50 |
| | GHGHSYTTAE ELAGIGILTV | 51 |
| | SYTTAEELAGIGILTV ILGVL | 52 |
| | ELAGIGILTVILGVL | 53 |
| MelanA 16-35 | c GHGHSYTTAE EAAGIGILTV | 54 |
| MelanA 16-35 A/L | c GHGHSYTTAE ELAGIGILTV | 55 |
| MelanA 26-35 | cgg EAAGIGILTV | 56 |
| MelanA 26-35 A/L | cgg ELAGIGILTY | 57 |
| MelanA 20-40 A/L | c SYTTAEELAGIGILTV ILGVL | 58 |
| MelanA 26-40 A/L | cgg ELAGIGILTVILGVL | 59 |
| MelanA 26-35-C A/L | ELAGIGILTV ggc | 60 |
| CSPKSL-MelanA 26-35 A/L | CSPKSLELAGIGILTV | 92 |
| MelanA 26-40-C A/L | ELAGIGILTVILGVLGGC | 93 |

*A/L indicates alanin to lysine exchange compared to the original wildtype MelanA peptide
**amino acids from the linker sequence are indicated in small letters The following procedures were used for chemical coupling of the MelanA peptide moieties to Qb VLPs:

For peptide MelanA 16-35, MelanA 16-35 A/L and MelanA 26-35-C A/L: A solution of 2 ml of 3.06 mg/ml Qb VLPs in 20 mM Hepes, pH 7.2 was reacted for 30 minutes with 18.4 μl of a solution of 50 mM SMPH (succinimidyl-6-(β-maleimidopropionoamido hexanoate, Pierce) in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 18.4 μl of 50 mM peptide stock solution (in DMSO) for two hours at 25° C. on a rocking shaker. The reaction mixture was subsequently dialyzed 2×2 hours against 2 liters of 20 mM Hepes, pH 7.2 at 4° C. The coupled products were named Qb-MelanA 16-35 (SEQ ID NO: 54), Qb-MelanA 16-35 A/L (SEQ ID NO: 55) and Qb-MelanA 26-35-C A/L (SEQ ID NO: 60). For MelanA 26-35: A solution of 2 ml of 3.06 mg/ml Qb capsid protein in 20 mM Hepes, pH 7.2 was reacted for 30 minutes with 75.3 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 37.7 μl of 50 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-35.

For MelanA 26-35 A/L (SEQ ID NO: 57): A solution of 2 ml of 3.06 mg/ml Qb VLPs in 20 mM Hepes, pH 7.2 was reacted for 30 minutes with 37.7 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 18.4 μl of 50 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-35 A/L.

For MelanA 20-40 A/L (SEQ ID NO: 58): A solution of 2 ml of 3.06 mg/ml Qb VLPs in 20 mM Hepes, pH 7.2 was reacted for 30 minutes with 18.4 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 184 μl of 5 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 20-40 A/L.

For MelanA 26-40 A/L (SEQ ID NO: 59): A solution of 2 ml of 3.06 mg/ml Qb VLPs in 20 mM Hepes, pH 7.2 was reacted for 30 minutes with 37.7 μl of a solution of 50 mM SMPH in DMSO at 25° C. on a rocking shaker. The reaction solution was subsequently dialyzed twice for 2 hours against 2 L of 20 mM Hepes, pH 7.2 at 4° C. 2 ml of the dialyzed reaction mixture was then reacted with 184 μl of 5 mM peptide stock solution (in DMSO) for 4 hours at 25° C. on a rocking shaker. The reaction mixture was subsequently dialyzed 2×2 hours against 2 liters of 20 mM Hepes, pH 7.2 at 4° C. The coupled product was named Qb-MelanA 26-40 A/L.

Coupling efficiency was checked by SDS-PAGE analysis. FIG. 1 shows the SDS-PAGE analysis of Qb-MelanA VLPs. MelanA-peptides were coupled to Qb VLPs. The final products were mixed with sample buffer and separated under reduced conditions on 16% Novex® Tris-Glycine gels for 1.5 hours at 125 V. The separated proteins were stained by soaking the gel in Coomassie blue solution. Background staining was removed by washing the gel in 50% methanol, 8% acetic acid. The Molecular weight marker (P 77085, New England BioLabs, Beverly, USA) was used as reference for Qb-MelanA migration velocity (lane 1). 14 μg of either Qb alone (lane 2) or Qb derivatized with SMPH (lane 3) were loaded for comparison with 8 μg of each final product: Qb-MelanA 16-35 (lane 4), Qb-MelanA 16-35 A/L (lane 5), Qb-MelanA 26-35 (lane 6) and Qb-MelanA 26-35 A/L (lane7).

The MelanA 16-35 A/L peptide contains the cytotoxic T lymphocyte (CTL) epitope MelanA 26-35 and Qb-MelanA 16-35 A/L was further studied for its immunogenicity in vitro and in vivo.

EXAMPLE 21

Qβ MelanA 16-35 A/L VLPs are Processed by Dendritic Cells and they are Presented in Vitro to T Cells Generation of MelanA-Specific T Cells in Vitro In order to assess the immunogenicity of Qb-MelanA 16-35 A/L vaccine, MelanA-specific T cells were generated in vitro. Immature monocyte-derived dendritic cells (DC) from HLA-A2 healthy volunteers were generated, as previously described (Salusto, F. et al. 1994, J. Exp. Med.179: 1109). DC (0.5×106/well) were pulsed either mock or with 40 μg/ml Qb-MelanA 16-35 A/L for 2 h at 37° C. To increase the frequency of MelanA-specific CTL precursors, autologous CD8 T cells were isolated from PBMC by magnetic sorting (Miltenyi Biotech). 1×106/well CD8 T cells were added to antigen-pulsed DC. IL-2 was supplemented in the cell culture at day 3 at a concentration of 10 U/ml and was increased up to 50 U/ml till day 12.

The expansion of MelanA-specific CD8 T cells in the cell lines was assessed by staining with phycoerythrin (PE)-labelled tetramers made of HLA-A2 loaded with MelanA 26-35 peptide (HLA-A2-MelanA-PE), as previously described (Romero, P. et all, 1998, J. Exp. Med. 1998, 188: 1641). Cells were labelled for 1 h at room temperature with HLA-A2-MelanA 26-35-PE, then anti-CD8-FITC antibody (BD PharMingen, San Jose, USA) was added for 30 min on ice. After washing, cells were analysed on a FACS Calibur using CellQuest software. Cells were acquired in the forward scatter and side scatter and the lymphocytes were gated. From this lymphocyte population, only CD8 positive T cells were selected for further analyses. The amount of MelanA-specific CD8+ T cells was calculated as percentage of HLA-A2-MelanA positive cells out of CD8+ lymphocytes. Qb-MelanA 16-35 A/L vaccine induced proliferation of MelanA 26-35 A/L-specific CTL (9.7% of CD8 T cells), demonstrating that the vaccine is efficiently taken up, processed to the CTL epitope (MelanA 26-35 A/L) and presented by human DC to T cells.

MelanA CTL were enriched by FACS sorting (FACSVantage, Becton Dickenson) and cloned by limiting dilutions, as described previously (Knuth, A. 1989, PNAS, 86:2804). CTL clones were selected for positive staining with HLA-A2-MelanA-PE tetramers. CTL were periodically restimulated by phitohaemaglutinin-activated heterologous irradiated PBMC.

Assessment of Antigen Recognition by CTL Clones

51Cr release assay was performed to analyze the functional activity of MelanA CTL clones. APC were incubated for 1.5 h with 10-6M MelanA 26-35 A/L peptide or 10-6M influenza M1 peptide as a negative control. APC were incubated with Cr51 to measure the unspecific uptake of radionucleotides at the time of peptide pulsing. After extensive washing to remove residual antigen and radioactivity, 104/well APC were incubated with varying numbers of MelanA-specific T cells for 5 h. The supernatants were collected and the specific lysis of MelanA-presenting APC by MelanA-specific T cells was calculated following the equation:

% Specific lysis=((cpm experimental−cpm spontaneous)/(cpm maximum−cpm spontaneous))×100, where cpm experimental are the radioactive counts measured in the experimental sample, cpm spontaneous are the counts obtained from APC pulsed with 51Cr without adding T cells and cpm maximum are the counts obtained from 51Cr-pulsed APC lysed with 1% NP-40.

APC loaded with MelanA 26-35 A/L but not with the irrelevant M1 peptide were efficiently lysed by CTL (70-85% specific lysis), which confirms the antigenic specificity of CTL clones.

EXAMPLE 22

Capacity of Immunostimulatory Sequences (ISS) to Activate Human Cells In Vitro

In order to select for the optimal ISS to be loaded in Qb-MelanA vaccine, series of CpG with different number of flanking Gs or double stranded RNA, such as poly (I:C) were tested for their ability to upregulate CD69 on human CD8 T cells and to induce secretion of IFN alpha and IL-12 in human PBMC.

Human PBMC were isolated from buffy coats and treated with the indicated ISS in RPMI medium containing 10% FCS for 18 h. IFN alpha in the supernatants was measured by ELISA, using an antibody set provided by PBL Biomedical Laboratories. PBMC were stained with mouse anti-human CD8-FITC, mouse anti-human CD19-PE and anti-human CD69-APC and analyzed by flow cytometry. G10-PO was the most active ISS in inducing IFN alpha secretion (FIG. 2A). G9-9 and G8-8 were a bit less active than G10-PO, although they induced high levels of IFN alpha secretion. Decreasing the number of flanking Gs in the other oligonucleotides resulted in lower IFN alpha secretion. Poly (I:C)-treated PBMC did not release any IFN alpha, although poly (I:C)-treated T and B cells from PBMC upregulated CD69 (FIG. 2B). Poly (I:C) also induced IL-12 secretion from PBMC and monocyte-derived DC.

Treatment of PBMC with G10-PO, G9-9 and G8-8 upregulated CD69 on the cell membrane of CD8 T cells to a nearly similar extend. Decreasing the number of flanking Gs (below 7) in the other oligonucleotides reduced their activity to induce secretion of IFN alpha (FIG. 2A) and to upregulate CD69 on T cells (FIG. 2B). These data show that G10-PO, G9-9 and G8-8 have comparable high activity on human cells, therefore they can be used as ISS in Qb-MelanA vaccine.

EXAMPLE 23

In Vitro Expansion of MelanA-Specific T Cells is Increased by G10-PO

The ability of Qb-MelanA VLPs to induce in vitro proliferation of MelanA specific CTL was tested in the presence or absence of G10-PO. Immature human monocyte-derived DC (0.5×106/well) were pulsed with either Qb-MelanA 16-35 A/L or MelanA 26-35 A/L peptide or mock as in Example 21. Human monocyte-derived DC are toll-like receptor-9 (TLR-9)-negative and therefore they do not respond to CpG. B cells and plasmacytoid DC present in human PBMC are TLR-9 positive and respond to CpG treatment with production of cytokines (IFN alpha, IL-12).To investigate the role of G10-PO on the antigen-presenting capacity of monocyte-derived DC, antigen-pulsed DC were washed and incubated with 1×106 autologous PBMC in the presence or absence of 2 μM G10-PO for 2 h. Autologous CD8 T cells (1×106), isolated by magnetic sorting were added to APC and incubated for 12 days using the cell culture conditions, described in Example 21. MelanA-specific CTL were detected by HLA-A2-MelanA-PE tetramer staining and flow cytometry analysis. Adding G10-PO to the Qb-MelanA-pulsed DC increased the frequency of specific CTL (from 10% to 14%), which indicates that the cytokine milieu, created by CpG stimulation is favourable for CTL expansion in vitro.

EXAMPLE 24

Qbx33 VLPs Loaded with G3-6, G6, G10-PO or Poly (I:C) Induces Protection against p33-Recombinant Vaccinia Virus Challenge B6 mice were subcutaneously immunized with Qbx33 alone or loaded with G3-6 or G6 or poly (I:C) (see Examples 12 and 14). Eight days later, mice were challenged with 1.5×106 pfu of recombinant Vaccinia virus, expressing the LCMV-p33 antigen. After 4 days, mice were sacrificed and the viral titers in ovaries were measured as previously described (Bachmann et al, Eur. J. Imunol. 1994, 24:2228). As depicted in FIG. 3, all mice receiving the Qbx33 vaccine loaded with either G3-6 or G6 or poly (I:C) were protected from viral challenge. In contrast, naïve mice and mice immunized with Qbx33 alone did not eliminate the virus from the ovaries. These data demonstrate that VLP alone is not sufficient to induce protective CTL immune response, whereas VLP loaded with CpG or poly (I:C) are very efficient in priming naïve CTL.

Similarly, immunization of mice with Qbx33 loaded with G10-PO was priming p33-specific CTL (6.2%±1.4% vs 0.2%±0.1% in naïve mice), as well as inducing protection from recombinant Vaccinia virus challenge.

EXAMPLE 25

Qβ⁻ MelanA 16-35 A/L VLPs are processed and presented by the human MHC class I allele HLA-A0201 and induces expansion of functional MelanA-specific CD8+T cells in HLA-A2 transgenic mice HHD mice express a chimeric monochain class I molecule with a human β2-microglobulin covalently linked to the N-terminus of A2 α1 and α2 domains fused with Db α3 domain (Firat, H. et al 1999, Eur.J.Immunol., 29:3112). The HLA-A2 transgene expression in these mice allows investigating the capacity of Qβ MelanA 16-35 A/L VLPs to be processed and presented as the CTL epitope MelanA 26-35 and to prime CTL in vivo. Furthermore, the effect of adjuvants, as ISS can be studied in vivo.

HHD mice were either left untreated or immunized by injecting subcutaneously 100 μg Qb-MelanA 16-35 A/L or Qb-pIC-MelanA 16-35 A/L. Eight days later spleenocytes were isolated, resuspended in FACS buffer (PBS, 2% FCS, 5 mM EDTA, pH 8.2) and stained with HLA-A2-MelanA-PE labelled tetramers for 30 min at room temperature. In a second step, rat anti-mouse CD8-APC (BD PharMingen, San Jose, USA) and anti mouse Mel14-FITC (BD PharMingen, San Jose, USA) were added for 30 min at 4° C. After washing, erythrocytes were lysed with BD-Lyzing Solution (BD Biosciences, San Jose, USA) for 10 min at room temperature. Finally, the spleen cells were analysed on a FACS Calibur using CellQuest software. First of all, the cells were acquired in the forward scatter and side scatter and the lymphocytes were gated. From this lymphocyte population, only the CD8 positive T cells were selected for further analyses. The HLA-A2-MelanA-PE and Mel 14-FITC labelled cells were measured with the FL2 and FL1 detector, respectively. The amount of MelanA-specific, activated CD8+ T cells was calculated as percent HLA-A2-MelanA positive, Mel14 negative cells on total CD8+ lymphocytes.

Flow cytometry analysis showed that Qb-pIC-MelanA 16-35 A/L induced a surprisingly high expansion of MelanA-specific activated CD8+Mel14- T cells (2.43% and 0.73%), which was higher compared to untreated animals (0.22% and 0.37%). It should be noted that the capacity of the vaccine increased significantly only when Qb-MelanA was loaded with poly (I:C).

The human HLA-A2-MelanA tetramer as used above does not bind very efficiently to mouse MelanA-specific T cells, as the protein is chimeric. Therefore we could assume a much higher degree of antigen specific T cells in these mice.

In a similar experiment we analysed the efficiency of Qb-G10-MelanA 16-35 A/L to prime CTL in vivo with vaccination with the peptide mixed with CpG and IFA. HHD mice were immunized either with 200 μg Qβ-G10-MelanA 16-35 A/L or with 50 μg MelanA 16-35 A/L mixed with 20 nmol CpG and Incomplete Freud's Adjuvant (IFA) or left untreated. Eight days later viable lymphocytes were isolated from the spleens and stained for MelanA-specific CD8+T cells. Staining was performed in FACS buffer for 1.5 h at 37° C. with a PE-labelled tetramer specific for the chimeric HLA-A2α1α2Kbα3 MHC class I molecule loaded with the MelanA 26-35 peptid. In a second step, rat anti-mouse CD8-APC (BD PharMingen, San Jose, USA) and anti mouse Mell4-FITC (BD PharMingen, San Jose, USA) was added for 30 min at 4° C. Finally, the spleen cells were analysed on a FACS Calibur using CellQuest software.

Flow cytometry analysis showed that Qβ-G10-MelanA 16-35 A/L induced expansion of MelanA-specific activated $CD8^+Mell4^-$T cells (18.2%) which was higher compared to untreated animals (2%) or animal receiving equimolar amounts of MelanA A/L 16-35 mixed with 20 nmol CpG and IFA (2.0%). It should be noted that the capacity of the vaccine increased only when Qb-MelanA was loaded with G10-PO.

In a similar experimental setting, immunization of HHD mice with Qb-MelanA 16-35 A/L or Qb-MelanA 26-35 A/L loaded with G8-8 or G10 PO induces expansion of HLA-A2-MelanA—positive and Mell4 negative CD8 T cells.

Taken together these findings demonstrate the ability of ISS loaded Qb-peptide vaccines to very efficiently prime CTL against foreign and self antigens.

EXAMPLE 26

Qbx33 Loaded with CpG can be used in Homologous as Well in Heterologous Prime-Boost Regimen for the Induction of a Long Lasting Memory CD8+ T Cell Response Mice were immunized with 150 ug Qbx33/NKCpG and 8 days later the frequencies of p33-specific T cells increased from 0.4%±0.2% in naïve mice to 7.5%±2.2% in immunized animals as measured with antigen.specific MHC/peptide tetramers. 20 days later the peptide specific CD8+ T population dropped down to 1.6%±0.7%. A second-immunization of these mice 30 days after the first immunisation with 150 ug Qbx33/NKPS could boost the memory T cell response to up to 8.4%±1.9% specific T cells. This response dropped slowly down but could be boosted again 4 months after the first boost with 150 ug Qbx33/NKPS reaching T cell levels of 23.8%±5.2%.

When 3 mice were primed with 50 ug p33 peptide mixed with 20 nmol NKPS and IFA only 0.6%± 0.4% specific CD8+ T cells could be induced until day 8 post-immunisation. Nevertheless, this low response could be boosted efficiently 7 weeks later with Qbx33/NKPS to levels of 28.5%±9.8%.

Immunisation with 1×10 exp 6 plaque forming units of recombinant vaccinia virus expressing the p33-peptide could hardly induce any T cell response (1.1%±0.5%) but was boosted very efficiently boosted 6 months later with 150 ug Qbx33/NKPS to T cells levels of 28.1± 4.2%.

These results show, that Qb loaded with CpG very efficiently boosts any pre-existing T cell response in heterologous as well as homologous prime boost regimens. It should be noted, that Qb/NKPS can even boost a very inefficiently primed T cell response with peptides or recombinant viruses. In addition, when a strong T cell response was established with Qbx33/NKPS we were able to boost this response using an immunologically effective amount of a heterologous vaccine such as the p33 peptide alone, recombinant virus expressing p33, or p33 fused or coupled to a VLP. In the latter, the used VLP is not a VLP derived from RNA phage Qb but e.g. HBcAg or VLP derived from AP205.

The invention claimed is:

1. A composition comprising:

(a) a virus-like particle;

(b) at least one immunostimulatory substance;

(i) wherein said immunostimulatory substance is an immunostimulatory nucleic acid; and (ii) wherein said immunostimulatory substance is packaged into said virus-like particle; and (c) at least one antigen or antigenic determinant;

(i) wherein said antigen or antigenic determinant is bound to said virus-like particle; and (ii) wherein said antigen or antigenic determinant comprises a human melanoma MelanA peptide analogue that comprises an amino acid sequence derived from the amino acid sequence of SEQ ID NO:78 or SEQ ID NO:79 by alteration of one or two amino acid(s) or amino acid derivative(s) in said amino acid sequence, wherein said alteration comprises an amino acid substitution, deletion or insertion or a combination thereof.

2. The composition of claim 1, wherein said antigen or antigenic determinant is bound to said virus-like particle by at least one nonpeptide covalent bond.

3. The composition of claim 1, wherein said human melanoma MelanA peptide analogue is characterized by one or two amino acid substitutions with respect to the normal MelanA peptide.

4. The composition of claim 1, wherein said human melanoma MelanA peptide analogue comprises an amino acid sequence selected from the group consisting of:

(a) LAGIGILTV (SEQ ID NO:84);

(b) MAGIGILTV (SEQ ID NO:85);

(c) EAMGIGILTV (SEQ ID NO: 86);

(d) ELAGIGILTV (SEQ ID NO: 50);

(e) EMAGIGILTV (SEQ ID NO: 87);

(f) YAAGIGILTV (SEQ ID NO: 88); and (g) FAAGIGILTV (SEQ ID NO: 89).

5. The composition of claim 1, wherein said human melanoma MelanA peptide analogue comprises the sequence ELAGIGILTV (SEQ ID NO:50).

6. The composition of claim 1, wherein said virus-like particle comprises at least one first attachment site and wherein said antigen or antigenic determinant further comprises at least one second attachment site being selected from the group consisting of:

(a) an attachment site not naturally occurring with said antigen or antigenic determinant; and (b) an attachment site naturally occurring with said antigen or antigenic determinant;

and wherein said binding of said antigen or antigenic determinant to said virus-like particle is effected through association between said first attachment site and said second attachment site and wherein said antigen or antigenic determinant and said virus-like particle interact through said association to form an ordered and repetitive antigen array.

7. The composition of claim 6, wherein said first attachment site comprises an amino group.

8. The composition of claim 6, wherein said second attachment site comprises a sulfhydryl group.

9. The composition of claim 6, wherein said first attachment site is an amino group and said second attachment site is a sulfhydryl group.

10. The composition of claim 6, wherein said human melanoma MelanA peptide analogue with said second attachment site comprises an amino acid sequence selected from the group consisting of:

(a) CGHGHSYTTAEELAGIGILTV (SEQ ID NO:55);

(b) CGGELAGIGILTV (SEQ ID NO:57);

(c) CSYTTAEELAGIGILTVILGVL (SEQ ID NO:58);

(d) CGGELAGIGILTVILGVL (SEQ ID NO:59);

(e) ELAGIGILTVGGC (SEQ ID NO:60);

(f) CSPKSLELAGIGILTV (SEQ ID NO:92); and (g) ELAGIGILTVILGVLGGC (SEQ ID NO:93).

11. The composition of claim 6, wherein said human melanoma MelanA peptide analogue with said second attachment site comprises the amino acid sequence CGHGHSYTTAEELAGIGILTV (SEQ ID NO:55).

12. The composition of claim 1, wherein said virus-like particle is a recombinant virus-like particle, wherein said virus like particle comprises recombinant proteins selected from the group consisting of:

(a) recombinant proteins of Hepatitis B virus;

(b) recombinant proteins of measles virus;

(c) recombinant proteins of Sindbis virus;

(d) recombinant proteins of Rotavirus;

(e) recombinant proteins of Foot-and-Mouth-Disease virus;

(f) recombinant proteins of Retrovirus;

(g) recombinant proteins of Norwalk virus;

(h) recombinant proteins of human Papilloma virus;

(i) recombinant proteins of BK virus;

(j) recombinant proteins of bacteriophages;

(k) recombinant proteins of RNA-phages;

(l) recombinant proteins of Ty; and (m) fragments of any of the recombinant proteins from (a) to (l).

13. The composition of claim 1, wherein said virus-like particle comprises recombinant proteins, or fragments thereof, of a RNA-phage, wherein said RNA-phage is selected from the group consisting of:

(a) bacteriophage Qβ;
(b) bacteriophage R17;
(c) bacteriophage fr;
(d) bacteriophage GA;
(e) bacteriophage SP;
(f) bacteriophage MS2;
(g) bacteriophage M11;
(h) bacteriophage MX1;
(i) bacteriophage NL95;
(j) bacteriophage f2;
(k) bacteriophage PP7; and
(l) bacteriophage AP205.

14. The composition of claim 1, wherein said virus-like particle comprises recombinant proteins, or fragments thereof, of bacteriophage Qβ or bacteriophage AP205.

15. The composition of claim 1, wherein said immunostimulatory substance is a toll-like receptor activating substance, and wherein said immunostimulatory nucleic acid is selected from the group consisting of:

(a) ribonucleic acids;
(b) deoxyribonucleic acids;
(c) chimeric nucleic acids; and
(d) mixtures of at least one nucleic acid of (a), (b) and/or (c).

16. The composition of claim 15, wherein said deoxyribonucleic acid is an unmethylated CpG-containing oligonucleotides.

17. The composition of claim 1, wherein said immunostimulatory substance is an unmethylated CpG-containing oligonucleotide.

18. The composition of claim 17, wherein said unmethylated CpG-containing oligonucleotide comprises the sequence:

5' X1X2CGX3X4 3' and wherein X1, X2, X3, and X4 are any nucleotide; and wherein at least one of said nucleotide X1, X2, X3, and X4 has a phosphate backbone modification.

19. The composition of claim 17, wherein said unmethylated CpG-containing oligonucleotide comprises a palindromic sequence.

20. The composition of claim 17, wherein said unmethylated CpG-containing oligonucleotide consists of the sequence GGGGGGGGGGGAC-GATCGTCGGGGGGGGGG (SEQ ID NO:4).

21. The composition of claim 19, wherein said palindromic sequence comprises GACGATCGTC (SEQ ID NO:1).

22. A method for enhancing an immune response against an antigen in an animal comprising introducing the composition of claim 1 into said animal, wherein an enhanced immune response against said antigen is produced in said animal.

23. The method of claim 22, wherein said immune response is an enhanced B cell response or an enhanced T cell response.

24. The method of claim 22, wherein said animal is a mammal.

25. The method of claim 22, wherein said composition is introduced into said animal subcutaneously, intramuscularly, intravenously, intranasally or directly into the lymph node.

26. An immunogenic composition comprising an immunologically effective amount of the composition of claim 1 together with a pharmaceutically acceptable diluent, carrier or excipient.

27. A method of inmmnizing or treating an animal comprising administering to said animal an immunologically effective amount of the immunogenic composition of claim 26.

28. The method of claim 27, wherein said animal is a mammal.

29. A method of immunizing or treating an animal comprising the steps of priming a T cell response in said animal, and boosting a T cell response in said animal, wherein said priming or said boosting is effected by administering an immunologically effective amount of the immunogenic composition of claim 26.

30. The method of claim 29, wherein said priming and said boosting is effected by administering an immunologically effective amount of said immunogenic composition.

31. The method of claim 23, wherein said T cell response is a CTL response or a Th cell response.

32. The method of claim 31, wherein said Th cell response is a Th1 cell response.

33. The method of claim 24, wherein said mammal is a human.

34. The immunogenic composition of claim 26, wherein said immunogenic composition further comprises an adjuvant.

35. The method of claim 28, wherein said mammal is a human.

36. The composition of claim 1, wherein said antigen or antigenic determinant consists of a human melanoma MelanA peptide analogue comprising an amino acid sequence derived from the amino acid sequence of SEQ ID NO:78 or SEQ ID NO:79 by alteration of one or two amino acid(s) or amino acid derivative(s) in said amino acid sequence, wherein said alteration comprises an amino acid substitution, deletion or insertion or a combination thereof.

37. The composition of claim 1, wherein said antigen or antigenic determinant consists of a human melanoma MelanA peptide analogue consisting of an amino acid sequence derived from the amino acid sequence of SEQ ID NO:78 or SEQ ID NO:79 by alteration of one or two amino acid(s) or amino acid derivative(s) in said amino acid sequence, wherein said alteration comprise an amino acid substitution, deletion or insertion or a combination thereof.

38. The composition of claim 1, wherein said amino acid substitution, deletion or insertion or a combination thereof is at position 1, 2, 3 or 10 of SEQ ID NO:78 or a combination thereof or at position 1, 2 or 9 of SEQ ID NO:79 or a combination thereof.

39. The composition of claim 1, wherein said human melanoma MelanA peptide analogue comprises an amino acid sequence derived from the amino acid sequence of SEQ ID NO:78 or SEQ ID NO:79 by substitution of one amino acid.

40. The composition of claim 39, wherein said substitution is at position 1, 2, 3 or 10 of SEQ ID NO:78 or a combination thereof or at position 1, 2 or 9 of SEQ ID NO:79 or a combination thereof.

41. The composition of claim 1, wherein said human melanoma MelanA peptide analogue consists of the sequence ELAGIGILTV (SEQ ID NO:50).

42. The composition of claim 1, wherein said virus-like particle comprises at least one first attachment site and wherein said antigen or antigenic determinant further comprises at least one second attachment site selected from the group consisting of:

(a) an attachment site not naturally occurring with said antigen or antigenic determinant; and
(b) an attachment site naturally occurring with said antigen or antigenic determinant;

wherein said binding of said antigen or antigenic determinant to said virus-like particle is effected through association between said first attachment site and said second attachment site.

43. The composition of claim 42, wherein said antigen or antigenic determinant and said virus-like particle interact through said association to form an ordered and repetitive antigen array.

44. The composition of claim 1, wherein said virus-like particle is a virus-like particle of an RNA-phage.

45. The composition of claim 1, wherein said virus-like particle is a virus-like particle of RNA-phage Qβ.

46. The composition of claim 1, wherein said virus-like particle comprises recombinant proteins of bacteriophage Qβ.

47. The composition of claim 1, wherein said virus-like particle comprises recombinant proteins of bacteriophage Qβ, wherein said recombinant proteins comprise SEQ ID NO:10.

48. The composition of claim 1, wherein said virus-like particle comprises recombinant proteins of bacteriophage Qβ, wherein said recombinant proteins consist of SEQ ID NO:10.

49. The composition of claim 15, wherein said ribonucleic acids are polyinosinic-polycytidylic acid double-stranded RNA (poly-(I:C)).

50. The composition of claim 1, wherein said immunostimulatory nucleic acid is not accessible to DNAse hydrolysis.

51. The composition of claim 45, wherein said unmethylated CpG-containing oligonucleotide consists of the sequence GGGGGGGGGGGACGATCGTCGGGGGGGGGG (SEQ ID NO:41).

52. The composition of claim 2, wherein said virus-like particle is a virus-like particle of RNA-phage Qβ.

53. The composition of claim 52, wherein said virus-like particle comprises recombinant proteins of bacteriophage Qβ, and wherein said human melanoma MelanA peptide analogue consists of the sequence ELAGIGILTV (SEQ ID NO:50).

54. The composition of claim 53, wherein said virus-like particle comprises at least one first attachment site and wherein said antigen or antigenic determinant further comprises at least one second attachment site selected from the group consisting of:

(a) an attachment site not naturally occurring with said antigen or antigenic determinant; and ( b) an attachment site naturally occurring with said antigen or antigenic determinant;

wherein said binding of said antigen or antigenic determinant to said virus-like particle is effected through association between said first attachment site and said second attachment site, and wherein said antigen or antigenic determinant and said virus-like particle interact through said association to form an ordered and repetitive antigen array.

55. The composition of claim 54, wherein said first attachment site is an amino group and said second attachment site is a sulfhydryl group.

56. The composition of claim 55, wherein said immunostimulatory substance is an unmethylated CpG-containing oligonucleotide, and wherein said unmethylated CpG-containing oligonucleotide consists of the sequence GGGGGGGGGGGACGATCGTCGGGGGGGGGG (SEQ ID NO:41).

57. The composition of claim 56, wherein said virus-like particle comprises recombinant proteins of bacteriophage Qβ, wherein said recombinant proteins consist of SEQ ID NO:10.

58. The composition of claim 57, wherein said human melanoma MelanA peptide analogue with said second attachment site consists of the amino acid sequence CGHGHSYTTAEELAGIGILTV (SEQ ID NO:55).

* * * * *